US011802316B2

(12) United States Patent
Zheng et al.

(10) Patent No.: US 11,802,316 B2
(45) Date of Patent: Oct. 31, 2023

(54) METHODS AND COMPOSITIONS RELATED TO T-CELL ACTIVITY

(71) Applicant: The University of Chicago, Chicago, IL (US)

(72) Inventors: Yan Zheng, Chicago, IL (US); Yuanyuan Zha, Chicago, IL (US); Robbert M. Spaapen, Chicago, IL (US); Thomas F. Gajewski, Chicago, IL (US)

(73) Assignee: The University of Chicago, Chicago, IL (US)

( * ) Notice: Subject to any disclaimer, the term of this patent is extended or adjusted under 35 U.S.C. 154(b) by 93 days.

(21) Appl. No.: 16/948,455

(22) Filed: Sep. 18, 2020

(65) Prior Publication Data

US 2021/0139994 A1 May 13, 2021

Related U.S. Application Data

(63) Continuation of application No. 15/937,044, filed on Mar. 27, 2018, now Pat. No. 10,815,531, which is a continuation of application No. 14/777,123, filed as application No. PCT/US2014/029173 on Mar. 14, 2014, now Pat. No. 9,944,992.

(60) Provisional application No. 61/794,535, filed on Mar. 15, 2013.

(51) Int. Cl.
| | |
|---|---|
| *C12Q 1/6886* | (2018.01) |
| *A61K 31/713* | (2006.01) |
| *A61K 45/06* | (2006.01) |
| *C12N 15/113* | (2010.01) |
| *G01N 33/569* | (2006.01) |
| *G01N 33/574* | (2006.01) |
| *G16H 50/30* | (2018.01) |
| *G16Z 99/00* | (2019.01) |

(52) U.S. Cl.
CPC .......... *C12Q 1/6886* (2013.01); *A61K 31/713* (2013.01); *A61K 45/06* (2013.01); *C12N 15/113* (2013.01); *C12N 15/1137* (2013.01); *C12N 15/1138* (2013.01); *G01N 33/56972* (2013.01); *G01N 33/57484* (2013.01); *G16H 50/30* (2018.01); *G16Z 99/00* (2019.02); *C12N 2310/14* (2013.01); *C12N 2320/30* (2013.01); *C12N 2320/31* (2013.01); *C12Q 2600/158* (2013.01); *C12Q 2600/16* (2013.01); *Y02A 90/10* (2018.01)

(58) Field of Classification Search
CPC .......... C12Q 1/6886; C12Q 2600/158; A61K 31/713; A61K 45/06; C12N 15/113; C12N 15/1137; C12N 15/1138; C12N 2310/14; G01N 33/56972; G01N 33/57484

USPC ....................................... 424/133.1
See application file for complete search history.

(56) References Cited

U.S. PATENT DOCUMENTS

| | | |
|---|---|---|
| 8,137,667 B2 | 3/2012 | Jure-Kunkel et al. |
| 8,337,850 B2 | 12/2012 | Ahrens et al. |
| 2005/0266510 A1 | 12/2005 | Gajewski |
| 2007/0072209 A1 | 3/2007 | Moses et al. |
| 2012/0135014 A1 | 5/2012 | Postlethwaite et al. |

FOREIGN PATENT DOCUMENTS

| | | | |
|---|---|---|---|
| EP | 2272977 A1 * | 1/2011 | ........... C12Q 1/6883 |
| WO | WO 1994/010571 | 5/1994 | |
| WO | WO 2003/049755 | 6/2003 | |
| WO | WO 2003/074654 | 9/2003 | |
| WO | WO 2004/050706 | 6/2004 | |
| WO | WO 2004/074437 | 9/2004 | |
| WO | WO 2004/078928 | 9/2004 | |
| WO | WO 2006/050172 | 5/2006 | |
| WO | WO 2006/052900 | 5/2006 | |
| WO | WO 2007/030820 | 3/2007 | |
| WO | WO 2009/033161 | 3/2009 | |
| WO | WO 2010/019570 | 2/2010 | |
| WO | WO 2012/178160 | 12/2012 | |
| WO | WO 2014/066834 | 5/2014 | |

OTHER PUBLICATIONS

Zheng et al. (Journal of Immunotherapy, 2011, vol. 34, No. 9, pp. 723) (Year: 2011).*
"Affymetrix GeneChip Human Genome U133 Array Set HG-U133A" *NCBI Handbook GEO*, XP002355386, 2002. Retrieved on Mar. 11, 2002.
Ascierto et al., "Future perspectives in melanoma research. Meeting report from the Melanoma Bridge. Napoli, Dec. 2-4, 2012", *J Transl Med.*, 11:137, 2013.
Article 94(3) EPC Communication for EP14763660.9, dated Jan. 8, 2018.
Baixeras E., et al., "Characterization of the Lymphocyte Activation Gene 3-Encoded Protein. A New Ligand for Human Leukocyte Antigen Class II Antigens," *Journal of Experimental Medicine*, 176(2), pp. 327-337. (1992).
Bouillet & O'Reilly, "CD95, BIM and T Cell Homeostasis," *Nature Reviews Immunology.* 9, pp. 514-519. (2009).
Chan, et al., "Receptors That Interact with Nectin and Nectin-Like Proteins in the Immunosurveillance and Immunotherapy of Cancer," *Current Opinion in Immunology*, 24, pp. 246-251. (2012).

(Continued)

*Primary Examiner* — Yan Xiao
(74) *Attorney, Agent, or Firm* — Norton Rose Fulbright US LLP

(57) ABSTRACT

Embodiments concern methods and composition related to anergic T-cells in patients, such as cancer patients.

9 Claims, 17 Drawing Sheets
Specification includes a Sequence Listing.

(56) References Cited

OTHER PUBLICATIONS

Chavrier, et al., "A Gene Encoding a Protein with Zinc Fingers is Activated During G0/G1 Transition in Cultured Cells," *The EMBO Journal*, 7(1), pp. 29-35. (1988).
Diez-Guerra F. J., "Neurogranin, A Link Between Calcium/Calmodulin and Protein Kinase C Signaling in Synaptic Plasticity," *IUBMB Life*. 62(8), pp. 597-606. (2010).
Du Pasquier L., "Innate Immunity in Early Chordates and the Appearance of Adaptive Immunity," *Comptes Rendus Biologies*, 327(6), pp. 591-601. (2004).
European Search Report from the European Patent Office in corresponding Application No. EP18181943 dated Oct. 9, 2018.
Gajewski, et al., "Molecular Profiling to Identify Relevant Immune Resistance Mechanisms in the Tumor Microenvironment," *Current Opinion Immunology*, 23(2), pp. 286-292. (2011).
Glynne et al., "Genomic-Scale Gene Expression Analysis of Lymphocyte Growth, Tolerance and Malignancy," *Current Opinion in Immunology* 12, pp. 210-214. (2000).
Gras et al., "Semaphorin 7A protein variants differentially regulate T-cell activity", *Transfusion*, 53(2):270:283, 2013.
Grosso, et al., "LAG-3 Regulates CD8+ T Cell Accumulation and Effector Function in Murine Self- and Tumor-Tolerance Systems," *Journal of Clinical Investigation*, 117(11), pp. 3383-3392. (2007).
Hall, et al., "The Role of Retinoic Acid in Tolerance and Immunity," *Immunity*. 35(1), pp. 13-22. (2011).
Harris, et al., "Early Growth Response Gene-2, a Zinc-Finger Transcription Factor Is Required for Full Induction of Clonal Anergy in CD4+ T Cells," *Journal of Immunology*, 173(12), pp. 7331-7338. (2004).
Hoelzinger et al., "Blockade of CCL1 Inhibits T Regulatory Cell Suppressive Function Enhancing Tumor Immunity Without Affecting T Effector Responses," *Journal of Immunology* 184, pp. 6833-6842. (2010).
Huang, et al., "Role of LAG-3 in Regulatory T Cells", *Immunity*. 21(4), pp. 502-513, 2004.
International Search Report and Written Opinion Issued in Corresponding PCT Application No. PCT/US2014/029173, dated Oct. 2, 2014.
"International Society for Biological Therapy of Cancer 23rd Annual Meeting Abstracts", *Journal of Immunotherapy*, 31(9):921-971, 2008.
Jan, et al., "Characterization of the Expresion of the Hypoxia-Induced Genes Neuritin, TXNIP and IGFBP3 in Cancer," *FEBS Letters*, 580, pp. 3395-3400. (2006).
Lametschwandiner et al., "Development of an Effective Cancer Immune Therapy by Cbl-b Silencing," *Journal of Immunotherapy*. 31(9), p. 943. (2008).
Lechner et al., "Fingerprints of Anergic T Cells," *Current Biology*, 11, pp. 587-595. (2001).
Lesniewski, et al., "Regulation of IL-2 Expression by Transcription Factor BACH2 in Umbilical Cord Blood CD4+ T Cells," *Leukemia*, 22, pp. 2201-2207. (2008).
Naeve, et al., "Neuritin: a Gene Induced by Neural Activity and Neurotrophins that Promotes Neuritogenesis," *Proceedings of the National Academy of Sciences of the United States of America*, 94(6), pp. 2648-2653. (1997).
Nedivi, et al., "A Set of Genes Expressed in Response to Light in the Adult Cerebral Cortex and Regulated During Development," *Proceedings of the National Academy of Sciences of the United States of America*, 93(5), pp. 2048-2053. (1996).
Nedivi, et al "Promotion of Dendritic Growth by CPG15, an Activity-Induced Signaling Molecule," *Science*. 281(5384), pp. 1863-1866. (1998).
Olenchock, et al., "Disruption of Diacylglycerol Metabolism Impairs the Induction of T Cell Anergy," *Nature Immunology*. 7(11), pp. 1174-1181. (2006).
Partial Supplementary European Search Report Issued for Corresponding European Application No. EP14763660.9, dated Oct. 11, 2016.
Patwardhan, et al., "EGR3, a Novel Member of the EGR Family of Genes Encoding Immediate-Early Transcription Factors," *Oncogene*. 6(6), pp. 917-928. (1991).
Romano et al., "Meeting Report, SITC 26th Annual Meeting—Summary," *Journal of Translational Medicine*, 10, p. 105. (2012).
Safford, et al., "Egr-2 and Egr-3 are Negative Regulators of T Cell Activation," *Nature Immunology*, 6(5), pp. 472-480. (2005).
Schwartz R., "T Cell Anergy," *Annual Review of Immunology*, 21, pp. 305-334. (2003).
Shi et al., "CD4CD25 regulatory T lymphocytes in allergy and asthma", *Allergy*, 60(8):986-995, 2005.
Suzuki, et al., "Semaphorins and Their Receptors in Immune Cell Interactions," *Nature Immunology*. 9(1), pp. 17-23. (2008).
Triebel, et al., "LAG-3, a Novel Lymphocyte Activation Gene Closely Related to CD4," *Journal of Experimental Medicine*, 171(5), pp. 1393-1405. (1990).
Vlad et al., "ILT3-Fe Induces Allospecific CD8+ T Suppressor Cells Which Mediate Cell Anergy and Immunological Tolerance," *Human Immunology* 71, p. S95. (2010).
Watts T., "TNF/TNFR Family Members in Costimulation of T Cell Responses", *Annual Review Immunology*, 23, pp. 23-68. (2005).
Williams et al., "Egr2 targets identify a population of dysfunctional T cells in the tumor microenvironment with immune modulatory properties", *J Immunother Cancer.*, 1(Suppl 1):p. 194, 2013.
Zha, et al., "T cell Anergy is Reversed by Active Ras and is Regulated by . Diacylglycerol Kinase-Alpha", *Nature Immunology*, 7(11), pp. 1166-1173. (2006).
Zha, et al., "Use of Cre-Adenovirus and Car Transgenic Mice for Efficient Deletion of Genes in Post-Thymic T Cells," *Journal of Immunological Methods*, 311(1-2), pp. 94-102. (2008).
Zheng, et al., "Molecular Regulation of T-cell Anergy," *EMBO Reports*. 9(1), pp. 50-55. (2008).
Zheng, et al., "Transcriptional Regulator Early Growth Response Gene 2 (Egr2) is Required for T cell Anergy in Vitro and in Vivo," *Journal of Experimental Medicine*, 209(12), pp. 2157-2163. (2012).
Extended European Search Report issued in corresponding European Application No. 22194278.2, dated Mar. 14, 2023.

\* cited by examiner

| Gene | EntrezGene | Up | Ratio EV vs Cre |
|---|---|---|---|
| Ccl1: chemokine (C-C motif) ligand 1 | 20290 | 36.8 | 7.8 |
| Ctla4: cytotoxic and regulatory T cell molecule | 64898 | 98.2 | 7.1 |
| Egr2: early growth response 2 | 13654 | 34.3 | 5.9 |
| Rasgef1a: RasGEF domain family, member 1A | 70727 | 5.8 | 4.8 |
| Car12: carbonic anhydrase 12 | 76459 | 10.3 | 3.8 |
| Pcdc3: pleckstrin homology, Sec7 and coiled-coil domains 3 | 19159 | 4.3 | 3.7 |
| Pacsin1: protein kinase C and casein kinase substrate in neurons 1 | 23969 | 4.7 | 3.4 |
| Tnfrsf9: tumor necrosis factor receptor superfamily, member 9 | 21942 | 10.3 | 3.2 |
| Flt2: four and a half LIM domains 2 | 14200 | 10.0 | 3.2 |
| Bcl2l11: BCL2-like 11 (apoptosis facilitator) | 12125 | 8.9 | 3.1 |
| Gnb5: guanine nucleotide binding protein (G protein), beta 5 | 14697 | 4.7 | 2.9 |
| short chain dehydrogenase/reductase family 39U, member 1 | 654795 | 8.1 | 2.6 |
| Nrgn: neurogranin | 64011 | 9.6 | 2.6 |
| Crabp2: cellular retinoic acid binding protein II | 12904 | 6.4 | 2.3 |
| Sema7a: sema domain, immunoglobulin domain (Ig), and GPI membrane anchor, (semaphorin) 7A | 20361 | 4.2 | 2.1 |
| 1190002H23Rik: RIKEN cDNA 1190002H23 gene | 66214 | 4.7 | 2.1 |
| Tnfsf11: tumor necrosis factor (ligand) superfamily, member 11 | 21943 | 8.0 | 2.1 |
| Pdk2: pyruvate dehydrogenase kinase, isoenzyme 2 | 18604 | 2.3 | 2.1 |
| Dgkz: diacylglycerol kinase zeta | 104418 | 2.3 | 2.0 |
| Nrn1: neuritin 1 | 68404 | 40.0 | 2.0 |
| Mtss1: metastasis suppressor 1 | 211401 | 3.8 | 2.0 |
| Bach2: BTB and CNC homology 2 | 12014 | 3.4 | 2.0 |
| 2310051E17Rik /// Klf3: Kruppel-like factor 3 /// RIKEN cDNA 2310051E17 gene | 16601 /// 70273 | 2.8 | 1.9 |
| Rai14: retinoic acid induced 14 | 75646 | 3.5 | 1.9 |
| Cd74: CD74 antigen (invariant polypeptide of major histocompatibility complex, class II antigen-associated) | 16149 | 2.9 | 1.9 |
| Lag3: lymphocyte-activation gene 3 | 16768 | 7.6 | 1.8 |
| Ptgfrn: prostaglandin F2 receptor negative regulator | 19221 | 2.5 | 1.8 |
| Slc17a6: solute carrier family 17 (sodium-dependent inorganic phosphate cotransporter), member 6 | 140919 | 6.7 | 1.8 |
| Trpm4: transient receptor potential cation channel, subfamily M, member 4 | 68857 | 4.4 | 1.8 |
| E130308A19Rik: RIKEN cDNA E130308A19 gene | 230259 | 6.1 | 1.8 |
| Ndrg1: N-myc downstream regulated gene 1 | 17988 | 12.6 | 1.7 |
| Ece1: endothelin converting enzyme 1 | 230857 | 2.3 | 1.7 |
| Exph5: exophilin 5 | 320051 | 4.5 | 1.7 |
| Jazf1: JAZF zinc finger 1 | 231986 | 2.4 | 1.7 |
| Olr1: oxidized low density lipoprotein (lectin-like) receptor 1 | 108078 | 10.6 | 1.7 |
| Ddx11: DEAD/H (Asp-Glu-Ala-Asp/His) box polypeptide 11 (CHL1-like helicase homolog, S. cerevisiae) | 320209 | 2.2 | 1.6 |
| Nalf: nasal embryonic LHRH factor | 56876 | 3.2 | 1.6 |
| Tspan5: tetraspanin 5 | 56224 | 2.4 | 1.6 |
| Repin1: replication initiator 1 | 58887 | 2.5 | 1.6 |
| Ttc3: tetratricopeptide repeat domain 3 | 22129 | 2.2 | 1.6 |
| Arl5: ADP-ribosylation factor-like 3 | 56350 | 3.0 | 1.6 |
| Ak3l1 /// LOC100047616: adenylate kinase 3 alpha-like 1 /// similar to adenylate kinase 4 | 100047616 /// 11639 | 5.5 | 1.5 |
| 9530058B02Rik: RIKEN cDNA 9530058B02 gene | 68241 | 3.1 | 1.5 |
| 2600010E01Rik: RIKEN cDNA 2600010E01 gene | 72446 | 4.0 | 1.5 |
| Slc13a3: solute carrier family 13 (sodium-dependent dicarboxylate transporter), member 3 | 114644 | 2.8 | 1.5 |

FIG. 14

METHODS AND COMPOSITIONS RELATED TO T-CELL ACTIVITY

CROSS-REFERENCE TO RELATED APPLICATIONS

This application is a continuation of U.S. patent application Ser. No. 15/937,044 filed Mar. 27, 2018, which is a continuation of U.S. Pat. No. 9,944,992 filed Sep. 15, 2015, which is a national phase application under 35 U.S.C. § 371 of International Application No. PCT/US2014/029173 filed Mar. 14, 2014, which claims the benefit of priority to U.S. Provisional Patent Application Ser. No. 61/794,535 filed Mar. 15, 2013. The entire contents of each of the above-referenced disclosures are specifically incorporated herein by reference without disclaimer.

GOVERNMENTAL RIGHTS

The invention was made with government support under Grant Nos. R01 CA161005, R01 AI080745, and R21 AI79373 awarded by the National Institutes of Health. The government has certain rights in the invention

BACKGROUND OF THE INVENTION

1. Field of the Invention

The present invention relates generally to the field of medicine. More particularly, it concerns the EGR2 transcriptome and targets that are used to diagnose or modified to treat T cell anergy and cancer.

2. Background

T cell anergy is a hyporesponsive state induced by TCR engagement in the absence of costimulation (Schwartz, 2003). Anergy induction was initially observed in vitro using chemically-fixed antigen presenting cells (APCs). Subsequently, it was found that anergy could be induced by immobilized anti-CD3 mAb or calcium ionophores (such as ionomycin) in vitro, and by superantigen and soluble antigenic peptide in vivo. Indirect evidence has suggested that T cell dysfunction in the tumor microenvironment and establishment of transplant tolerance is partially due to T cell anergy (Gajewski et al., 2011). T cell anergy is mainly characterized by the non-responsive state and multiple TCR signaling defects, of which, blunted Ras/MAPK activation has been consistently observed both in vitro and in vivo anergy models (Zheng et al., 2008). Further studies elucidated that the TCR signaling defects are due to presence of so called "anergy-associated factors", which are specifically synthesized upon anergy induction. Several anergy-associated factors have been identified, including diacylglycerol kinase-α and -ζ (DGK-α and DGK-ζ); the E3 ubiquitin ligases Cbl-b, GRAIL, and Itch; Deltex 1 (Dtx1); and the anti-proliferative protein Tob1. In particular, the inventors and others have demonstrated that DGK-α and DGK-ζ attenuate Ras/MAPK signaling by depleting diacylglycerol (DAG) (Olenchock et al., 2006; Zha et al., 2006).

The mechanisms leading to the generation of the anergy-associated factors have been gradually understood. TCR engagement alone activates the calcium/calcineurin/NFAT pathway out of proportion to AP1 activation, resulting in the upregulation of early growth response gene 2 and 3 (Egr2 and Egr3). Egr2 and Egr3 are transcriptional factors containing zinc finger domains (Chavrier et al., 1988; Patwardhan et al., 1991). The inventors and others have conducted gene-array analyses comparing anergic versus non-anergic T cells, and found that Egr2 is highly upregulated 2-3 hours after anti-CD3 treatment, which is reduced by calcineurin inhibitor cyclosporine A (Harris et al., 2004; Safford et al., 2005; Zha et al., 2006). The expression of Egr2 in anergic cells was of interest because the promoter region of the DGK-α gene contained an Egr2 binding site (Zheng et al., 2012). Forced-expression of Egr2 has been reported to suppress T cell activation as demonstrated by diminished IL-2 production and proliferation (Harris et al., 2004; Safford et al., 2005). Conversely, Egr2-deleted T cells are largely resistant to anti-CD3-induced anergy in vitro with restored IL-2 production and Erk phosphorylation (Zheng et al., 2012). Similar findings were observed in superantigen staphylococcal enterotoxin B (SEB)-induced anergy in vivo as well. Furthermore, conditional Egr2-deficient mice demonstrated enhanced anti-tumor immunity. The necessity of Egr2 in T cell anergy is partially due to its involvement in the regulation of most identified anergy-associated genes. ChIP assays and qRT-PCR confirmed that Egr2 interacts with and directly promotes the transcription of DGK-α, DGK-ζ, Cbl-b, Itch, Dtx1, and Tob1 in anergic cells.

Despite these advances in T cell anergy, knowledge about the anergic phenotype remains incomplete for several reasons. First, surface markers that might be used to identify anergic T cells are lacking. Second, it has been unclear teleologically why T cells being subjected to anergy-inducing conditions are not simply deleted from the repertoire, in order to eliminate T cells of undesired specificities. Therefore, there remains a need to understand how T cell anergy is implemented, particularly as it relates to understanding how some tumors may be less susceptible than others to respond to immunotherapy.

SUMMARY OF THE INVENTION

Methods and compositions are provided for identifying T cell anergy and treating a patient depending on whether T cells are anergic.

In certain aspects, methods are provided that involve a subject or a patient including, for example, the following: methods for evaluating T-cell anergy in a patient, methods for treating a patient with an immunotherapy, methods for evaluating an immune response, or methods for promoting a T-cell response in a subject. In any such methods, the subject or patient may be any subject or patient in need of such evaluation, treatment, or modulation of a cellular response. For example, the subject or patient may be a cancer subject or cancer patient. In other aspects, the subject or patient is a subject or patient having a chronic viral infection (e.g., HIV, hepatitis C, and the like). Moreover, a subject or patient may be a mammal, including a human.

In certain aspects, the disclosed methods and compositions are directed to nucleic acid molecules, such as those that reduce the expression or activity of a gene including, for example, the T-cell anergy genes listed in Table 2. However, it will be appreciated by one of ordinary skill in the art that such methods or compositions may alternatively target the product of the particular gene of interest. Thus, in any of the disclosed methods and compositions, it is contemplated that the product of a gene of interest may be modulated by using a molecule that specifically targets or binds to a polypeptide or protein product of the gene of interest (such as one or more of the genes listed in Table 2). Examples of such molecules that target gene products include, but are not limited to, polypeptides, antibodies, antibody fragments, aptamers, or small molecules.

Certain embodiments are directed to T-cell anergic genes, such as those listed in Table 2. Any such embodiments directed to T-cell anergic genes may involve one or more of the genes included Table 2, or may alternatively involve one or more of the genes included in the table provided in FIG. 14.

In certain embodiments, there are method for evaluating T-cell anergy in a patient comprising: a) measuring in T-cells from the patient an increase in expression level(s) of one or more T-cell anergic genes in Table 2 compared to a reference or control level of expression in non-anergic T-cells; and, b) identifying the patient as having anergic T-cells.

In further embodiments, there are methods for evaluating T-cell anergy in a patient is provided, the method comprising: measuring in T-cells from the patient expression level(s) of one or more T-cell anergic genes in Table 1; b) comparing the level to a reference or control level of expression T-cells identified as anergic; and c) identifying the patient as having anergic T-cells if the T-cells are determined to have an expression level that is decreased or less than about two-fold increased expression compared to a reference or control level of expression in the T-cells identified as anergic.

Also provided are methods for evaluating T-cell anergy in a patient comprising: a) measuring in T-cells from the patient an increase in expression level(s) of one or more T-cell anergic genes in Table 2 compared to a reference or control level of expression in non-anergic T-cells; and, b) identifying the patient as having anergic T-cells—wherein measuring an increase in expression comprises measuring an increase in protein expression.

In some embodiments, at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 genes in Table 2 (or any range derivable therein) have at least about or at most about a two-, three-, four-, five-, 6-, 7-, 8-, 9-, 10-, 12-, 15-, 20-, 25-, 30-, 35-, 40-, 45-, 50-, 60-, 70-, 80-, 90-, 100-fold increase in expression (or any range derivable therein) as compared to a reference or control level. In some aspects, the increase in expression is at about a five-fold increase. In further aspects, the T-cell anergic genes that are measured include a cytokine; or the T-cell anergic genes that are measured include a cell surface receptor (which may include, in some embodiments, wherein the cell surface receptor is Semaphorin 7A, Class-I-MHC-restricted T cell associated molecule (Crtam), lymphocyte-activation gene 3 (Lag3), 4-1BB and/or Nrn1); or the T-cell anergic genes that are measured include an intracellular protein (which may include, in some embodiments, wherein the intracellular protein is Bim, Nrgn, and/or Crabp2). In further aspects, any of the above methods for evaluating T-cell anergy in a patient may further comprise isolating T-cells from the patient (which may include, in some embodiments, wherein T-cells are isolated from a blood sample or a tumor or cancer sample from the patient—with the understanding that a cancer sample includes cancer cells or cells suspected of being cancerous). In further aspects, any of the above methods for evaluating T-cell anergy in a patient may further comprise obtaining a blood sample or a tumor or cancer sample from the patient. In further aspects, any of the above methods for evaluating T-cell anergy in a patient may be wherein: measuring an increase in expression comprises measuring an increase in RNA expression (which may be, for some embodiments, wherein an increase in RNA expression is measured comprising employing a hybridization and/or amplification assay). In additional aspects, any of the above methods for evaluating T-cell anergy in a patient may be wherein measuring an increase in expression comprises generating a cDNA of the mRNA transcript encoded by T-cell anergic gene. In related aspects, any of the above methods for evaluating T-cell anergy in a patient may further comprise amplifying cDNA corresponding to a T-cell anergic gene (which may be, for some embodiments, wherein amplifying cDNA comprises incubating the cDNA with one or more primer sets specific to the cDNA and performing polymerase chain reaction (PCR)).

In some aspects, the method for evaluating T-cell anergy in a patient may be wherein one or more binding proteins specific for a polypeptide encoded by a T-cell anergic gene is used (which may be, for some embodiments, wherein the one or more specific binding proteins comprise(s) all or part of an antibody specific for a polypeptide encoded by a T-cell anergic gene, where the method may or may not further comprise employing a quantitative immunoassay to measure protein expression). In related aspects, any of the above methods for evaluating T-cell anergy in a patient may be wherein expression is measured using an array or microarray.

In some embodiments of above methods, method for evaluating T-cell anergy in a patient is provided, the method comprising: measuring in T-cells from the patient expression level(s) of one or more T-cell anergic genes in Table 1; b) comparing the level to a reference or control level of expression T-cells identified as anergic; and c) identifying the patient as having anergic T-cells if the T-cells are determined to have an expression level that is decreased or less than about two-fold increased expression compared to a reference or control level of expression in the T-cells identified as anergic—is wherein measuring an increase in expression comprises measuring an increase in protein expression (which may be, for some embodiments, wherein: one or more binding proteins specific for a polypeptide encoded by a T-cell anergic gene is used; and/or the one or more specific binding proteins comprises all or part of an antibody specific for a polypeptide encoded by a T-cell anergic gene, and/or further comprises employing a quantitative immunoassay to measure protein expression). In some aspects, an above method may be wherein expression is measured using an array or microarray. It is contemplated that a measured level and a reference or control level of the T-cell anergy gene may be normalized. In some embodiments, the expression level of a particular gene may be used for both the measured level and the control or reference level, though they need not be.

In some embodiments, a method for treating a patient with immunotherapy is provided, the method comprising administering immunotherapy to the patient after the patient is identified as having non-anergic T-cells. In some aspects, this method may be wherein: the patient is identified as having non-anergic T-cells by measuring increased expression level(s) of one or more T-cell anergic genes in Table 2 compared to the expression level to a reference or control level of expression in non-anergic T-cells; or the patient is identified as having non-anergic T-cells by measuring expression level(s) of one or more T-cell anergic genes in Table 2 and comparing the expression level to a reference or control level of expression in anergic T-cells. In related aspects, an above method may be wherein: the immunotherapy comprises a cell-based immunotherapy; the immunotherapy may comprise antibody therapy, a vaccine (such as a cancer vaccine), a checkpoint inhibitor, cytokine IL-2, or an adoptive T cell therapy.

In further embodiments, a method for treating a patient is provided, the method comprising administering to the patient a composition comprising T-cell anergy suppressor, wherein the T-cell anergy suppressor reduces the expression or activity of a T-cell anergy gene listed in Table 2. In some additional aspects, this method is wherein the T-cell anergy suppressor is an antisense nucleic acid molecule targeted to a T-cell anergy gene listed in Table 2.

In further embodiments, there are methods for promoting a T-cell response in a subject comprising administering to the subject an effective amount of a composition comprising T-cell anergy suppressor, wherein the T-cell anergy suppressor reduces the expression or activity of a T-cell anergy gene listed in Table 2. Such a T-cell anergy suppressor may be a small molecule inhibitor, an antibody, or the other like therapeutic that can, for example, manipulate a particular gene product. In a related aspect, the method may further comprise administering to the subject one or more antigens, and may or may not be wherein the one or more antigens is in the same composition as the T-cell anergy suppressor. In a further related aspect, the T-cell anergy suppressor reduces expression of a T-cell anergy gene (which may be, in some embodiments, wherein the T-cell anergy suppressor is an antisense nucleic acid molecule targeted to a T-cell anergy gene listed in Table 2 and may or may not be wherein the composition comprises multiple antisense nucleic acid molecules targeted to the same or different genes listed in Table 2).

In particular embodiments, the subject or patient is suspected of having cancer and/or has symptoms of cancer. Alternatively, the patient may be deemed to be at risk for cancer (patient history, family history, or other risk factor(s)), at risk for metastasis, or at risk for recurrence. In other embodiments, the patient has been diagnosed with cancer or pre-cancer. In other embodiments, the subject or patient has a different disease or condition, but that may involve a T-cell response, in particular where promotion of a T cell response may have some therapeutic benefit.

In some embodiments there is an array, microarray, or chip comprising one or more nucleic acid probes for each of at least 5 T-cell anergic genes in Table 2. In some embodiments, the array, microarray or chip comprises one or more nucleic acid probes for each of at least 10, or for each at least 20, T-cell anergic genes in Table 2.

In related embodiments, a kit is provided, the kit comprising one or more nucleic acid probes for each of at least 5, or for each of at least 10, T-cell anergic genes in Table 2 and one or more reagents for detecting expression of the T-cell anergic gene. In related aspects, the kit may be wherein the nucleic acid probes are located on an array, microarray, or chip. Kits are also provided wherein protein or polypeptide products of genes are targeted, such as by antibodies, immunohistochemistry, or flow cytometry. In certain embodiments, a kit comprises one or more molecules that target at least 5 or at least 10 products of the T-cell anergic genes in Table 2. Examples of such molecules that may be used to target products of T-cell anergic genes include, but are not limited to, antibodies, antibody fragments, aptamers, or small molecules.

Methods may further involve calculating a risk score for the biological sample that characterizes or qualifies the anergy level of the patient's T-cells. The levels may be qualified into percentiles, such as quartiles or deciles.

The weight of a the expression level (or the value of that expression level) of a particular T-cell anergy gene reflects its importance in the accuracy, specificity, integrity, or other parameter relating to quality, of the test. This can be implemented in the algorithm or reflected in a model coefficient. A person of ordinary skill in the art would know how to determine this based on the experimental data. In certain embodiments, weighing a value more heavily may involve adding or multiplying the value by a particular number such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, or any range derivable therein.

In some embodiments, methods include evaluating a plurality of expression level values using a scoring algorithm to generate a diagnostic or risk score for having (or not having) anergic T-cells, wherein the patient is identified as having or as not having such a based on the score. It is understood by those of skill in the art that the score is a predictive value about whether the patient does or does not have T cells that are anergic. In some embodiments, the absence or paucity of infiltrating T cells in a tumor and the level of expression of one or more T-cell anergy genes may be a characteristic consistent with T-cell anergy. In some embodiments, a report is generated and/or provided that identifies the diagnostic score or the values that factor into such a score. In some embodiments, a cut-off score is employed to characterize a sample as likely having anergic T-cells (or alternatively not having anergic T-cells). In some embodiments, the risk score for the patient is compared to a cut-off score to characterize the biological sample from the patient with respect to whether they are likely to respond to immunotherapy.

In certain embodiments, T-cell anergy may be characterized as having increased expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 genes in Table 2 (or any range derivable therein) have at least about or at most about a two-, three-, four-, five-, 6-, 7-, 8-, 9-, 10-, 12-, 15-, 20-, 25-, 30-, 35-, 40-, 45-, 50-, 60-, 70-, 80-, 90-, 100-fold increase in expression (or any range derivable therein) as compared to a reference or control level. In a general sense, "anergy" refers to the inability of an immune cell to mount a complete response against its target.

In some embodiments, a tangible computer-readable medium is provided, the tangible computer-readable medium comprising computer-readable code that, when executed by a computer, causes the computer to perform operations comprising: a) receiving information corresponding to a level of gene expression in a T-cell sample from a patient comprising one or more T-cell anergy genes in Table 2; and b) calculating a risk score for the sample that identifies the sample as containing anergic T-cells. In further embodiments, a tangible computer-readable medium is provided, the a tangible computer-readable medium comprising computer-readable code that, when executed by a computer, causes the computer to perform operations comprising: a) receiving information corresponding to a level of gene expression in a T-cell sample from a patient comprising one or more T-cell anergy genes in Table 2; and b) calculating a risk score for the sample that identifies the sample as containing T-cells that are not anergic. In related aspects, any of the tangible computer-readable media may be wherein calculating a risk score comprises using a computer and an algorithm.

In some embodiments, a method that comprises administration of antibody therapy for treating a subject with an anergic T-cell associated disease, condition or pathology, is provided. In certain aspects, the anergic T-cell associated disease is cancer. In other aspects, the anergic T-cell associated disease, condition or pathology is metaplasia, dysplasia, hyperplasia or neoplasia. In certain aspects neoplasia can be classified as benign, pre-malignant or malignant.

In some embodiments a method of treating a subject with an anergic T-cell associated disease, condition or pathology, comprises administering a binding polypeptide that specifically recognizes and binds a substance, such as another polypeptide. In certain embodiments, the binding polypeptide is an antibody or a binding fragment of an antibody. In particular embodiments, the binding polypeptide comprises at least 1, 2, 3, 4, 5, or 6 CDRs from a monoclonal antibody. In certain embodiments, the method comprises an antibody therapy that comprises monoclonal antibodies. In yet other aspects the antibody therapy comprises isolated monoclonal antibodies. In some embodiments an antibody that is part of the antibody therapy binds a T-cell anergy gene product of at least one of the T-cell anergy genes listed in Table 2. In yet other embodiments the antibody binds a cell-surface receptor that is the product of at least one of the T-cell anergy genes listed in Table 2. In still other embodiments, the antibody therapy comprises at least one antibody that binds Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In specific embodiments, the antibody therapy comprises at least two antibodies that bind different cell surface receptors selected from the T-cell anergy genes of Table 2. In additional embodiments, the antibody therapy comprises at least three, four or five antibodies that bind different cell surface receptors selected from the T-cell anergy genes of Table 2. In one specific embodiment, the antibody therapy comprises a monoclonal antibody that binds lymphocyte-activation gene 3 (Lag3). In certain embodiments the anti-Lag3 antibody is monoclonal clone C9B7W. In certain embodiments the anti-Lag-3 antibody is BMS-986016. In certain embodiments the anti-Lag-3 antibody is any antibody in Table 3A or Table 3B or any antibody comprising the CDRs (e.g., a fully human, humanized or chimeric antibody) of an anti-Lag3 antibody of Table 3A or Table 3B. In another specific embodiment, the antibody therapy comprises a monoclonal antibody that binds 4-1BB (also known as tumor necrosis factor receptor superfamily member 9 (Tnfrsf9)). In yet other aspects, the anti-4-1BB antibody is monoclonal antibody clone LOB12.3. In yet other aspects, the anti-4-1BB antibody is monoclonal antibody BMS-663513, also known as urelumab. In certain embodiments the anti-anti-4-1BB antibody is any antibody in Table 4A or Table 4B or any antibody comprising the CDRs (e.g., a fully human, humanized or chimeric antibody) of an anti-4-1BB antibody of Table 4A or Table 4B. In still other embodiments, the antibody therapy comprises a monoclonal antibody that binds Lag3 and a monoclonal antibody that binds 4-1BB. In yet other embodiments, antibody therapy may be administered in combination with other treatments contemplated herein to suppress the activity or expression of T-cell anergy genes or their products.

In certain embodiments there is a method for treating a patient comprising administering to the patient a composition comprising a T-cell anergy suppressor, wherein the T-cell anergy suppressor is an antibody, binding fragment thereof, or binding polypeptide. In certain aspects, the antibody is a monoclonal antibody. In yet other aspects the composition comprises isolated monoclonal antibodies. In some embodiments an antibody that is present in the composition binds a T-cell anergy gene product of at least one of the T-cell anergy genes listed in Table 2. In yet other embodiments the antibody binds a cell-surface receptor that is the product of at least one of the T-cell anergy genes listed in Table 2. In still other embodiments, the composition comprises at least one antibody that binds Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In specific embodiments, the composition comprises at least two antibodies that bind different cell surface receptors selected from the T-cell anergy genes of Table 2. In additional embodiments, the composition comprises at least three, four or five antibodies that bind different cell surface receptors selected from the T-cell anergy genes of Table 2. In one specific embodiment, the composition comprises a monoclonal antibody that binds lymphocyte-activation gene 3 (Lag3). In certain embodiments the anti-Lag3 antibody is monoclonal clone C9B7W. In certain embodiments the anti-Lag-3 antibody is BMS-986016. In certain embodiments the anti-Lag-3 antibody is any antibody in Table 3A or Table 3B or any antibody comprising the CDRs (e.g., a fully human, humanized or chimeric antibody) of an anti-Lag3 antibody of Table 3A or Table 3B. In another specific embodiment, the composition comprises a monoclonal antibody that binds 4-1BB (also known as tumor necrosis factor receptor superfamily member 9 (Tnfrsf9)). In yet other aspects, the anti-4-1BB antibody is monoclonal antibody clone LOB12.3. In yet other aspects, the anti-4-1BB antibody is monoclonal antibody BMS-663513, also known as urelumab. In certain embodiments the anti-anti-4-1BB antibody is any antibody in Table 4A or Table 4B or any antibody comprising the CDRs (e.g., a fully human, humanized or chimeric antibody)

of an anti-4-1BB antibody of Table 4A or Table 4B. In still other embodiments, the composition comprises a monoclonal antibody that binds Lag3 and a monoclonal antibody that binds 4-1BB. In yet other embodiments, the composition may be administered in combination with other treatments contemplated herein to suppress the activity or expression of T-cell anergy genes or their products.

The T-cell anergy suppressor may be any polypeptide that specifically binds T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In certain embodiments, the binding polypeptide is a purified monoclonal antibody or a purified polyclonal antibody. The polypeptide may be, for example, an antibody that is single domain, humanized, or chimeric. In some embodiments, two or more binding polypeptides (e.g., two or more purified monoclonal antibodies or purified polyclonal antibodies) may be administered to the patient. In certain aspects, the binding polypeptide is recombinant. In other embodiments, there may be chemical modifications to the polypeptide, such as the addition of one or more chemical modifications or moieties.

Embodiments are provided in which the binding polypeptide comprises one or more CDR domains from an antibody that specifically binds to a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In particular embodiments, the binding polypeptide comprises one, two, three, four, five, six, or more CDR domains from among the VH or VL domain of the monoclonal antibodies listed in Table 3A, 3B, 4A or 4B. In certain aspects, the binding polypeptide comprises six CDR domains from among the VH or VL domains of the monoclonal antibodies listed in Table 3A, 3B, 4A or 4B. In some embodiments, the binding polypeptide comprises a sequence at least or at most 70%, 75%, 80%, 85%, 90%, 95%, or 99% (or any range derivable therein) identical to the VH or VL domain of the monoclonal antibodies listed in Table 3A, 3B, 4A or 4B. Embodiments are provided in which the binding polypeptide comprises the VH domain from the monoclonal antibodies listed in Table 3A, 3B, 4A or 4B and/or the VL domain of the monoclonal antibodies listed in Table 3A, 3B, 4A or 4B. In further embodiments, the monoclonal antibody is one or more monoclonal antibodies listed in Table 3A, 3B, 4A or 4B.

In some embodiments the binding polypeptide comprises one or more CDR domains from a binding polypeptide that specifically binds to a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) and a scaffold from a polypeptide selected from the group consisting of an immunoglobulin, a fibronectin or a S. aureus protein Z.

The binding polypeptide may be operatively coupled to a second binding polypeptide. In some aspects, the first and second binding peptides are operatively coupled recombinantly. In other aspects, the first and second binding peptides are operatively coupled chemically.

Embodiments are provided in which the binding polypeptide is administered at a dose of about, at least about, or at most about 0.1 mg/kg to 5 mg/kg, 1 mg/kg to 5 mg/kg, 0.1 mg/kg to 1 mg/kg, or 2 mg/kg to 5 mg/kg (or any range derivable therein).

Embodiments also provide a purified polypeptide comprising one or more binding polypeptide CDR domains from an antibody that specifically binds to a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In certain embodiments, the binding polypeptide competes for binding of a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) with the monoclonal antibodies listed in Table 3A, 3B, 4A or 4B. In certain aspects, the polypeptide has an association constant for a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) of between about 0.1 and 20 $nM^{-1}$, 0.5 and 10 $nM^{-1}$, or 1.0 and 10 nM-1 as measured by ELISA. The polypeptide may comprise, for example, a single domain antibody binding polypeptide, a humanized antibody, or a chimeric antibody.

In certain embodiments, the polypeptide is recombinant. In certain aspects, the recombinant polypeptide comprises at least 90%, 95%, or 99% of one or more CDR domains from the VH or VL domain of the monoclonal antibodies listed in Table 3A, 3B, 4A or 4B. In some embodiments, the recombinant polypeptide comprises two, three, four, five, six, or more CDR domains from the VH or VL domain of the monoclonal antibodies listed in Table 3A, 3B, 4A or 4B.

In some embodiments, a recombinant polypeptide comprises i) CDR1, CDR2, and/or CDR3 from the variable light chain of monoclonal antibodies listed in Table 3A, 3B, 4A or 4B; and/or ii) CDR1, CDR2, and/or CDR3 from the variable heavy chain of monoclonal antibodies listed in Table 3A, 3B, 4A or 4B. The sequences for these CDRs can be found in Table 3B and 4B.

In some embodiments, there is a purified polypeptide comprising one or more binding polypeptide CDR domains from an antibody that specifically binds to a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). As indicated above, the polypeptide may comprise 1, 2, 3, 4, 5, or 6 CDRs from the light and/or heavy chain variable regions of an antibody. Table 3B and 4B provide different T-cell anergy related cell surface receptor antibodies and their CDR1, CDR2, and CDR3 sequences from both the light and heavy chain variable regions. In certain embodiments, a polypeptide contains CDR1, CDR2, and/or CDR3 from the light chain variable region of a particular antibody. It is contemplated that while in some embodiments a polypeptide has a CDR1, CDR2, and CDR3 from the variable region of a light chain and/or the variable region of a heavy chain that the CDR1, CDR2, and CDR3 need not be from the same antibody. While some polypeptides have CDR1, CDR2, and CDR3 from the same antibody or based on the same antibody, given the overlap in amino acid sequences, a CDR1 from one antibody may be substituted with a CDR from or based on another antibody. It is generally contemplated, however, that when a single set of CDR1, CDR2, and CDR3 are employed together that they all be from a light chain variable region or from a heavy chain variable region, but not a mix from both.

Alternatively, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:63, 64, 65, 66, 67, 68, 100, or 110 which are CDR1 sequences from the light chain variable region of a T-cell anergy related cell surface receptor antibodies. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs: 69, 70, 71, 72, 73, 74, 101, 111, which are CDR2 sequences from the light chain variable region of T-cell anergy related cell surface receptor antibodies. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:75, 76, 77, 78, 79, 80, 102, or 112 which are CDR3 sequences from the light chain variable region of a T-cell anergy related cell surface receptor antibodies. Alternatively or additionally, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs: 45, 46, 47, 48, 49, 50, 95, or 105 which are CDR1 sequences from the heavy chain variable region of a T-cell anergy related cell surface receptor antibodies. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs: 51, 52, 53, 54, 55, 56, 96, or 106, which are CDR2 sequences from the heavy chain variable region of a T-cell anergy related cell surface receptor antibodies. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs: 57, 58, 59, 60, 61, 62, 97 or 107 which are CDR3 sequences from the heavy chain variable region of a T-cell anergy related cell surface receptor antibodies.

Other embodiments provide a recombinant polypeptide that comprises one or more CDR domain from an antibody that specifically binds to a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) and a scaffold from a polypeptide selected from the group consisting of an immunoglobulin, a fibronectin or a *S. aureus* protein Z. If it further contemplated that any polypeptide may be attached, fused or conjugated to an agent or substance, such a therapeutic moiety or a detectable moiety.

In other embodiments, the binding polypeptide is an antibody comprising (a) a heavy chain comprising said VH region, and a human hinge, CH1, CH2, and CH3 regions from an IgG1, IgG2, IgG3 or IgG4 subtype; and (b) a light chain comprising said VL region, and either a human kappa CL or human lambda CL.

Certain embodiments provide a purified monoclonal antibody that specifically binds to a a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1), wherein the purified monoclonal antibody is any monoclonal antibody listed in Table 3A, 3B, 4A or 4B.

In some aspects, the purified polypeptide does not consist of monoclonal antibodies listed in Table 3A, 3B, 4A or 4B. In other embodiments the purified polypeptide is not an isolated mouse monoclonal antibody.

Other embodiments provide a pharmaceutical composition comprising one or more purified binding polypeptides. In some embodiments, the pharmaceutical composition provides a single unit dose of the purified polypeptide in a sealed container. The pharmaceutical composition may comprise at least a second anti-cancer agent including, but not limited to, a chemotherapeutic, a cancer vaccine composition or a polypeptide that specifically binds to a second a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1).

Certain embodiments, provide a polynucleotide comprising a nucleic acid sequence encoding a binding polypeptide.

Other embodiments provide an expression vector comprising a nucleic acid sequence encoding a binding polypeptide operably linked to an expression control sequence. Some embodiments provide a host cell comprising the expression vector.

Embodiments also provide a method manufacturing a binding polypeptide comprising expressing a nucleic acid sequence encoding the polypeptide operably linked to an expression control sequence in a host cell.

Embodiments also provide for the use of antibodies in methods and compositions for the treatment of T-cell anergy related disease, pathology, condition, tumor or cancer. In certain embodiments, compositions are used in the manufacture of medicaments for the therapeutic and/or prophylactic treatment of T-cell anergy related disease, pathology, condition, tumor or cancer. Furthermore, in some embodiments there are methods and compositions that can be used to treat or prevent T-cell anergy related disease, pathology, condition, tumor or cancer.

Certain aspects are directed to methods of reducing, treating or ameliorating a T-cell anergy related disease, pathology, condition, tumor or cancer comprising administering to a patient having or suspected of having a T-cell anergy related disease, pathology, condition, tumor or cancer an effective amount of one or more purified antibodies that specifically bind a a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). The antibody can be a purified polyclonal antibody, a purified monoclonal antibody, a recombinant polypeptide, or a fragment thereof. In certain aspects the antibody is humanized or human. In still further aspects the antibody is a recombinant antibody segment. In certain aspects a monoclonal antibody includes one or more of the monoclonal antibodies listed in Table 3A, 3B, 4A or 4B. An antibody can be administered at a dose of 0.1, 0.5, 1, 5, 10, 50, 100 mg or μg/kg to 5, 10, 50, 100, 500 mg or μg/kg, or any range derivable therein. The recombinant antibody segment can be operatively coupled to a second recombinant antibody segment. In certain aspects the second recombinant antibody segment binds a second a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1. The method can further comprise administering a second antibody that binds a second a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). In certain aspects the method further comprises administering anti-cancer compound or composition.

Embodiments are directed to monoclonal antibody polypeptides, polypeptides having one or more segments thereof, and polynucleotides encoding the same. In certain aspects a polypeptide can comprise all or part of the heavy chain variable region and/or the light chain variable region of T-cell anergy related gene product antibodies. In a further aspect, a polypeptide can comprise an amino acid sequence that corresponds to a first, second, and/or third complementary determining regions (CDRs) from the light variable chain and/or heavy variable chain of a T-cell anergy related gene product antibody.

In still further aspects, embodiments provide a hybridoma cell line that produces a monoclonal antibody of the embodiments. In embodiments the hybridoma cell line is a line that produces the monoclonal antibodies listed in Table 3A, 3B, 4A or 4B. In a further aspect, 1, 2, and/or 3 CDRs from the light and/or heavy chain variable region of a MAb can be comprised in a humanized antibody or variant thereof.

Certain aspects are directed to methods of treating a subject having or suspected of having a T-cell anergy related disease, pathology, condition, tumor or cancer comprising administering to a patient having or suspected of having a T-cell anergy related disease, pathology, condition, tumor or cancer an effective amount of a purified antibody or polypeptide that specifically binds a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1).

In a further aspect methods are directed to treating a subject at risk of a T-cell anergy related disease, pathology, condition, tumor or cancer comprising administering to a patient at risk of a T-cell anergy related disease, pathology, condition, tumor or cancer an effective amount of an antibody that binds a T-cell anergy gene product from Table 2 or a T-cell anergy related cell surface receptor from Table 2 that includes Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) prior to development of a T-cell anergy related disease, pathology, condition, tumor or cancer.

Certain embodiments are directed to an antibody or binding polypeptide composition comprising an isolated and/or recombinant antibody or polypeptide that specifically binds a peptide segment as described above. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein.

In some embodiments, a method for treating a patient with immunotherapy is provided, the method comprising administering immunotherapy to the patient after the patient is identified as having anergic T-cells. In some aspects, this method may be wherein: the patient is identified as having anergic T-cells by measuring increased expression level(s) of one or more T-cell anergic genes in Table 2 compared to the expression level to a reference or control level of expression in non-anergic T-cells; or the patient is identified as having non-anergic T-cells by measuring expression level(s) of one or more T-cell anergic genes in Table 2 and comparing the expression level to a reference or control level of expression in anergic T-cells. In related aspects, an above method may be wherein: the immunotherapy comprises a cell-based immunotherapy; the immunotherapy may comprise antibody therapy, a vaccine (such as a cancer vaccine), a checkpoint inhibitor, cytokine IL-2, or an adoptive T-cell therapy.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 14-46 genes identified as targets of Egr2 by gene array×ChIP-SEQ in anergy.

FIG. 15—New Egr2-dependent anergy associated genes.

FIG. 16—PD1, Lag3 and Crtam are highly upregulated on CD8+ tumor-infiltrating lymphocytes (TILs) in the context of B16 melanoma.

FIG. 17—Lag3+Crtam+CD8+ TILs are defective in IL-2 production upon ex vivo stimulation.

FIG. 18—Lag3+Crtam+CD8+ TILs are hypoproliferative upon ex vivo stimulation.

FIG. 19—Anergy-associated genes are enriched in Lag3+ Crtam+ TILs.

FIG. 20—Conditional deletion of Eg2 in T cells leads to enhanced anti-tumor immune response and slowed tumor growth.

FIG. 21—B16.SIY tumor treatment with passive immunization of anti-4-1BB or anti-LAG-3 antibodies. Antibody treatments were on days 4, 7, 10 and 13 post-tumor cell inoculation. Antibody dose was 100 μg of each antibody, per mouse, per treatment.

DESCRIPTION OF ILLUSTRATIVE EMBODIMENTS

I. T Cell Anergy

Figures 1A, 1B, 1C:
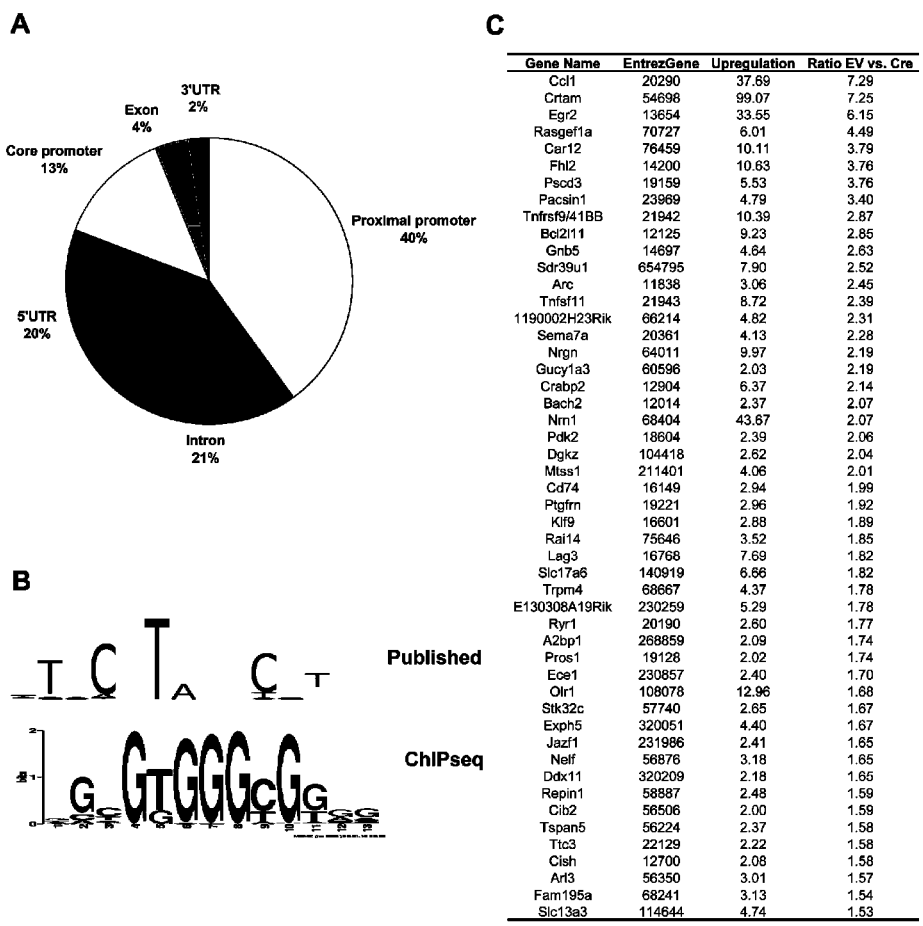
FIG. 1A-1C—Identification of direct targets of Egr2 in the context of T cell anergy by ChIP-seq and gene expression profiling analyses. CAR Tg×Egr2$^{flox/flox}$ Th1 T cells were anergized with immobilized anti-CD3, and Egr2-associated genes were identified by ChIP-seq analysis. (A) Distribution of the types of Egr2 binding sites in the genome. (B) Consensus sequence of Egr2 binding sites derived from ChIP-seq were highly similar to that published on TRANSFAC. EV- or Cre-transduced CAR Tg×Egr2$^{flox/flox}$ Th1 T cells were left untreated or anergized by immobilized anti-CD3 mAb, and anergy-associated and Egr2-dependent genes were determined by gene chip analysis. The results from ChIP-seq and gene chip analyses were merged to identify the direct targets of Egr2. (C) A list of direct Egr2 targets and their fold changes in expression upon anergy induction (Upregulation) and with Egr2 deletion (Ratio EV vs. Cre). The results were summarized from two independent ChIP-seq analyses and three independent gene expression profiling analyses.

Certain embodiments are directed to methods relating to the diagnosis or determination of T-cell anergy or T-cells in a hyporesponsive state. Other embodiments are directed to methods relating to therapeutic, prognostic, and diagnostic applications surrounding T-cell anergy, anergic T-cells and T-cells in a hyporesponsive state, such as those methods and compositions related to cancer.

In some embodiments, methods are directed to detecting the expression of genes associated with T-cell anergy or T-cell hyporesponsiveness. In other embodiments, methods are directed to the treatment or affecting the expression of genes involved in T-cell anergy or T-cell hyporesponsiveness. In certain embodiments, methods of diagnosing involve measuring the protein or nucleic acid expression of the spectrum of genes/gene products upregulated in an Egr2-dependent fashion. In other embodiments methods of treating involve affecting the expression of the spectrum of genes/gene products upregulated in an Egr2-dependent fashion.

II. Nucleic Acids

Nucleic acid molecules identical or complementary to all or part of any of the T cell anergy genes may be employed in diagnostic, prognostic and therapeutic methods and compositions described herein.

In the disclosed methods, nucleic acids can be labeled, used as probes, in array analysis, or employed in other diagnostic or prognostic applications, particularly those related to detecting T-cell anergy, T-cell pathological conditions and/or cancer. The expression of genes associated with T-cell anergy, a T-cell anergic condition or T-cell hyporesponsiveness may be assayed or detected by methods used to detect and/or measure nucleic acid expression described below.

In addition nucleic acids can be used as antisense or siRNA molecules targeted at a T cell anergy gene for use in reducing expression of that gene. In certain embodiments, reduction of expression provides inhibition of T cell anergy, and accordingly, induction of a T cell response. In the context of cancer, T cell infiltration of a tumor has benefits, and T cell anergy is contraindicated with T cell infiltration. These therapeutic nucleic acids may be modified to enhance their stability in storage or in vivo, bioavailability, activity, or localization.

The nucleic acids may have been endogenously produced by a cell, or been synthesized or produced chemically or recombinantly. They may be isolated and/or purified. Nucleic acids used in methods and compositions disclosed herein may have regions of identity or complementarity to another nucleic acid, such as a T cell anergy gene. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, or any range derivable therein, contiguous nucleotides. It is further understood that the length of complementarity within a gene, gene transcript or between a gene target and a nucleic acid are such lengths. Moreover, the complementarity may be expressed as a percentage, meaning that the complementarity between a probe and its target is 90% or greater over the length of the probe. In some embodiments, complementarity is or is at least 90%, 95% or 100%, or any range derivable therein. In particular, such lengths may be applied to any nucleic acid comprising a nucleic acid sequence identified. The commonly used name of the genes or gene targets is given throughout the application. Identification of gene sequence is provided by the Entrez gene number in the table in FIG. 1. This can be used to design the sequence of any probe, primer or siRNA molecule that is complementary or identical to a target T cell anergy gene identified herein.

It is understood that a nucleic acid may be derived from genomic sequences or a gene. In this respect, the term "gene" is used for simplicity to refer to the genomic sequence encoding the transcript for a given amino acid sequence. However, embodiments may involve genomic sequences of a gene that are involved in its expression, such as a promoter or other regulatory sequences.

The term "recombinant" generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, "hybridization", "hybridizes" or "capable of hybridizing" is understood to mean the forming of a double or triple stranded molecule or a molecule with partial double or triple stranded nature. The term "anneal" is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein, "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of such include hybridization performed at about 0.15 M to about 0.9 M NaCl at a temperature range of about 20° C. to about 50° C. Of course, it is within the skill of one in the art to further modify the low or high stringency conditions to suite a particular application.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods disclosed herein. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside, and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acid probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake, and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

A. Modified Nucleotides

Labeling methods and kits may use nucleotides that are both modified for attachment of a label and can be incorporated into a nucleic acid molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the methods and compositions are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the nucleic acid molecule or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in some embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, etc. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides are used in some embodiments. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Moreover, nucleic acid molecules may be modified through covalent bonding, attachment, fusion, or conjugation to or with one or more compounds. Examples of modifications include those identified in U.S. Patent Publications 20050261218 and 20090286969, which are hereby incorporated by reference. One or more modifications may be at the 5' end, the 3' end, on both, as well as on one or moth strands of a double-stranded molecule. In some embodiments, the modification is on the strand that is the antisense strand relative to the targeted transcript, or it may be on the complementary strand to the antisense strand. Modifications may be to the sugar molecule or to the backbone of the nucleic acid residue.

In some embodiments, nucleic acid molecules comprise at least 50%, at least 60%, at least 70%, at least 75%, at least 80%, or at least 85% sequence complementarity to a target region within the target nucleic acid. In other embodiments, the molecules comprise at least 90% sequence complementarity to a target region within the target nucleic acid. In other embodiments, the molecules comprise at least 95% or at least 99% sequence complementarity to a target region within the target nucleic acid. For example, a nucleic acid molecule in which 18 of 20 nucleobases of it are complementary to a target sequence would represent 90 percent complementarity. In this example, the remaining non-complementary nucleobases may be clustered or interspersed with complementary nucleobases and need not be contiguous to each other or to complementary nucleobases. As such, an oligomeric compound that is 18 nucleobases in length having 4 noncomplementary nucleobases that are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656).

A nucleic acid molecule is "targeted" to a molecule (that is a nucleic acid) in some embodiments. This means there is sufficient sequence complementarity to achieve a level of hybridization that accomplishes a particular goal with respect to the nucleic acid molecule, such as in the context of being a probe, a primer or an siRNA. In some embodiments, expression or function is to be modulated. This targeted nucleic acid (or nucleic acid or gene target) may be, for example, a mRNA transcribed from a cellular gene whose expression is associated with a particular disorder or disease state, a small non-coding RNA or its precursor, or a nucleic acid molecule from an infectious agent.

The targeting process usually also includes determination of at least one target region, segment, or site within the target nucleic acid for the interaction to occur such that the desired effect, e.g., modulation of levels, expression or function, will result. Within the context of the present invention, the term "region" is defined as a portion of the target nucleic acid having at least one identifiable sequence, structure, function, or characteristic. Within regions of target nucleic acids are segments. "Segments" are defined as smaller or sub-portions of regions within a target nucleic acid. "Sites," as used in the present invention, are defined as specific positions within a target nucleic acid. The terms region, segment, and site can also be used to describe an oligomeric compound of the invention such as for example a gapped oligomeric compound having three separate segments.

Targets of the nucleic acid molecules described in embodiments include both coding and non-coding nucleic acid sequences. For coding nucleic acid sequences, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

B. Preparation of Nucleic Acids

A nucleic acid may be made by any technique known to one of ordinary skill in the art, such as for example, chemical synthesis, enzymatic production, or biological production. It is specifically contemplated that nucleic acid probes are chemically synthesized.

In some embodiments, nucleic acids are recovered or isolated from a biological sample. The nucleic acids may be recombinant or it may be natural or endogenous to the cell (produced from the cell's genome). It is contemplated that a biological sample may be treated in a way so as to enhance the recovery of small RNA molecules such as mRNA or miRNAs. U.S. patent application Ser. No. 10/667,126 describes such methods and is specifically incorporated herein by reference. Generally, methods involve lysing cells with a solution having guanidinium and a detergent.

Alternatively, nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide) include a nucleic acid made by in vitro chemical synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In some methods, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide as described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method, polynucleotide phosphorylase method, and by solid-phase chemistry. The diester method was the first to be developed to a usable state, primarily by Khorana and co-workers. (Khorana, 1979). The basic step is the joining of two suitably protected deoxynucleotides to form a dideoxynucleotide containing a phosphodiester bond.

The main difference between the diester and triester methods is the presence in the latter of an extra protecting group on the phosphate atoms of the reactants and products (Itakura et al., 1975). Purifications are typically done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods draw on technology developed for the solid-phase synthesis of polypeptides. It has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become the most widely used coupling chemistry for the synthesis of oligonucleotides. Phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, nucleic acid molecules are not synthetic. In some embodiments, the nucleic acid molecule has a chemical structure of a naturally occurring nucleic acid and a sequence of a naturally occurring nucleic acid. In addition to the use of recombinant technology, such non-synthetic nucleic acids may be generated chemically, such as by employing technology used for creating oligonucleotides.

C. Isolation of Nucleic Acids

Nucleic acids may be isolated using techniques well known to those of skill in the art, though in particular embodiments, methods for isolating small nucleic acid molecules, and/or isolating mRNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If mRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating mRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased.

Methods may involve the use of organic solvents and/or alcohol to isolate nucleic acids, particularly RNA used in methods and compositions disclosed herein. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column may work particularly well for such isolation procedures.

In specific embodiments, RNA isolation processes include: a) lysing cells in the sample with a lysing solution comprising guanidinium, wherein a lysate with a concentration of at least about 1 M guanidinium is produced; b) extracting RNA molecules from the lysate with an extraction solution comprising phenol; c) adding to the lysate an alcohol solution for forming a lysate/alcohol mixture, wherein the concentration of alcohol in the mixture is between about 35% to about 70%; d) applying the lysate/alcohol mixture to a solid support; e) eluting the RNA molecules from the solid support with an ionic solution; and, f) capturing the RNA molecules. Typically the sample is dried down and resuspended in a liquid and volume appropriate for subsequent manipulation.

D. Labels and Labeling Techniques

In some embodiments, nucleic acids and/or nucleic acid probes are labeled. It is contemplated that nucleic acids may first be isolated and/or purified prior to labeling. This may achieve a reaction that more efficiently labels the nucleic acids, as opposed to other nucleic acids in a sample in which the nucleic acids is not isolated or purified prior to labeling. In particular embodiments, the label is non-radioactive. Generally, nucleic acids may be labeled by adding labeled nucleotides (one-step process) or adding nucleotides and labeling the added nucleotides (two-step process).

1. Labeling Techniques

In some embodiments, nucleic acids are labeled by catalytically adding to the nucleic acid an already labeled nucleotide or nucleotides. One or more labeled nucleotides can be added to nucleic acids molecules. See U.S. Pat. No. 6,723,509, which is hereby incorporated by reference.

In other embodiments, an unlabeled nucleotide(s) is catalytically added to nucleic acids, and the unlabeled nucleotide is modified with a chemical moiety that enables it to be subsequently labeled. In some embodiments, the chemical moiety is a reactive amine such that the nucleotide is an amine-modified nucleotide. Examples of amine-modified nucleotides are well known to those of skill in the art, many being commercially available.

In contrast to labeling of cDNA during its synthesis, the issue for labeling already synthesized nucleic acids is how to label the already existing molecule. Some aspects concern the use of an enzyme capable of using a di- or tri-phosphate ribonucleotide or deoxyribonucleotide as a substrate for its addition to nucleic acids. Moreover, in specific embodiments, a modified di- or tri-phosphate ribonucleotide is added to the 3' end of a nucleic acid. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments, a ligase is contemplated as not being the enzyme used to add the label, and instead, a non-ligase enzyme is employed.

Terminal transferase may catalyze the addition of nucleotides to the 3' terminus of a nucleic acid. Polynucleotide phosphorylase can polymerize nucleotide diphosphates without the need for a primer.

2. Labels

Labels on nucleic acids or nucleic acid probes may be colorimetric (includes visible and UV spectrum, including fluorescent), luminescent, enzymatic, or positron emitting (including radioactive). The label may be detected directly or indirectly. Radioactive labels include $I^{125}$, $P^{32}$, $P^{33}$, and $S^{31}$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides include Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides include Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, and Alexa Fluor 647-12-OBEA-dCTP.

It is contemplated that nucleic acids may be labeled with two different labels. Furthermore, fluorescence resonance energy transfer (FRET) may be employed in disclosed methods (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and other ligands, include ligands for an antibody.

E. Visualization Techniques

A number of techniques for visualizing or detecting labeled nucleic acids are readily available. Such techniques include, microscopy, arrays, fluorometry, light cyclers or other real time PCR machines, FACS analysis, scintillation counters, phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acids. Furthermore, a person of ordinary skill in the art is well aware of ways of visualizing, identifying, and characterizing labeled nucleic acids, and accordingly, such protocols may be used. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

F. Array Preparation and Screening

1. Array Preparation

Some embodiments involve the preparation and use of nucleic acid arrays or nucleic acid probe arrays, which are ordered macroarrays or microarrays of nucleic acid molecules (probes) that are fully or nearly complementary or identical to a plurality of nucleic acid molecules or precursor nucleic acid molecules and that are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of gene-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass, metal, plastic, and silicon. Such arrays may vary in a number of different ways, including average probe length, sequence or types of probes, nature of bond between the probe and the array surface, e.g. covalent or non-covalent, and the like. The labeling and screening methods are not limited by with respect to any parameter except that the probes detect nucleic acids; consequently, methods and compositions may be used with a variety of different types of nucleic acid arrays.

Representative methods and apparatuses for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000, which are each herein incorporated by reference.

It is contemplated that the arrays can be high density arrays, such that they contain 2, 20, 25, 50, 80, 100, or more, or any integer derivable therein, different probes. It is contemplated that they may contain 1000, 16,000, 65,000, 250,000 or 1,000,000 or more, or any integer or range derivable therein, different probes. The probes can be directed to targets in one or more different organisms or cell types. In some embodiments, the oligonucleotide probes may range from 5 to 50, 5 to 45, 10 to 40, 9 to 34, or 15 to 40 nucleotides in length. In certain embodiments, the oligonucleotide probes are 5, 10, 15, 20, 25, 30, 35, 40 nucleotides in length, including all integers and ranges there between.

Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed herein or may be found in, for example, WO 9743450; WO 03023058; WO 03022421; WO 03029485; WO 03067217; WO 03066906; WO 03076928; WO 03093810; WO 03100448A1, all of which are specifically incorporated by reference.

2. Sample Preparation

It is contemplated that the nucleic acids of a wide variety of samples can be analyzed using arrays, nucleic acid probes, or array technology. While endogenous nucleic acids are contemplated for use with compositions and methods disclosed herein, recombinant nucleic acids—including nucleic acids that are complementary or identical to endogenous nucleic acids—can also be handled and analyzed as described herein. Samples may be biological samples, in which case, they can be from biopsy, fine needle aspirates, exfoliates, blood, tissue, organs, semen, saliva, tears, other bodily fluid, hair follicles, skin, or any sample containing or constituting biological cells. In certain embodiments, samples may be, but are not limited to, fresh, frozen, fixed, formalin fixed, paraffin embedded, or formalin fixed and paraffin embedded. Alternatively, the sample may not be a biological sample, but a chemical mixture, such as a cell-free reaction mixture (which may contain one or more biological enzymes).

After an array or a set of nucleic acid probes is prepared and the nucleic acids in the sample are labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in embodiments is the use of stringent conditions during hybridization. Stringent conditions are known to those of skill in the art.

It is specifically contemplated that a single array or set of probes may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular nucleic acids corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 μl or less, including volumes of about or less than about 5, 10, 25, 50, 60, 70, 80, 90, 100 μl, or any range derivable therein). In small volumes, hybridization may proceed very rapidly.

3. Differential Expression Analyses

Arrays can be used to detect differences between two samples. Specifically contemplated applications include identifying and/or quantifying differences between nucleic acids or mRNA from a sample that is normal and from a sample that is not normal, between T-cell anergic and non T-cell anergic samples and/or a cancerous condition and a non-cancerous condition, or between two differently treated samples. Also, nucleic acids or mRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. These arrays may generally be produced using mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. No. 5,384,261, incorporated herein by reference in its entirety. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate (see U.S. Pat. Nos. 5,770,358, 5,789,162, 5,708,153, 6,040,193 and 5,800,992, each of which is hereby incorporated in its entirety). Arrays may be packaged in such a manner as to allow for diagnostics or other manipulation of an all inclusive device (see for example, U.S. Pat. Nos. 5,856,174 and 5,922,591, each incorporated in its entirety by reference). See also U.S. patent application Ser. No. 09/545,207, filed Apr. 7, 2000, which is incorporated by reference in its entirety for additional information concerning arrays, their manufacture, and their characteristics, Particularly, arrays can be used to evaluate samples with respect to diseases or conditions that include, but are not limited to: T-cell anergy, chronic pancreatitis; pancreatic cancer; AIDS, autoimmune diseases (rheumatoid arthritis, multiple sclerosis, diabetes-insulin-dependent and non-independent, systemic lupus erythematosus and Graves disease); cancer (e.g., malignant, benign, metastatic, precancer); cardiovascular diseases (heart disease or coronary artery disease, stroke-ischemic and hemorrhagic, and rheumatic heart disease); diseases of the nervous system; and infection by pathogenic microorganisms (Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis); inflammation (allergy, asthma); prion diseases (e.g., CJD, kuru, GSS, FFI).

Cancers that may be evaluated by the disclosed methods and compositions include cells and cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, T-cell anergy can be evaluated in precancers, such as metaplasia, dysplasia, and hyperplasia.

It is specifically contemplated that the disclosed methods and compositions can be used to evaluate differences between stages of disease, such as between hyperplasia, neoplasia, pre-cancer and cancer, or between a primary tumor and a metastasized tumor. A tumor sample or a cancer sample from a patient can include cancer cells or cells suspected of being cancerous.

Moreover, it is contemplated that samples that have differences in the activity of certain pathways may also be compared. These pathways include the following and those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, NFκ-B signaling, angiogenesis, adipogenesis, cell adhesion, viral infection, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 activation.

Cellular pathways that may be profiled also include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin; any apoptosis pathway including but not limited to those involving AKT, Fas ligand, NFkappaB, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p73, Rad51, Mdm2, Rad50, c-Abl, BRCA-1, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, H2O2, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, IκBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, IKKβ, NFκB, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKP1, the proteasome, CUL1, E2F, p107, steroid hormones, steroid hormone receptors, IκBα, IκBβ, Sin 3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKβ, NFκB, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that the disclosed nucleic acids molecules can be employed in diagnostic and therapeutic methods with respect to any of the above pathways or factors. Thus, in some embodiments, a T-cell anergy gene may be differentially expressed with respect to one or more of the above pathways or factors.

Phenotypic traits also include characteristics such as longevity, morbidity, appearance (e.g., baldness, obesity), strength, speed, endurance, fertility, susceptibility or receptivity to particular drugs or therapeutic treatments (drug efficacy), and risk of drug toxicity. Samples that differ in these phenotypic traits may also be evaluated using the arrays and methods described.

In certain embodiments, nucleic acid or mRNA profiles may be generated to evaluate and correlate those profiles with pharmacokinetics. For example, nucleic acid or mRNA profiles may be created and evaluated for patient tumor and blood samples prior to the patient being treated or during treatment to determine if there are nucleic acid or mRNAs whose expression correlates with the outcome of the patient. Identification of differential nucleic acid or mRNAs can lead to a diagnostic assay involving them that can be used to evaluate tumor and/or blood samples to determine what drug regimen the patient should be provided. In addition, identification of differential nucleic acid or mRNAs can be used to identify or select patients suitable for a particular clinical trial. If a nucleic acid or mRNA profile is determined to be correlated with drug efficacy or drug toxicity, such may be relevant to whether that patient is an appropriate patient for receiving a drug or for a particular dosage of a drug.

G. Nucleic Acid Amplification

Quantitative and semiquantive PCR. These amplification methods may be employed to evaluate, assay or measure T-cell anergy gene expression level. Semiquantitave PCR is used as described by (Murphy et al., 1993; Salvi et al., 1995). These amplification methods may involve primers or primer pairs that are complementary to the sequence to be detected.

H. Other Nucleic Acid Assays

In addition to the use of arrays and microarrays, it is contemplated that a number of different assays could be employed to analyze genes, expressed genes, genes that regulate or are regulated by the same, their activities, and their effects. Such assays include, but are not limited to, nucleic acid amplification, polymerase chain reaction, quantitative PCR, RT-PCR, in situ hybridization, Northern hybridization, hybridization protection assay (HPA), branched DNA (bDNA) assay, rolling circle amplification (RCA), single molecule hybridization detection, Invader assay, and/or Bridge Litigation Assay.

I. Immunoassays

As an alternative to, or in tandem with nucleic acid detection methods, isolated cells from patient samples or biopsies can be lysed and T-cell anergy gene protein levels can be determined by Western blotting methods with T-cell anergy gene specific antibodies. Antibodies of the present invention can be used in characterizing the T-cell anergy gene protein content of tissues or cells in bodily fluids such as blood, cerebrospinal fluid, urine, prostate fluid or semen through techniques such as RIAs, ELISAs and Western blotting.

Immunoassays can be classified according to the assay type, assay method and endpoint labeling method. These three major criteria for classification that have the greatest influence on the performance of test are, i) the use of a limited (type II) or excessive reagent format (type I), ii) the use of a homogeneous and heterogeneous format, iii) the use of a label or unlabeled assay format and the choice of label. It is contemplated that all these kinds of immunoassays may be employed.

In Type I assay format, where antigen binds to an excess of antibody, the most common method is sandwich assay. In this approach, the first antibody (capture Ab) in excess is coupled to a solid phase. The bound antigen is then detected with a second antibody (indicator Ab) labeled with various indicators such as enzymes, fluorophores, radioisotopes, particles, etc. In this assay, the amount of indicator antibody captured on the solid phase is directory proportional to the amount of antigen in the sample.

In some embodiments, an ELISA assay is particularly contemplated. For example, antibodies to T-cell anergy genes may be immobilized onto a selected surface, for example, a surface such as a microtiter well, a membrane, a filter, a bead or a dipstick. After washing to remove incompletely adsorbed material, it is desirable to bind or coat the surface with a non-specific agent that is known to be antigenically neutral with regard to the test sample, e.g., bovine serum albumin (BSA), casein or solutions of powdered milk. This allows for blocking of non-specific adsorption sites on the immobilizing surface and thus reduces the background caused by non-specific binding of antibody to antigen on the surface.

After binding of antibody to the surface and coating, the surface is exposed to lysed patient tumor sample, blood, blood plasma, blood serum, urine, prostate fluid or semen. Following formation of specific immunocomplexes between antigens in the blood and the antibody, and subsequent washing, the occurrence and even amount of immunocomplex formation may be determined by subjecting the same to a second antibody having specificity for the antigen. Appropriate conditions preferably include diluting the sample with diluents such as BSA, bovine gamma globulin (BGG) and phosphate buffered saline (PBS)/Tween. These added agents also tend to assist in the reduction of non-specific background. The detecting antibody is then allowed to incubate for from about 2 to about 4 hr, at temperatures preferably on the order of about 250 to about 27° C. Following incubation, the surface is washed so as to remove non-immunocomplexed material. A preferred washing procedure includes washing with a solution such as PBS/Tween or borate buffer.

To provide a detecting means, the second antibody may have an associated label, e.g., an enzyme that will generate a color development upon incubating with an appropriate chromogenic substrate. Thus, for example, one will desire to contact and incubate the second antibody for a period of time and under conditions which favor the development of immunocomplex formation (e.g., incubation for 2 hr at room temperature in a PBS-containing solution such as PBS/Tween®).

After incubation with the second antibody, and subsequent to washing to remove unbound material, the amount of label may be quantified (e.g., by incubation with a chromogenic substrate such as urea and bromocresol purple or 2,2'-azino-di-(3-ethyl-benzthiazoline)-6-sulfonic acid (ABTS) and hydrogen peroxide in the case of peroxidase as the enzyme label). Quantitation is then achieved by measuring the label, e.g., degree of color generation, e.g., using a visible spectrum spectrophotometer.

Other potential labels include radiolabels, fluorescent labels, dyes and chemiluminescent molecules (e.g., luciferase).

In Type II assay formats, a limited amount of antibody is used (insufficient to bind the entire antigen) a prefixed amount of labeled antigen competes with the unlabeled antigen in test sample for a limited number of antibody binding sites. The concentration of unlabeled antigen in specimen can be determined from the portion of labeled antigen that is bound to the antibody. Since most analyte molecules are not enough large to provide two different epitopes in this method, the response will be inversely proportional to the concentration of antigen in the unknown.

The use of either competitive or immunometric assays requires differentiation of bound from free label. This can be archived either by separating bound from free label using a means of removing antibody (heterogeneous) or modulation of signal of the label when antigen is bound to antibody compared to when it is free (homogeneous).

Most solid phase immunoassays belong to the Heterogeneous Assay category. There are many ways of separating bound from free label such as precipitation of antibody, chromatographic method, and solid phase coupling antibody. Homogeneous assays do not require any of separation step to distinguish antigen bound antibody from free antibody. It has an advantage in automation, and typically is faster, easier to perform, and more cost-effective, but its specificity and sensitivity are lower.

Contacting the chosen biological sample with the first antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any anti-T-cell anergy protein complex. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art. All prior assays to detect immunocomplexes are based on autologous complexes generated by the patient's own antibodies and antigen. The present invention is different in that the assays of the present invention detect immunocomplexes as a result of a therapeutic approach.

The antigen, antibody or antigen:antibody complex employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain useful immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies are immobilized on a selected surface, such as a well in a polystyrene microtiter plate, dipstick, or column support. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is known as a "sandwich ELISA". Detection also may be achieved by the addition of a second antibody specific for the desired antigen, followed by the addition of a third antibody that has binding affinity for the second antibody, with the third antibody being linked to a detectable label.

Variations on ELISA techniques are known to those of skill in the art. In one such variation, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions typically include diluting the antigens and antibodies with solutions such as BSA, bovine gamma globulin (BGG) and phosphate buffered saline (PBS)/TWEEN (polysorbate). These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures that may be on the order of 25° C. to 27° C., or may be overnight at about 4° C. or so.

After all incubation steps in an ELISA are followed, the contacted surface is washed so as to remove non-complexed material. Washing often includes washing with a solution of PBS/TWEEN®, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. In some embodiments, this will be an enzyme that will generate color development upon incubating with an appropriate chromogenic substrate. Thus, for example, one will desire to contact and incubate the first or second immune complex with a urease, glucose oxidase, alkaline phosphatase, or hydrogen peroxidase-conjugated antibody for a period of time and under conditions that favor the development of further immune complex formation, e.g., incubation for 2 hours at room temperature in a PBS-containing solution such as PBS-TWEEN™.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label.

Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605

It also is contemplated that the above reagents maybe packaged in a kit that may be produced commercially to measure the soluble antigens, antibodies or antibody:antigen complexes described herein.

J. Antibodies and Antibody-Like Molecules

In certain aspects, one or more antibodies or antibody-like molecules (e.g., polypeptides comprising antibody CDR domains) may be obtained or produced which have a specificity for a T-cell anergy gene product of Table 2 or a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')$_2$, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate binding molecules for a T-cell anergy gene product of Table 2 or a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as binding molecules for a T-cell anergy gene product of Table 2 or a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1). Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

1. Methods for Generating Antibodies

Methods for generating antibodies (e.g., monoclonal antibodies and/or monoclonal antibodies) are known in the art.

Briefly, a polyclonal antibody is prepared by immunizing an animal with a T-cell anergy gene product of Table 2 or a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography, among others.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

The animals are injected with antigen, generally as described above. The antigen may be mixed with adjuvant, such as Freund's complete or incomplete adjuvant. Booster administrations with the same antigen or DNA encoding the antigen may occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Generally, spleen cells are a rich source of antibody-producing cells that are in the dividing plasmablast stage. Typically, peripheral blood cells may be readily obtained, as peripheral blood is easily accessible.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al. (2002), for a discussion of myeloma expression systems.

One murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 7174, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

2. Antibody and Polypeptide Conjugates

Embodiments provide antibodies and antibody-like molecules against a T-cell anergy gene product of Table 2 or against a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) protein, polypeptide or peptide that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often used in certain embodiments, and technicium$^{99m}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or 1,3,4,6-tetrachloro-3a,6a-diphenylglycouril attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In some embodiments, antibodies against a T-cell anergy gene product of Table 2 or a T-cell anergy related cell surface receptor selected from Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1) are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays include, but are not limited to, those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

III. Therapeutic Methods

A. Therapeutic siRNA

Small interfering RNA (siRNA), sometimes known as short interfering RNA or silencing RNA, are double-stranded RNA molecules, 20-25 base pairs in length. siRNAs form part of the RNA interference (RNAi) pathway, where they interfere with the expression of specific genes with complementary nucleotide sequence. Any of the embodiments discussed above regarding nucleic acids may be implemented with respect to siRNA molecules.

Therapeutic siRNA may be administered to a patient to modulate the expression of one or more of the genes identified as involved in T-cell anergy. Therapeutic siRNA may also target the expression of the spectrum of genes/gene products upregulated in an Egr2-dependent fashion. The design of siRNA to target expression of a gene is a process well known in the art (Nat Biotechnol. 2004 March; 22(3): 326-30. Rational siRNA design for RNA interference. Reynolds A, Leake D, Boese Q, Scaringe S, Marshall W S, Khvorova A.). Design of siRNA to target any of the genes identified in T-cell anergy or T-cell hyporesponsiveness may be done using the sequences references by Entrez reference number of genes as listed in FIG. 1C.

The generation of siRNA molecules may, but is not limited to, methodology described in paragraphs above. In addition, the nucleic acid molecules described above may be employed as siRNA molecules targeting a T cell anergic gene.

Immunotherapy may be used in conjunction with siRNA methods described above. Immunotherapy approaches may include ex vivo and in vivo approaches to increase the immunogenicity of patient tumour cells, such as transfection with cytokines such as interleukins (such as interleukin 2 or interleukin 4), interferons (α, β, γ), or granulocyte macrophage colony stimulating factor. Immunotherapy approaches may also involve using transfected immune cells such as cytokine transfected dendritic cells or approaches using cytokine transfected tumour cell lines and using anti idiotypic antibodies.

Immunotherapy approaches may also include approaches to decrease the function of immune suppressive cells such as regulatory T cells, myeloid-derived suppressor cells or IDO (indoleamine 2,3,-deoxygenase)-expressing dendritic cells, and approaches using cancer vaccines consisting of proteins or peptides derived from tumour-associated antigens such as NY-ESO-1, MAGE-3, WT1 or Her2/neu.

Immunotherapy approaches may also target PD-1 and other molecules which signal through interactions with PD-1, such as programmed death ligand 1 (PD-L1) and programmed death ligand 2 (PD-L2). The inhibition of PD-L1 signaling can be used as immunotherapeutic means to enhance T cell immunity for the treatment of cancer (e.g., tumor immunity) and infection.

B. Antibody Therapy

In certain immunotherapy approaches, a binding polypeptide that specifically recognizes and binds a substance, such as another polypeptide may be administered to modulate the activity of one or more proteins involved in T-cell anergy. In certain instances, the binding polypeptide is an antibody or a binding fragment of an antibody. The binding polypeptide may comprises at least 1, 2, 3, 4, 5, or 6 CDRs from a monoclonal antibody. Certain types of immunotherapy may comprise antibody therapy that comprises monoclonal antibodies.

Immunotherapy comprising antibody therapy specifically contemplate an antibody that is part of the antibody therapy and binds a T-cell anergy gene product of at least one of the T-cell anergy genes listed in Table 2. In other specific immunotherapeutic methods the antibody binds a cell-surface receptor that is the product of at least one of the T-cell anergy genes listed in Table 2. Some examples include an antibody that binds Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, also known as 4-1BB), Neuritin (Nrn1), CLIP (CD74), Tnfsf11 (RANKL, CD254), prostaglandin F2 receptor inhibitor (Ptgfrn, CD9-P1, CD315) or oxidized low density lipoprotein receptor 1 (LOX1, OLR1).

Immunotherapy comprising antibody therapy may comprise at least one or at least two antibodies that bind different cell surface receptors selected from the T-cell anergy genes of Table 2. In additional embodiments, the antibody therapy comprises at least three, four or five antibodies that bind different cell surface receptors selected from the T-cell anergy genes of Table 2.

Antibody therapy can comprise a monoclonal antibody that binds lymphocyte-activation gene 3 (Lag3). A Lag3 antibody may be any of the Lag3 antibodies given below or any other Lag3 antibody known or commercially available. In certain embodiments the anti-Lag3 antibody is monoclonal clone C9B7W or any humanized or fully human antibody comprising the CDRs of C9B7W.

Antibody therapy can comprise a monoclonal antibody that binds 4-1BB (also known as tumor necrosis factor receptor superfamily member 9 (Tnfrsf9)). A 4-1BB antibody may be any of the 4-1BB antibodies given below or any other 4-1BB antibody known or commercially available. In certain aspects, the anti-4-1BB antibody is monoclonal antibody clone LOB12.3. In still other embodiments, the antibody therapy comprises a monoclonal antibody that binds Lag3 and a monoclonal antibody that binds 4-1BB. In yet other embodiments, antibody therapy may be administered in combination with other treatments contemplated herein to suppress the activity or expression of T-cell anergy genes or their products.

1. Lag3 Antibodies

A Lag3 antibody may be any of the Lag3 antibodies given in Table 3A below. Specifically, a Lag3 antibody may be any one of monoclonal 17B4, 11E3, 1D4B, BMS-986016 or C9B7W or any chimeric, humanized or fully human antibody comprising the CDRs of anti-Lag3 monoclonals 17B4, 11E3, 1D4B, BMS-986016 or C9B7W. In certain embodiments the anti-Lag3 antibody is monoclonal clone C9B7W. In some embodiments, 2, 3, 4, or more different Lag antibodies are used.

A Lag3 antibody may also be any of the Lag3 antibodies disclosed in WO2010/019570, incorporated herein by reference in its entirety. These Lag3 antibodies include anti-Lag3 (clone 251F7), anti-Lag3 (clone 261H10), anti-Lag3 (clone 25E3), anti-Lag3 (clone 8B7), anti-Lag3 (clone 111F2) and anti-Lag3 (clone 17E5). A Lag3 antibody may also be any chimeric, humanized or fully human antibody comprising the CDRs of anti-Lag3 (clone 251F7), anti-Lag3 (clone 261H10), anti-Lag3 (clone 25E3), anti-Lag3 (clone 8B7), anti-Lag3 (clone 111F2) and anti-Lag3 (clone 17E5). The CDRs and variable regions of these clones are as indicated in Table 3B below (VH=heavy chain variable region; VK=light chain variable region).

TABLE 3B

| Antibody | SEQ ID NO: | Description |
| --- | --- | --- |
| anti-Lag3 (25F7) | 45 | VH CDR1 |
| | 51 | VH CDR2 |
| | 57 | VH CDR3 |
| | 63 | VK CDR1 |
| | 69 | VK CDR2 |
| | 75 | VK CDR3 |
| | 81 | VH |
| | 87 | VK |
| anti-Lag3 (26H10) | 46 | VH CDR1 |
| | 52 | VH CDR2 |
| | 58 | VH CDR3 |
| | 64 | VK CDR1 |
| | 70 | VK CDR2 |
| | 76 | VK CDR3 |
| | 82 | VH |
| | 88 | VK |
| anti-Lag3 (25E3) | 47 | VH CDR1 |
| | 53 | VH CDR2 |
| | 59 | VH CDR3 |
| | 65 | VK CDR1 |
| | 71 | VK CDR2 |
| | 77 | VK CDR3 |
| | 83 | VH |
| | 89 | VK |
| anti-Lag3 (8B7) | 48 | VH CDR1 |
| | 54 | VH CDR2 |
| | 60 | VH CDR3 |
| | 66 | VK CDR1 |
| | 72 | VK CDR2 |
| | 78 | VK CDR3 |

TABLE 3A

| Lag3 antibody | specificity/type | Company Cat. No. | Company |
| --- | --- | --- | --- |
| LAG3 (clone 17B4) | human/mouse monoclonal | LS-B2237 | LifeSpan BioSciences, Inc. |
| LAG3 (clone 11E3) | human/mouse monoclonal | LS-C18690 | LifeSpan BioSciences, Inc. |
| LAG3 | mouse/rat monoclonal | LS-C4474 | LifeSpan BioSciences, Inc. |
| LAG3 (aa110-140) | human/rabbit polyclonal | LS-C165666 | LifeSpan BioSciences, Inc. |
| LAG3 (clone 11E3) | human/mouse monoclonal | LS-C18690 | LifeSpan BioSciences, Inc. |
| LAG3 (clone 1D4B) | mouse/rat monoclonal | LS-C189811 | LifeSpan BioSciences, Inc. |
| LAG3(clone C9B7W) | mouse/rat monoclonal | 14-2231-85 | affymetrix eBioscience |
| | Goat Polyclonal | FAB2319 | R&D |
| Clone 333210 | Mouse IgG2A | MAB2319 | R&D |
| Clone 333213 | Mouse IgG2A | MAB23192 | R&D |
| Clone 333221 | Mouse IgG2B | BAM23191 | R&D |
| Clone 874501 | Mouse IgG1 | MAB23193 | R&D |
| 3DS223H | Mouse IgG1 | 46-2239-41 | Ebioscience |
| Clone EPR4392(2) | Rabbit monoclonal | ab180187) | AbCam |
| Clone 11E3 | Mouse Monoclonal | (ab40465) | AbCam |

TABLE 3B-continued

| Antibody | SEQ ID NO: | Description |
|---|---|---|
| | 84 | VH |
| | 90 | VK |
| anti-Lag3 (11F2) | 49 | VH CDR1 |
| | 55 | VH CDR2 |
| | 61 | VH CDR3 |
| | 67 | VK CDR1 |
| | 73 | VK CDR2 |
| | 79 | VK CDR3 |
| | 85 | VH |
| | 91 | VK |
| anti-Lag3 (17E5) | 50 | VH CDR1 |
| | 56 | VH CDR2 |
| | 62 | VH CDR3 |
| | 68 | VK CDR1 |
| | 74 | VK CDR2 |
| | 80 | VK CDR3 |
| | 86 | VH |
| | 92 | VK |

2. 4-1BB Antibodies

A 4-1BB antibody may be any of the 4-1BB antibodies given in Table 4A below. Specifically, a 4-1BB antibody may be anyone of monoclonal LOB12.3, 4b4-1, ectodomain clone BBK-2, 515, BMS-663513 (also known as urelumab) or BBK-2 or any chimeric, humanized or fully human antibody comprising the CDRs of anti-4-1BB monoclonals LOB12.3, 4b4-1, ectodomain clone BBK-2, 5H5, BMS-663513 (also known as urelumab) or BBK-2.

TABLE 4A

| 4-1BB antibody | specificity/type | Company Cat. No. | Company |
|---|---|---|---|
| Anti-4-1BB clone 4b4-1 | human/mouse monoclonal | LS-C134760 | LifeSpan BioSciences, Inc. |
| Anti-4-1BB (ectodomain) clone BBK-2 | human/mouse monoclonal | LS-C88297 | LifeSpan BioSciences, Inc. |
| Anti-4-1BB | human/goat polyclonal | LS-C104311 | LifeSpan BioSciences, Inc. |
| Anti-4-1BB clone 5H5 | human/mouse monoclonal | LS-C175677 | LifeSpan BioSciences, Inc. |
| Anti-4-1BB clone BBK-2 | human/mouse monoclonal | LS-C88295 | LifeSpan BioSciences, Inc. |
| Anti-4-1BB Clone 4B4 | Mouse IgG1 | 12-1379-41 | Ebioscience/Many |
| Anti-4-1BB Clone h41BB-M127 | mouse IgG1 | 552532 | BD Pharmingen |
| Anti-4-1BB BMS-663513 (Urelumab) | Fully human IgG4 | | Bristol-Myers Squibb |

A 4-1BB antibody may also be any of the 4-1BB antibodies disclosed in U.S. Pat. Nos. 8,137,667 and 8,337,850, the contents of which are incorporated herein by reference in their entirety. These 4-1BB antibodies include the anti-4-1BB antibodies (anti-human 4-1-bb, MOR-6032 and MOR-7361) described in Table 4B. A 4-1BB antibody may also be any chimeric, humanized or fully human antibody comprising the CDRs of the anti-4-1BB antibodies of Table 4B. The CDRs and variable regions of these clones are as indicated in the table below (HC=heavy chain; LC=light chain).

TABLE 4B

| Antibody | SEQ ID NO: | Description |
|---|---|---|
| Anti-human 4-1bb (fully human Ab) | 93 | CDRs at:<br>amino acid position 50-54 of SEQ ID NO: 93<br>amino acid position 69-84 of SEQ ID NO: 93<br>amino acid position 117-129 of SEQ ID NO: 93<br>HC at amino acid position 20-467 |
| | 94 | CDRs at:<br>amino acid position 44-54 of SEQ ID NO: 94<br>amino acid position 70-76 of SEQ ID NO: 94<br>amino acid position 109-119 of SEQ ID NO: 94<br>LC at amino acid position 21-236 |
| Anti-human 4-1bb MOR-6032 | 99 | Full length heavy chain |
| | 104 | Full length light chain |
| | 98 | Variable Region of HC |
| | 103 | Variable Region of LC |
| | 95 | H-CDR1 |
| | 96 | H-CDR2 |
| | 97 | H-CDR3 |
| | 100 | L-CDR1 |
| | 101 | L-CDR2 |
| | 102 | L-CDR3 |

TABLE 4B-continued

| Antibody | SEQ ID NO: | Description |
|---|---|---|
| Anti-4-1bb | 109 | Full length heavy chain |
| MOR-7361 | 114 | Full length light chain |
| | 108 | Variable Region of HC |
| | 113 | Variable Region of LC |
| | 105 | H-CDR1 |
| | 106 | H-CDR2 |
| | 107 | H-CDR3 |
| | 110 | L-CDR1 |
| | 111 | L-CDR2 |
| | 112 | L-CDR3 |

C. Combination Therapy

The compositions and related methods, particularly administration of an siRNA to inhibit expression of T-cell anergy gene or a peptide, antibody or drug to inhibit said gene product to a patient/subject, may also be used in combination with the administration of traditional therapies or immunotherapies, such as, for example, traditional cancer therapies (such as chemotherapeutics, radiation, and/or surgery).

The compositions and related methods, particularly administration of an siRNA to inhibit expression of T-cell anergy gene or a peptide, antibody or drug to inhibit said gene product to a patient/subject may also be used in combination with the administration of one or more anti-cancer drugs that include but are not limited to Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine comprising recombinant L1 protein of HPV types 16 and 18), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine comprising recombinant L1 protein of HPV types 6, 11, 16, and 18), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Ibritumomab Tiuxetan, Ibrutinib, ICE, Iclusig (Ponatinib Hydrochloride), Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid) and Zytiga (Abiraterone Acetate).

The compositions and related methods, particularly administration of an siRNA to inhibit expression of T-cell anergy gene or a peptide, antibody or drug to inhibit said gene product to a patient/subject may also be used in combination with the administration of radiation therapy that includes but is not limited to X-rays, gamma rays, and charged particles. The radiation may be delivered by a machine outside the body (external-beam radiation therapy), or it may come from radioactive material placed in the body near cancer cells (internal radiation therapy or brachytherapy). Internal radiation therapy may be systemic (e.g. radioactive iodine). External-beam radiation therapy may include, but is not limited to, 3-dimensional conformal radiation therapy (3D-CRT), Intensity-modulated radiation therapy (IMRT), Image-guided radiation therapy (IGRT), Tomotherapy, Stereotactic radiosurgery (SRS), Stereotactic body radiation therapy (SBRT), Proton therapy or other charged particle beams (e.g., electron beams). Internal radiation therapy or brachytherapy may comprise interstitial brachytherapy which uses a radiation source placed within tumor tissue and may be used to deliver a dose higher than external beam radiation while causing less damage to normal tissue. Brachytherapy may be given as a low-dose rate or high-dose rate treatment. In additional embodiments, brachytherapy may be permanent or temporary. Radiation therapy may comprise systemic radiation therapy. Systemic radiation therapy may comprise a swallowed or injected radioactive substance, that includes, but is not limited to any single, multiple or combination dose of Radioactive iodine ($^{131}$I), ibritumomab tiuxetan (Zevalin®), 131 tositumomab (Bexxar®), samarium-153-lexidronam (Quadramet®) and strontium-89 chloride (Metastron) or any monoclonal bound to a radioactive substance. The dose of radiation according to different embodiments may be tailored to the specific disease, condition or cancered being treated. In some embodiments, the single or total dose may be 1-10 gray (Gy), 10-20 Gy, 20-40 Gy, 40-60 Gy, or 60-80 Gy, or any value or rage derivable therein. In some embodiments, radiation therapy or dose may be fractionated. In one embodiment, a total dose may be fractionated per day or per week. In certain embodiments the daily fractionated dose may be 1.8-2 Gy. It is contemplated that a total dose may be fractionated into daily or weekly doses in the range of 0.1 Gy to 10 Gy.

In one aspect, it is contemplated that a therapy is used in conjunction with anticancer treatment. Alternatively, the therapy may precede or follow the other agent treatment by intervals ranging from minutes to weeks. In embodiments where the other treatments and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example anticancer therapy or immunotherapy is "A" and an siRNA that targets T-cell anergy related gene is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

D. General Pharmaceutical Compositions

In some embodiments, pharmaceutical compositions are administered to a subject. Different aspects may involve administering an effective amount of a composition to a subject. In some embodiments, a therapeutic siRNA may be administered to the patient to alter the expression of genes associated with T-cell anergy. Alternatively, an expression vector encoding one or more such siRNAs may be given to a patient as a preventative treatment. Additionally, such compositions can be administered in combination with traditional therapy or immunotherapy, such as a traditional cancer therapy. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methods and Materials

Mice and T Cell Clones—CAR Tg mice expressing the extracellular domain of CAR under control of a Lck promoter/CD2 enhancer were generated as previously described (Wan et al., 2000). All mice were housed in pathogen-free conditions at the University of Chicago, and all animal protocols were approved by the Institutional Animal Care and Use Committee. To generate CAR Tg×Egr2$^{flox/flox}$ Th1 clones, CAR Tg×Egr2$^{flox/flox}$ mice were immunized in the hind footpads with chicken ovalbumin (OVA; A5503, Sigma) emulsified in complete Freund's adjuvant (F5881, Sigma). Seven days later, the draining lymph nodes were harvested, and CD4$^+$ Th1 cell clones were derived and maintained as previously described (Fitch et al., 2006; Gajewski and Fitch, 1990).

Adenovirus Transduction—A Cre-expressing adenovirus was produced as described (Zha et al., 2006; Zha et al., 2008). For T cell transduction, cells were suspended at high density of 10×10$^6$/mL in DMEM with 2% FBS, incubated with an EV or the Cre adenovirus at 37° C. for 50 minutes, transferred to DMEM with 10% FBS, and cultured for another 16 hours at low density of 1×10$^6$/mL.

Anergy Induction in vitro—In vitro anergy was induced by treating cells overnight with immobilized anti-CD3 mAb (1 µg/mL; 145-2C11, BioXCell). The cells were then harvested, washed, and rested for 1-2 days prior to analysis.

ChIP-seq Analysis—100 ng of DNA from the ChIP assays was ligated to the Illumina adaptor oligo mix according to the manufacturer's protocols. After 16 cycles of PCR amplification, the product was separated on 2% agarose gels, and DNA fragments between 150-400 bp were purified using a Gel Purification Kit (Qiagen). 8 pmoles of DNA was sequenced on an Illumina GAII sequencer according to standard protocols. For data analysis, images obtained from the sequencer were processed by Illumina image extraction pipeline software. Eland Extended was used to align sequences to mouse genome (NCBI 37/mm9). Non-unique sequences that aligned to more than two different locations were discarded prior to subsequent analysis. QuEST (Valouev et al., 2008) was used to identify enriched binding regions or peaks. MEME (Bailey et al., 2009) was used for motif identification. Two independent ChIP-seq experiments were performed, and genes present in both datasets were considered as positive.

Gene Expression Profiling Analysis—All RNA samples used for gene array analysis had RNA Integrity Number >8.0, OD260/280 and OD260/230 ratio >1.8. The RNA was labeled, fragmented and hybridized to Affymetrix mouse genome 430 2.0 expression arrays at the Functional Genomics Core Facility of the University of Chicago (Chicago, IL). The arrays were then scanned and CEL intensity files were generated by MicroArray Suite 5.0. The gene array analysis was performed three times using three sets of independently manipulated samples. Results from the three gene arrays were combined and analyzed using dChip software. Specifically, the genes scored as "absent" or with signal intensity <100 were first filtered out. Among the remaining genes, those with greater than or equal to a 2-fold increase in expression upon anergy induction were considered as anergy-associated genes, and those with more than a 1.5-fold reduction upon Egr2 deletion were considered as Egr2-dependent genes. Genes were considered as positive when the average fold changes of the three sets of samples met the thresholds listed above.

ChIP Assay—ChIP assays were conducted following the manufacturer's protocol (Millipore). Briefly, 2.5×10$^6$ cells were lysed in 500 µL SDS lysis buffer, and cellular DNA was sheared 6 times with a 15-second pulse plus 60-second rest using a Misonix Sonicator 3000 (Qsonica). For immunoprecipitation, 200 µL cell lysate supernatant (corresponding to 1×10$^6$ cells) was diluted 5 fold in ChIP dilution buffer, and anti-Egr2 Ab was added at a 1:100 dilution (PRB-236P, Covance). SYBR Green qRT-PCR was conducted using primers specific for CCL1 intron (forward 5'-AATGGCCA-CATGGAAAACTC-3' [SEQ ID NO. 1], reverse 5'-CCAAACATACCTCGAATACGC-3' [SEQ ID NO. 2]); Crtam intron (forward 5'-TCTGGACAGGAGGGGATGT-3' [SEQ ID NO. 3], reverse 5'-AGGAAACACC-CACAGCAAAG-3' [SEQ ID NO. 4]); Sema7A core promoter (forward 5'-GCTTCTGCTGGTGTTCTGG-3' [SEQ ID NO. 5], reverse 5'-CGCCTACCTTTCCAGACG-3' [SEQ ID NO. 6]); Lag3 core promoter (forward 5'-CTCCA-GACCCAGTCCTTCTG-3' [SEQ ID NO. 7], reverse 5'-ACACTTTCCACTGCGAAGC-3' [SEQ ID NO. 8]); 4-1BB 5'UTR (forward 5'-AATCTCTTAACTCAGGAGA-GACGTG-3' [SEQ ID NO. 9], reverse 5'-TTCCCAC-CACAGTGACATTC-3' [SEQ ID NO. 10]); Nrgn intron (forward 5'-GGCTTGGCTCAGATCAGG-3' [SEQ ID NO. 11], reverse 5'-GGGAAAGAATGGTGCTGAAA-3' [SEQ ID NO. 12]); Nrn1 proximal promoter (forward 5'-GTGACTGATTTTCATCCCAGTG-3' [SEQ ID NO. 13], reverse 5'-ACCAGGACTCCCCGTCTC-3' [SEQ ID NO. 14]); Bcl2l11 core promoter (forward 5'-TCCACTTGGAT-TCACACCAC-3' [SEQ ID NO. 15], reverse 5'-CAGACAT-TGGGTGGACGAG-3' [SEQ ID NO. 16]); Crabp2 proximal promoter (forward 5'-CTTGCCTTCTGACGCTTCTC-3' [SEQ ID NO. 17], reverse 5'-GGGTTCTCCAAGAGCCAAG-3' [SEQ ID NO. 18]). Primers specific for GJA5 were used as controls (forward 5'-ACCATGGAGGTGGCCTTCA-3' [SEQ ID NO. 19], reverse 5'-CATGCAGGGTATCCAGGAAGA-3' [SEQ ID NO. 20]).

qRT-PCR—The primers and probes were purchased from IDT, Roche, and Applied Biosystems. qRT-PCR used primers and probes specific for CCL1 (forward 5'-TCACCAT-GAAACCCACTGC-3' [SEQ ID NO. 21], reverse 5'-AGCAGCAGCTATTGGAGACC-3' [SEQ ID NO. 22], CTGGCTGC [SEQ ID NO. 23]); Crtam (forward 5'-AG-ATCCAACAACGAGGAGACA-3' [SEQ ID NO. 24], reverse 5'-TCATGCAACGCTTAGACTGG-3' [SEQ ID NO. 25], CTGGCTGC [SEQ ID NO. 23]); Sema7A (forward 5'-TCAATCGGCTGCAAGATGT-3' [SEQ ID NO. 26], reverse 5'-CGCAGACAGCTGAGTAGTTCC-3' [SEQ ID NO. 27], GAGCAGGA [SEQ ID NO. 28]); Lag3 (forward 5'-TGCTTTGGGAAGCTCCAGT-3' [SEQ ID NO. 29], reverse 5'-GCTGCAGGGAAGATGGAC-3' [SEQ ID NO. 30], CCAGGAGG [SEQ ID NO.31]); 4-1BB (forward 5'-GAACGGTACTGGCGTCTGTC-3' [SEQ ID NO. 32], reverse 5'-CCGGTCTTAAGCACAGACCT-3' [SEQ ID NO. 33], CTGCTCTC [SEQ ID NO. 34]); Nrgn (forward 5'-AACACCGGCAATGGACTG-3' [SEQ ID NO. 35], reverse 5'-AAACTCGCCTGGATTTTGG-3' [SEQ ID NO. 36], GCTGGATG [SEQ ID NO. 37]); Nrn (forward 5'-TCCTCGCGGTGCAAATAG-3' [SEQ ID NO. 38], reverse 5'-GCCCTTAAAGACTGCATCACA-3' [SEQ ID NO. 39], CTGCTCTC [SEQ ID NO. 34]); Bcl2l11 (forward 5'-GGAGACGAGTTCAACGAAACTT-3' [SEQ ID NO. 40], reverse 5'-AACAGTTGTAAGATAACCATTTGAGG- 3' [SEQ ID NO. 41], GGCTGAAG [SEQ ID NO. 42]); Crabp2 (forward 5'-AAATGGTGTGCGAGCAGAG-3' [SEQ ID NO. 43], reverse 5'-AACGTCATCTGCTGTCAT-TGTC-3' [SEQ ID NO. 44], CCAGGAGG [SEQ ID NO. 31]). Relative RNA abundance was determined based on control 18S RNA (Hs99999901_s1, Applied Biosystems).

Immunoblot Analysis—Equal numbers of T cells were resuspended in ice-cold lysis buffer containing 50 mM Tris (pH 7.6), 5 mM EDTA, 150 mM NaCl, 0.5% Triton x-100, 1 mM PMSF, 10 mM NaF, 1 mM $Na_3VO_4$, and 1× protease inhibitor mixture (Roche). After 30-minute incubation on ice, the cells were spun for 10 minutes at top speed at 4C, and supernatant was collected. The cellular lysate was loaded into 10% Tris-HCL gels (Bio-Rad Laboratories), separated by SDS-PAGE, and transferred to PVDF membranes (Millipore). Proteins were detected using primary antibodies against Sema7A (1:1000, AF1835, R&D System) and Crabp2 (1:1000, MAB5488, Millipore); secondary antibodies were HRP-linked anti-mouse IgG (1:3000, GE Healthcare). Detection was performed using an ECL Detection Kit (GE Healthcare).

Flow Cytometry—To stain Crtam, cells were incubated with an anti-Crtam mouse IgG2a (30 ng/mL, 10 µl per $1×10^6$ cells at 4° C. for 20 minutes, and then an Alexa Fluor 647 goat anti-mouse IgG2a (1:100; A21241, Invitrogen) at 4° C. for another 20 minutes.

Example 2—Identification of Egr2 Transcriptome Using Microarray-Based Gene Expression Profiling and ChIP-Seq Analyses Th1 T cell clones anergized by immobilized anti-CD3 were used as the inventors' T cell anergy model. This model has been well-characterized and can provide sufficient cellular material for microarray and ChIP-seq analyses (Schwartz, 2003). T cell-specific Egr2 deletion was mediated by use of a Cre-expressing adenovirus and a Coxsackie/adenovirus receptor (CAR) Tg×Egr2$^{flox/flox}$ mouse in which CAR is expressed exclusively in the T cell compartment from a Lck promoter/CD2 enhancer cassette. This system allows for peripheral deletion of Egr2 without affecting T cell development in the thymus, as the inventors recently described (Zha et al., 2008). Briefly, OVA-specific Th1 T cell clones were generated from CAR Tg×Egr2$^{flox/flox}$ mice (Fitch et al., 2006; Zha et al., 2008). Egr2 deletion was then achieved by transduction of the CAR Tg×Egr2$^{flox/flox}$ Th T cell clones with the Cre adenovirus. This system was proven very efficient, qRT-PCT and immunoblot confirmed anti-CD3 induced Egr2 expression was decreased to minimal levels after the Cre adenovirus mediated Egr2 deletion (Zheng et al, 2012).

In order to map the complete Egr2 transcriptome of anergic T cells, the inventors conducted two sets of genome-wide screens. The first was a microarray-based gene expression profiling analysis in which anergic Th1 cells were compared with or without prior Egr2 deletion. Specifically, CAR Tg×Egr2$^{flox/flox}$ Th1 T cells were infected with an empty (EV) or a Cre-expressing adenovirus. Upon confirmation of Egr2 deletion by immunoblot, the T cells were anergized by immobilized anti-CD3 for 16 hours, and microarray was conducted after 1 days of rest in culture medium. This analysis helped to identify the set of genes upregulated upon anergy induction in an Egr2-dependent manner (Supplementary Table 1). Gene array analysis revealed that 938 out of the total 45101 probes demonstrated at least a 2-fold increase upon anergy induction. Among those, 90 probes met the inventors' defined criteria for Egr2-dependence, in that the elevated gene expression seen in anergy was reduced by more than 1.5-fold in Egr2-deleted cells.

To identify the direct transcriptional targets of Egr2, the inventors also performed a ChIP-seq analysis. CAR Tg×Egr2$^{flox/flox}$ Th1 T cells were untreated or anergized by immobilized anti-CD3, cross-linked, and nuclear exacts were immunoprecipated by an anti-Egr2 Ab. ChIP-seq analysis was carried out on the DNA fragments bound to Egr2. Egr2 was found to be associated with a variety of regulatory regions in the genome of anergic T cells, of which 13% were located in core promoters (50 bp upstream of transcription start site (TSS)), 40% in proximal promoters (500 bp upstream of TSS), 20% in 5'UTRs, and 21% in introns (FIG. 1A). These binding interactions appeared to be specific, since the consensus sequence of Egr2 binding site derived from ChIP-seq was highly similar to that published on TRANSFAC, a comprehensive transcription factor database (FIG. 1B).

When the gene array results were merged with the ChIP-seq data, 62 of the 90 probes that showed Egr2-dependency for their expression were found to be directly bound by Egr2. Because of some duplication, those 62 probes represented 49 genes (FIG. 1C). In summary, 2.08% (938/45101) of the gene array probes demonstrated upregulation upon anergy induction, among which 9.59% (90/938) were dependent on Egr2, and 6.61% (62/938) were directly regulated by Egr2.

Example 3—Characterization of Novel Targets of Egr2 in the Anergic T Cells

Previous mechanistic studies of T cell anergy have focused attention on identifying the key factors that are causal for T cell intrinsic dysfunction. However, a striking feature of the additional genes identified through the gene array/ChIP-seq analyses is that several of the gene products are surface molecules or secreted factors. This observation suggests that anergic T cells may have additional functional properties oriented towards other cellular components of the immune system.

Nine of the newly identified Egr2-dependent targets were studied in more detail, including the chemokine CCL1; five cell surface receptors (Semaphorin 7A (Sema7A), Class-I-MHC-restricted T cell associated molecule (Crtam), lymphocyte-activation gene 3 (Lag3), tumor necrosis factor receptor superfamily member 9 (Tnfrsf9, or 4-1BB), and Neuritin (Nrn1)); and three intracellular proteins (BCL2-like 11 (Bcl2l11 or Bim), Neurogranin (Nrgn), and cellular retinoic acid-binding protein 2 (Crapb2)). CCL1 is a member of the C—C motif chemokine family, and a recent publication indicated that CCL1 can recruit Foxp3$^+$ regulatory T cells in the tumor context (Hoelzinger et al., 2010). Semaphorin 7A (Sema7A) belongs to membrane-bound Semaphorin family that associates with the plasma membrane via a GPI linker (Suzuki et al., 2008). Crtam is a type I transmembrane protein with V and Cl-like Ig domains (Du Pasquier, 2004). Lag3, a CD4-related transmembrane protein, binds to MHC class II on APCs with higher affinity than does CD4 and has been reported to function as an inhibitory receptor (Baixeras et al., 1992; Grosso et al., 2007; Huang et al., 2004; Triebel et al., 1990). 4-1BB is an inducible costimulation receptor on T cells, and belongs to the tumor necrosis factor receptor superfamily (Watts, 2005). Nrn1 is a neural activity-regulated gene, encoding a small extracellular protein that serves as a neurotrophin to promote neuritogenesis, neuronal survival, and plasticity (Naeve et al., 1997; Nedivi et al., 1996; Nedivi et al., 1998). Nrgn is another protein that has been mainly studied in the central neural system (Diez-Guerra, 2010). It interacts with calmodulin and regulates intracellular concentrations of calcium, and calcium-derived signaling in synapses. The functions of Nrn1 and Nrgn in the immune system are yet to be clarified. Bcl2l11 is a pro-apoptosis proteins in the intrinsic apoptosis pathway, and has been shown to regulate T cell deletion in both thymus and the peripheral (Bouillet and O'Reilly, 2009). Its interaction with pro-survival protein Bcl-2 releases BCL-2-associated X protein (BAX) and BCL-2 antagonist/killer (BAK) to trigger mitochondria-mediated apoptosis. Crabp2 is a retinoic acid binding protein, delivering retinoid acid from the cytoplasm to its selective receptors located in the nucleus (Hall et al., 2011).

Figure 2:
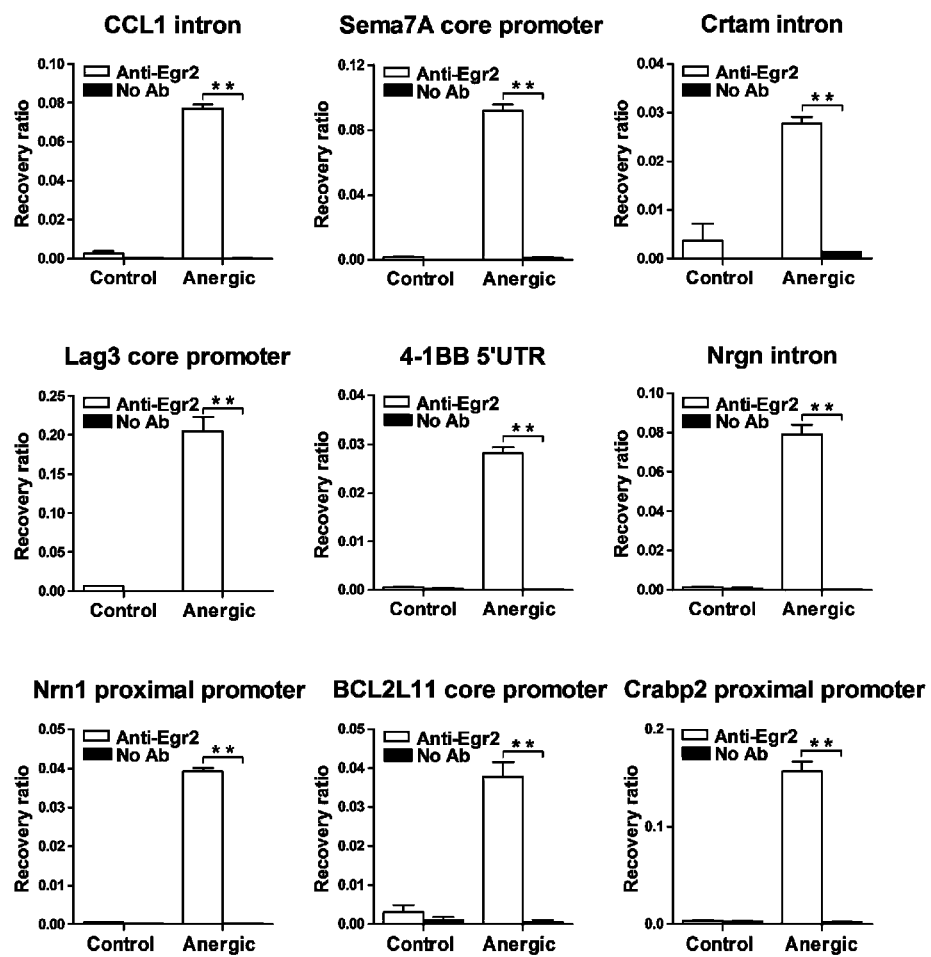
FIG. 2—Confirmatory ChIP assay on selected targets of Egr2. CAR Tg×Egr2$^{flox/flox}$ Th1 T cells were left untreated (Control) or anergized with immobilized anti-CD3 mAb (Anergic), cross-linked, the cell lysate were immunoprecipitated by anti-Egr2-coated beads or empty beads, and the association of Egr2 with the indicated genes was determined by ChIP Assay. Data are presented as mean+/−SD, and are representative of three independent experiments, **p<0.01.
Figure 3:
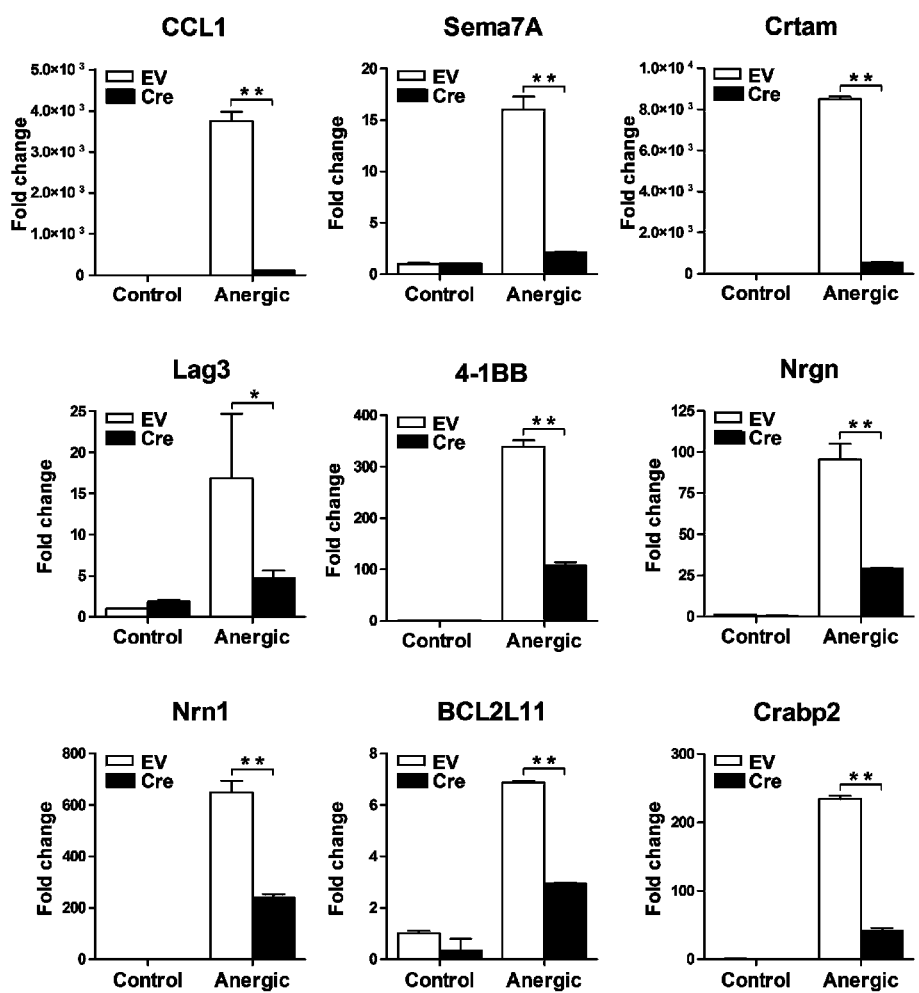
FIG. 3—Confirmatory qRT-PCR on selected targets of Egr2. CAR Tg×Egr2$^{flox/flox}$ Th1 clones were infected with an EV- or a Cre-expressing adenovirus to delete Egr2. The cells were then left untreated (Control) or anergized with immobilized anti-CD3 mAb (Anergic), and the expression of the indicated genes was examined by qRT-PCR. Data are presented as mean+/−SD, and are representative of three independent experiments, * p<0.05, **p<0.01.
Figures 4A, 4B, 4C, 4D:
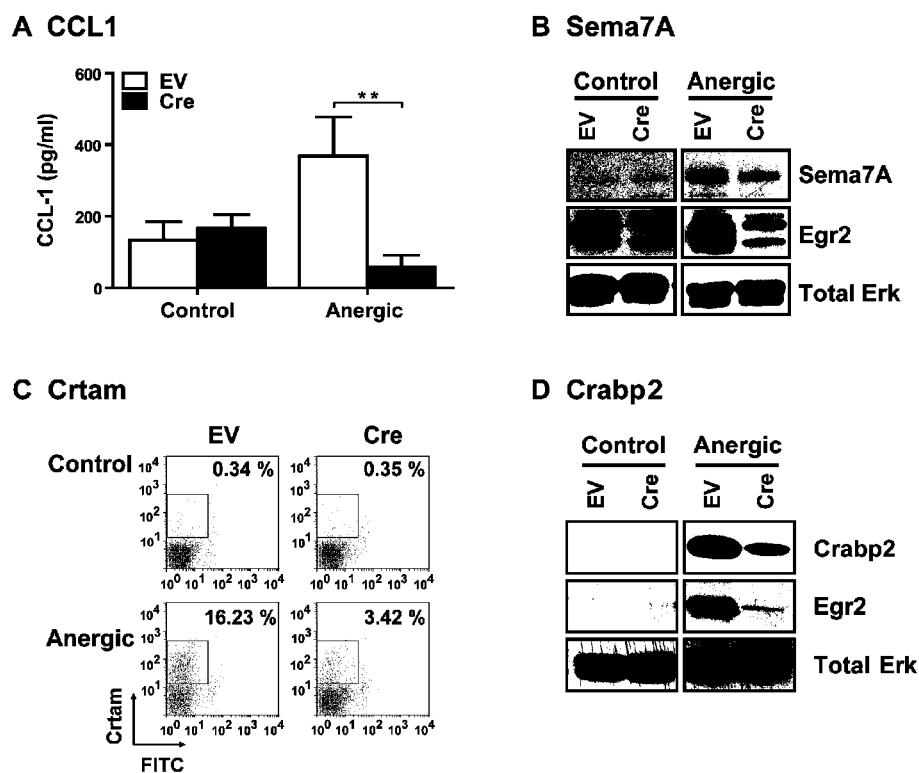
FIG. 4A-4D—Confirmatory protein expression on selected targets of Egr2. CAR Tg×Egr2$^{flox/flox}$ Th1 clones were infected with an EV- or a Cre-expressing adenovirus to delete Egr2. The cells were then left untreated (Control) or anergized with immobilized anti-CD3 mAb (Anergic), and the expressions of CCL1, Sema7A, Crtam, and Crabp2 were examined by ELISA (A), Immunoblot (B and D), and flow cytometry (C) respectively. Data are presented as mean+/−SD, and are representative of two to six independent experiments, **p<0.01.
Figure 5:
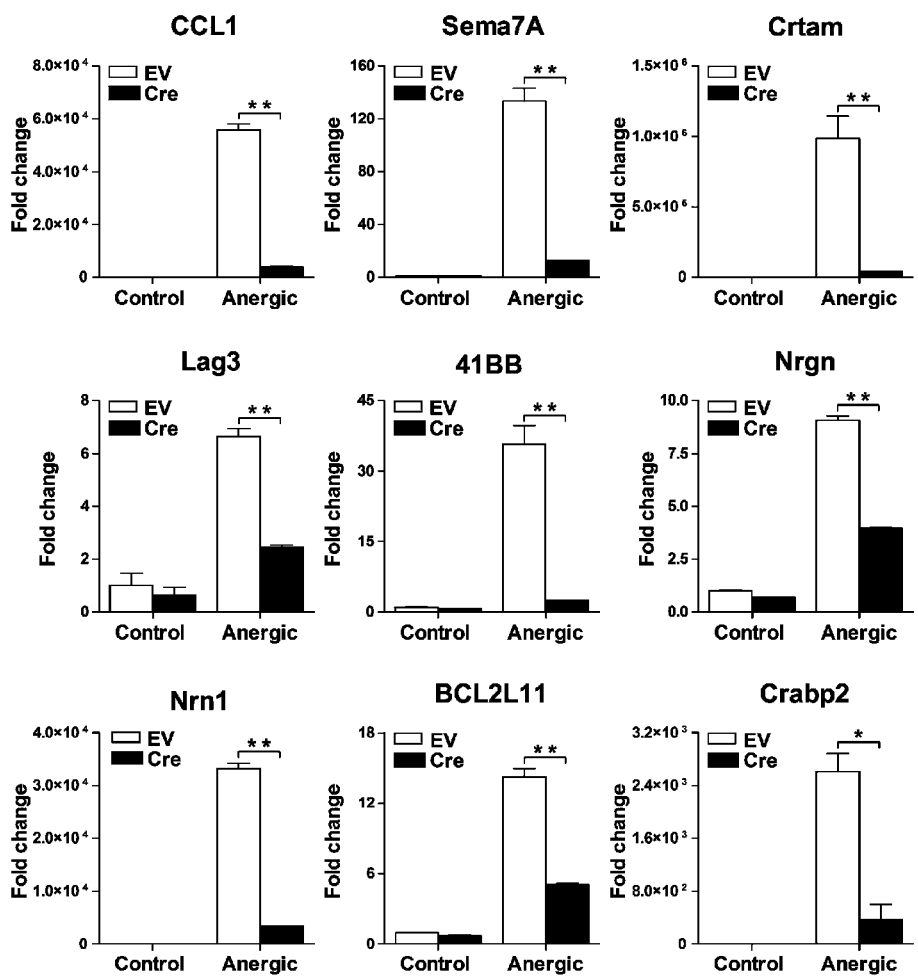
FIG. 5—The role of Egr2 in regulating the indicated genes is confirmed in CAR Tg×Egr2$^{flox/flox}$ Th1 T cell clone 11. (A-B) CAR Tg×Egr2$^{flox/flox}$ Th1 clone 11 cells were infected with an EV- or a Cre-expressing adenovirus to delete Egr2. The cells were then left untreated (Control) or anergized with immobilized anti-CD3 mAb (Anergic), and the expression of the indicated genes was examined by qRT-PCR. Data are presented as mean+/−SD, and are representative of two independent experiments, * p<0.05, **p<0.01.
Figure 6:
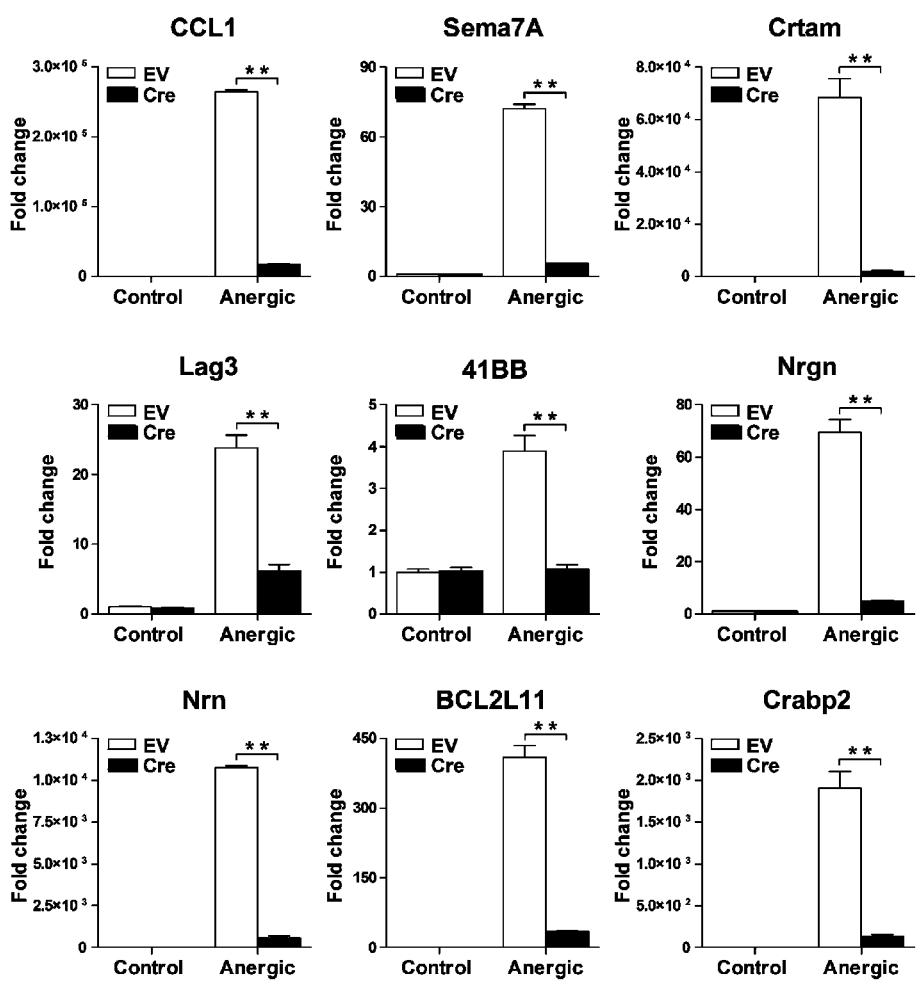
FIG. 6—The role of Egr2 in regulating the indicated genes is confirmed in CAR Tg×Egr2$^{flox/flox}$Th1 T cell clone 46. (A-B) CAR Tg×Egr2$^{flox/flox}$ Th1 clone 46 cells were infected with an EV- or a Cre-expressing adenovirus to delete Egr2. The cells were then left untreated (Control) or anergized with immobilized anti-CD3 mAb (Anergic), and the expression of the indicated genes was examined by qRT-PCR. Data are presented as mean+/−SD, and are representative of two independent experiments, **p<0.01.

Binding of Egr2 to theses nine genes upon anergy induction was confirmed by ChIP assay. As shown in FIG. 2, Egr2 was associated with variable regulatory regions of these genes upon immobilized anti-CD3 treatment. Egr2-dependent mRNA expression in anergic T cells was confirmed by qRT-PCR. As seen in FIG. 3, TCR engagement alone highly upregulated these genes, and their expressions were reduced substantially with Egr2 deletion. Similar results were also seen in two other CAR TgxEgr2$^{flox/flox}$ Th T cell clones (FIGS. 5 and 6). To further validate the qRT-PCR results, the inventors analyzed the expression of four gene products at protein level, as there were reagents available for this analysis. ELISA revealed that CCL1 was constitutively secreted by anergic cells in an Egr2-dependent manner (FIG. 4A). The expression of Sema7A and Crapb2 proteins were detected by immunoblot in anergic cells, which were partially reduced in the absence of Egr2 (FIGS. 4B and 4D). Similarly, cell surface expression of Crtam was detected by flow cytometry on at least 14.60±1.88% anergic cells, and diminished to 3.41±0.2% when Egr2 was deleted (FIG. 4C represents one of six experiments). These results indicate that Egr2 directly contributes to the expression of these nine genes in anergic cells.

Figure 7:
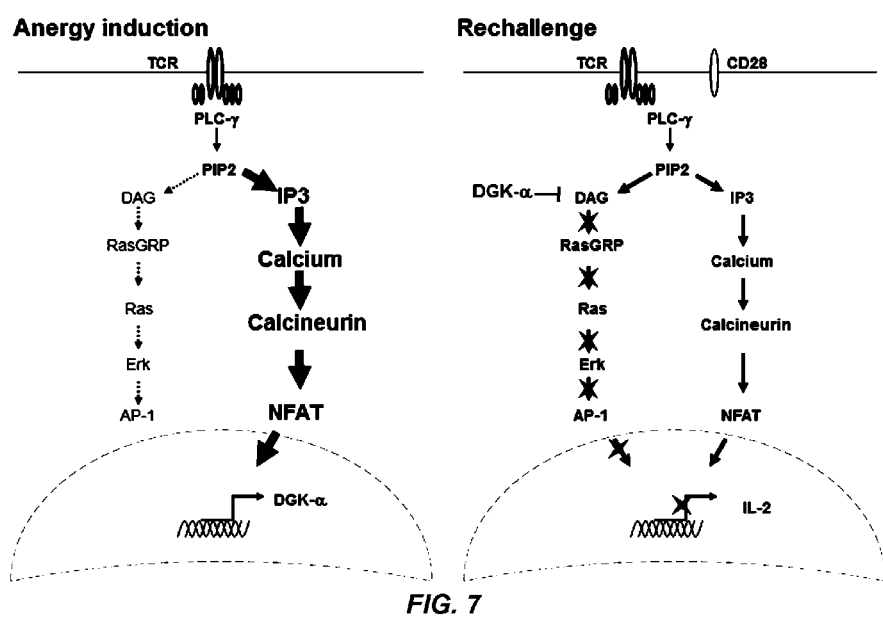
FIG. 7—Model for DGK-α in T cell anergy.
Figure 8:
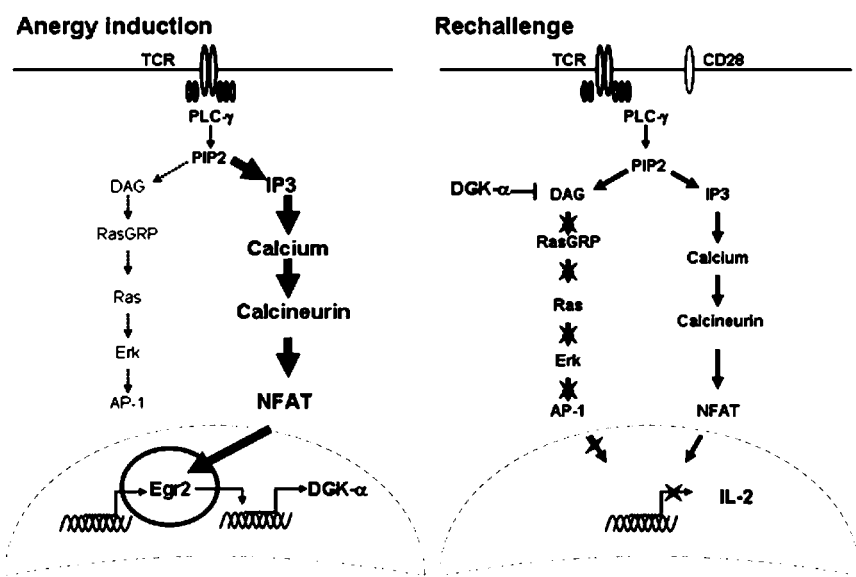
FIG. 8—DGK-α appears to be regulated by EGR2.
Figure 9:
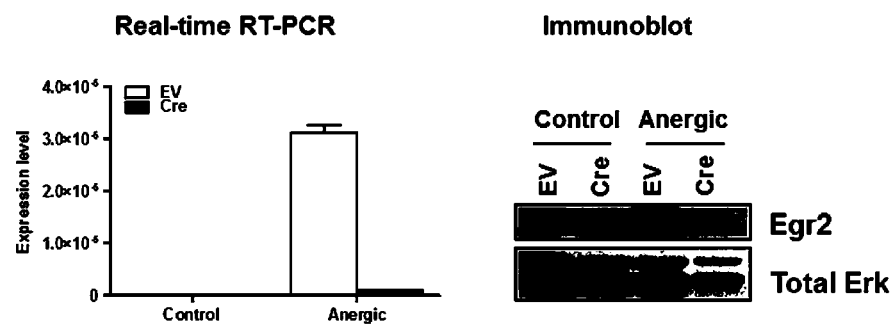
FIG. 9—Adeno-Cre transduction of CARTg×Egr2$^{fl/fl}$ Th1 cells deletion of Egr2.
Figure 10:
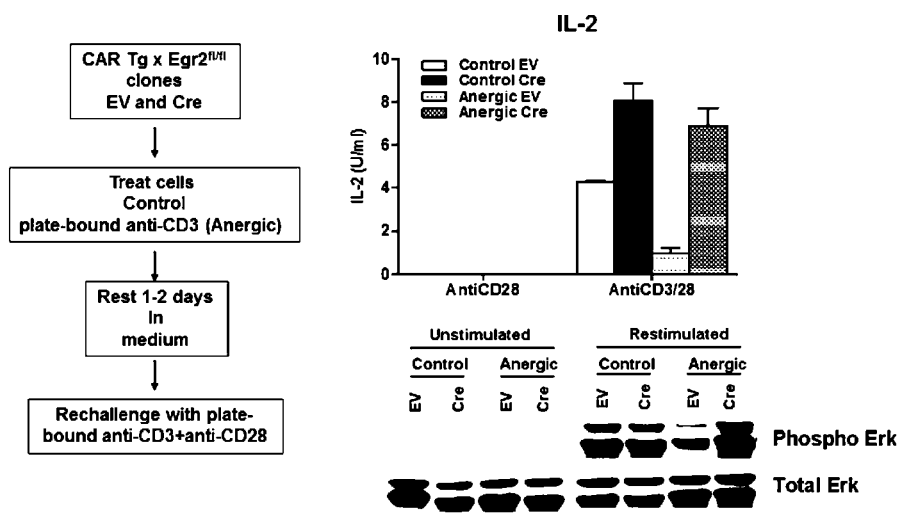
FIG. 10—Egr2 deletion leads to resistance to anergy induction in vitro.
Figure 11:
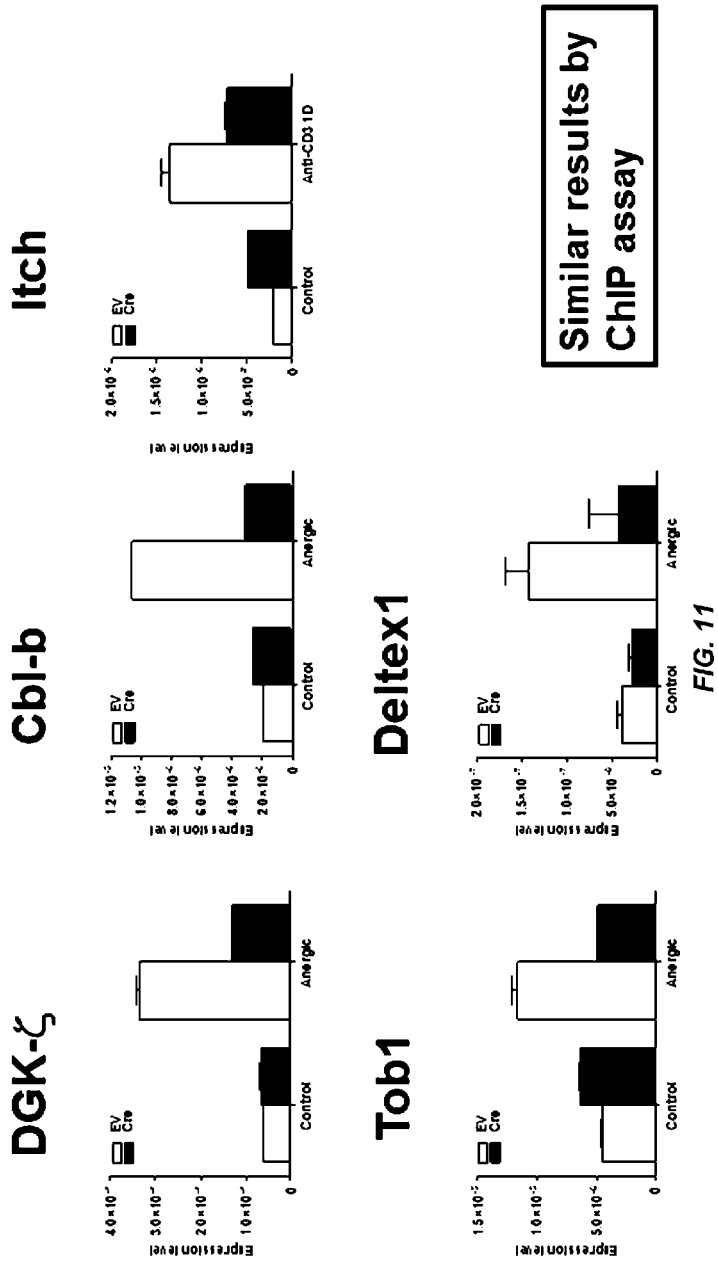
FIG. 11—Egr2 directly regulates most of the known anergy associated genes: qRT-PCR.
Figure 12:
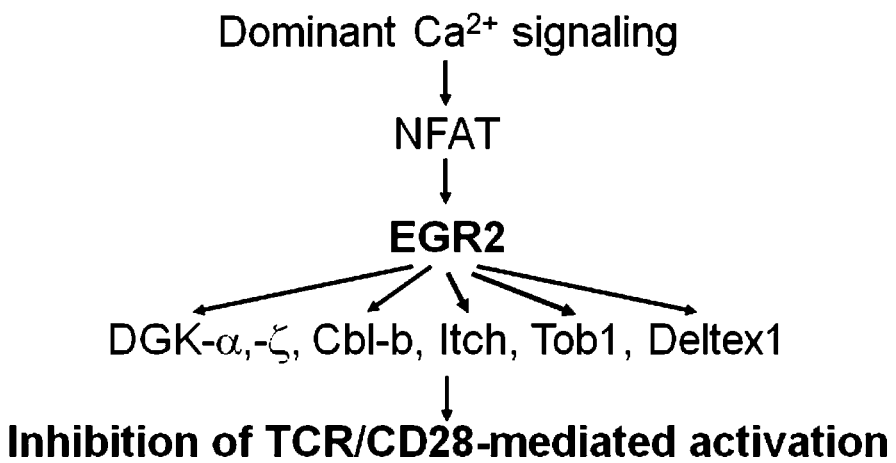
FIG. 12—Model for Egr2 as central transcriptional regulator of T cell anergy.
Figure 13:
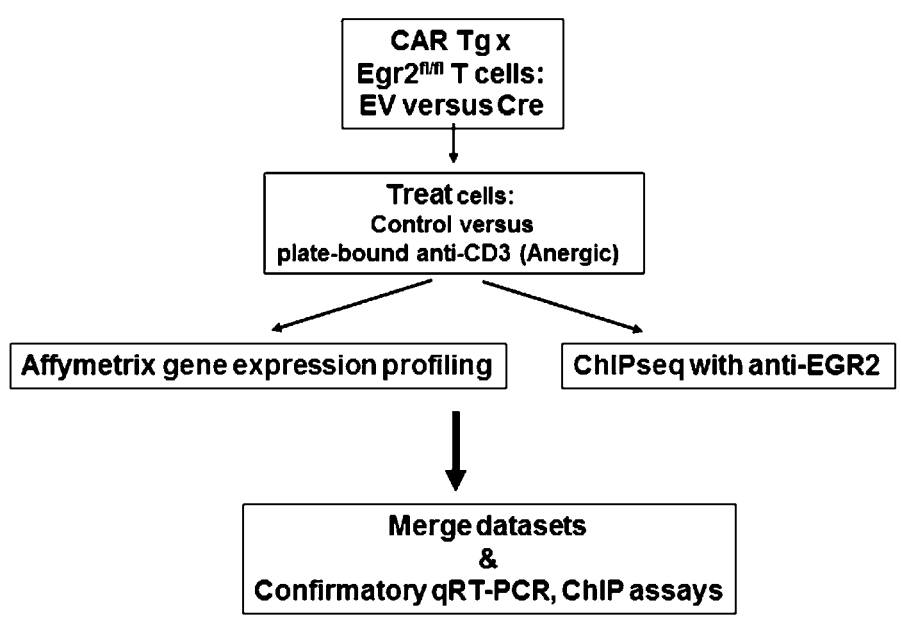
FIG. 13—Strategy to determine global Egr2-driven transcriptional program in anergic T cells.
Figure 15:
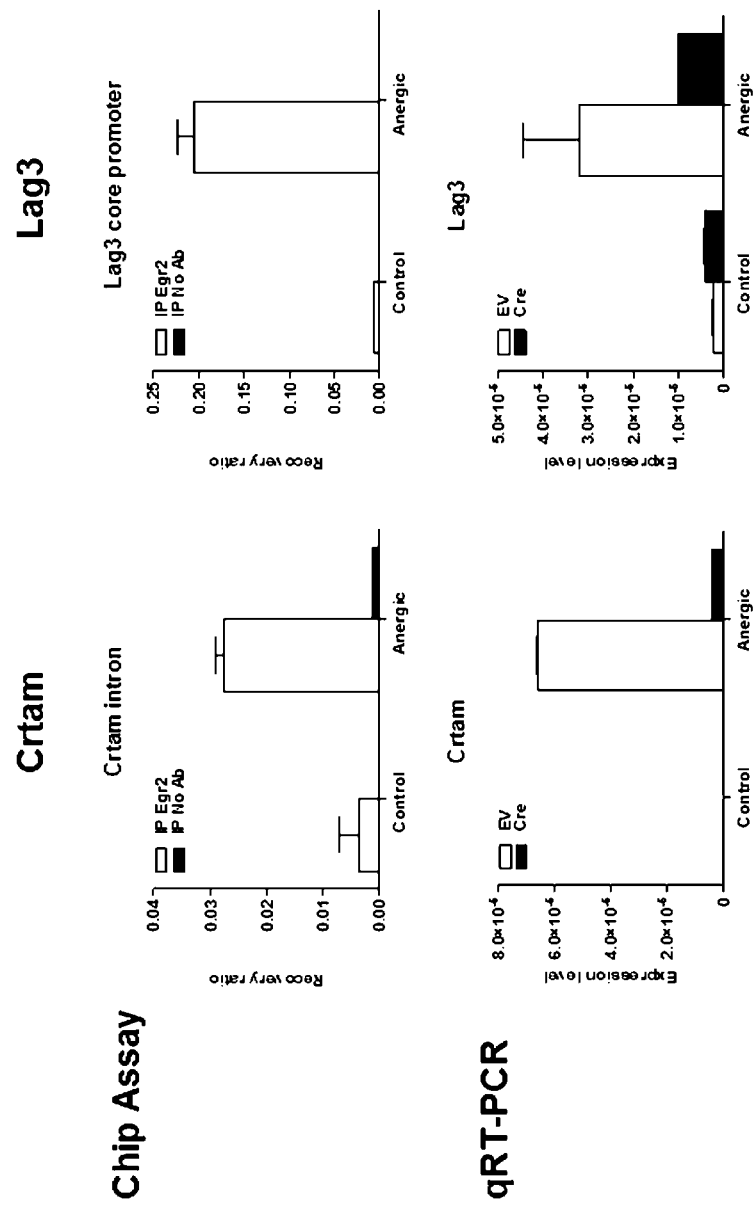
Figure 16:
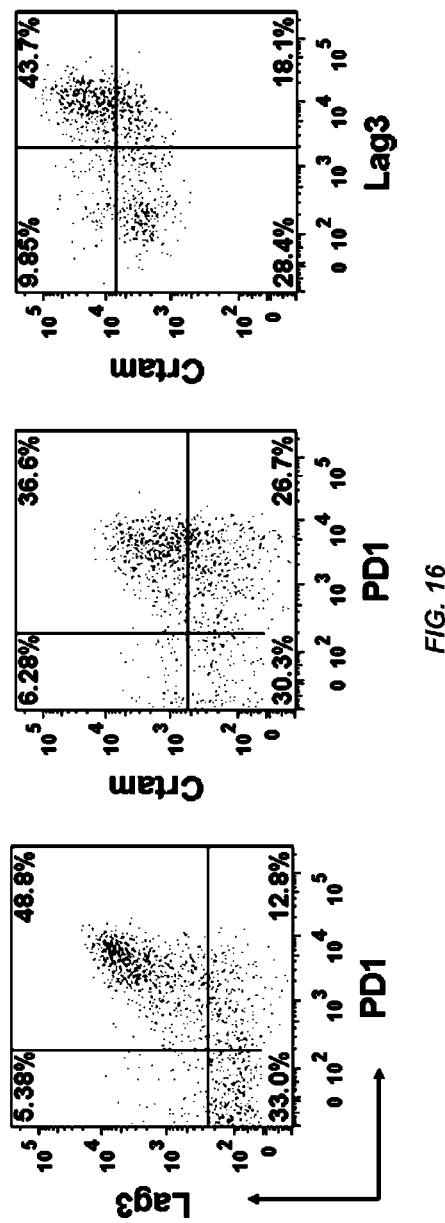
Figure 17:
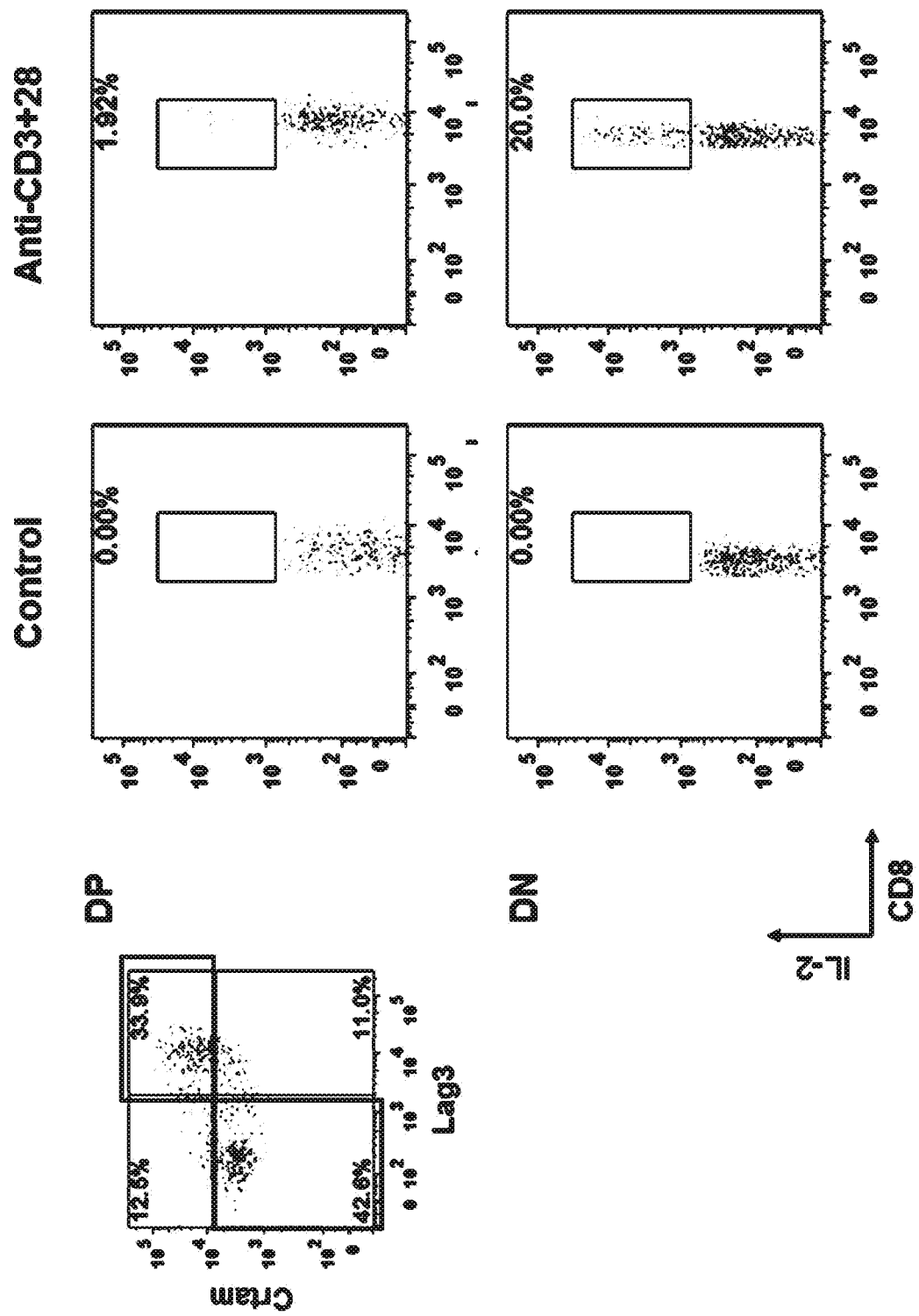
Figure 18:
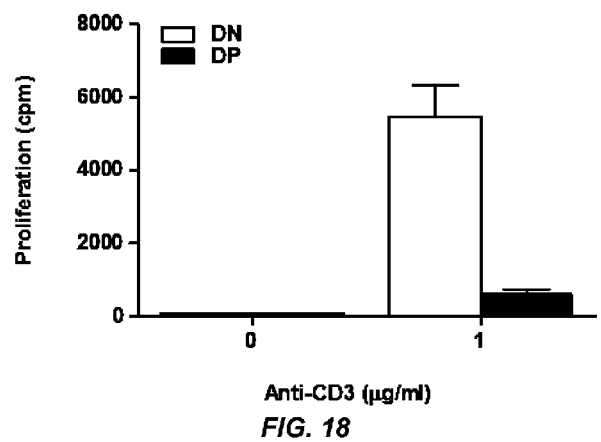
Figure 19:
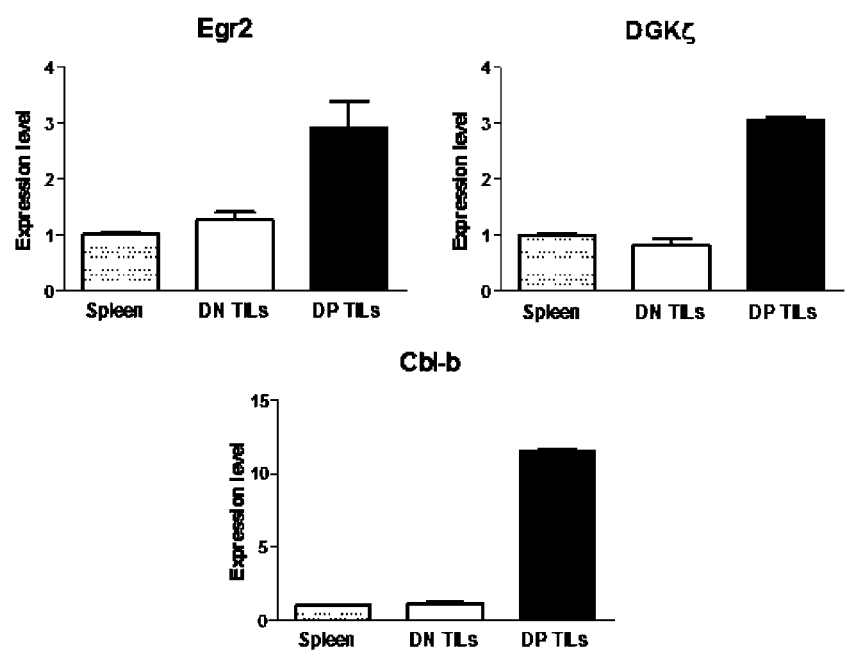
Figure 20:
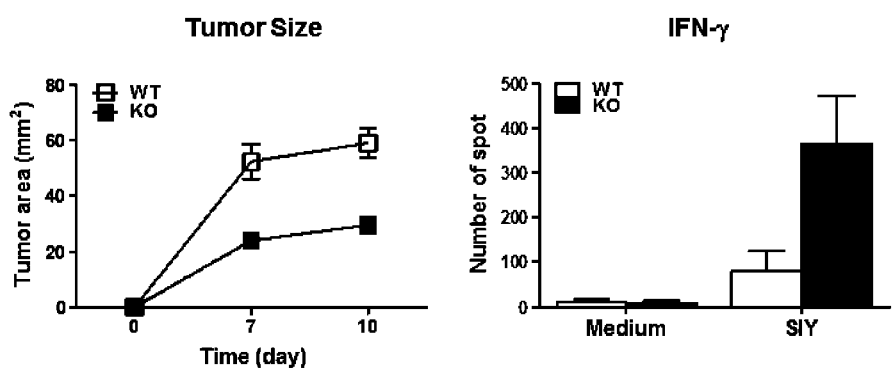

Several genes encoding negative regulatory molecules are upregulated in anergic T cells (see FIGS. 7-9). Such genes include, for example, DGK-ζ, Cbl-b, GRAIL, Itch, Tob1, and Deltex1. It was also demonstrated that Egr2-deleted T cells are relative anergy-resistant in vitro (see FIG. 10) and also in vivo (data not shown). Additional genes regulated by Egr2 were identified using strategies including real-time PCR and ChIP assays, as well as gene expression profiling of conditional Egr2-deleted T cells with ChIP-SEQ analysis of genes directly binding to Egr2. These experiments demonstrated that Egr2 is a major transcriptional regulator of the anergic state and identified the Egr2 transcriptome in T cell anergy (see FIGS. 11-14). Further studies showed that Crtram (Class-I-MHC-restricted T cell associated molecule) and Lag3 (lymphocyte-activation gene 3) are Egr2-dependent anergy-associated genes (see FIG. 15) and may identify the population of anergic T cells from the tumor microenvironment ex vivo (see FIGS. 16-20).

Example 4—Characterization of Novel Targets of Egr2 in the Anergic T Cells

Female C57BL/6 mice purchased from Taconic were injected with 2×10^6 B16.SIY subcutaneously (Day 0). Beginning on Day 4, mice were injected with 100 μg of either anti-4-1BB (4-1BB antibody clone LOB12.3) or anti-LAG-3 antibody (LAG-3 antibody clone C9B7W), or 100 μg of anti-4-1BB antibody plus 100 μg of anti-LAG-3 antibody. Mice received treatments on Days 4, 7, 10 and 13. Tumors were measured beginning on Day 7. Tumor areas were calculated as the product of the longest tumor diameter and the diameter perpendicular to that. Tumors were measured after Day 7 on the indicated days.

Figure 21:
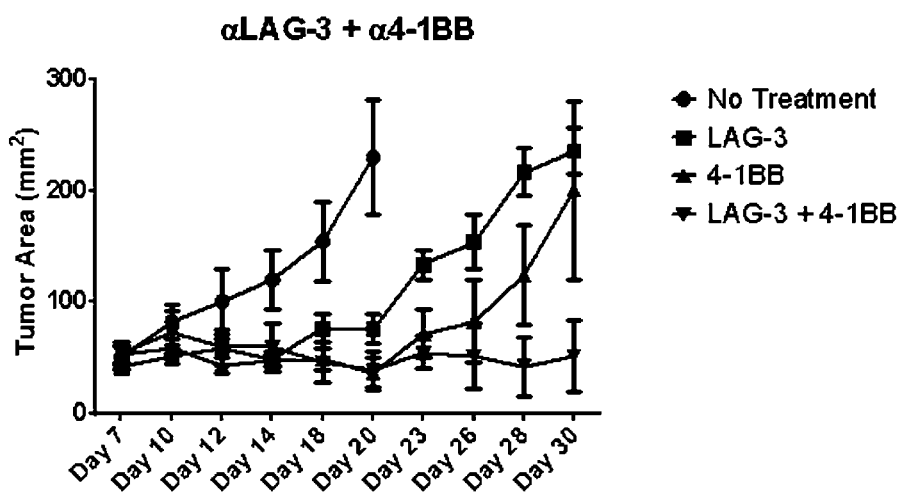

4-1BB and LAG-3 single antibody treatments both provided partial tumor control, however this control was temporary and tumors regrew. Combined treatment with 4-1BB and LAG-3 antibodies provided very robust tumor control, with 60% of mice in this group having no palpable tumor 30 days after tumor injection (FIG. 21). This demonstrates that combining treatments against two or more anergy associated targets can markedly improve immune-mediated tumor control.

TABLE 1

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| NM_019465 | 54698 | 37.62 | 6042.76 | 160.62 | 41.68 | 2843.67 | 68.23 | 36.94 | 2524.99 | 68.36 | 99.07 |
| AF128196 | 20308 | 16.45 | 1080.96 | 65.73 | 16.11 | 376.95 | 23.4 | 28.27 | 2210.41 | 78.19 | 55.77 |
| AK003046 | 68404 | 198.49 | 6839.14 | 34.46 | 119.04 | 8426.23 | 70.78 | 178.63 | 4604.82 | 25.78 | 43.67 |
| NM_011329 | 20290 | 100.28 | 6885.64 | 68.67 | 132.65 | 2909.69 | 21.93 | 86.35 | 1939.45 | 22.46 | 37.69 |
| X06746 | 13654 | 119.94 | 4756.51 | 39.66 | 71.98 | 2490.8 | 34.6 | 82.73 | 2183.82 | 26.4 | 33.55 |
| X06746 | 13654 | 163.45 | 6015.28 | 36.8 | 114.43 | 3489.41 | 30.49 | 114.33 | 3120.32 | 27.29 | 31.53 |
| NM_009375 | 21819 | 71.77 | 2168.62 | 30.22 | 114.04 | 1949.49 | 17.1 | 98.42 | 3311.95 | 33.65 | 26.99 |
| NM_010372 | 14941 | 44.37 | 660.44 | 14.89 | 138.37 | 3081.58 | 22.27 | 29.81 | 1010.2 | 33.89 | 23.68 |
| U94828 | 19734 | 35.03 | 616.21 | 17.59 | 63.44 | 2178.53 | 34.34 | 37.77 | 424.3 | 11.23 | 21.05 |
| NM_010372 | 14941 | 49.16 | 716.56 | 14.57 | 169.47 | 3336.17 | 19.69 | 38.06 | 1092.99 | 28.72 | 20.99 |
| NM_009877 | 12578 | 17.32 | 451.49 | 26.07 | 47.03 | 1223.11 | 26.01 | 27.67 | 300.22 | 10.85 | 20.98 |
| AF128196 | 20308 | 95.12 | 1597.89 | 16.8 | 97.88 | 650.4 | 6.64 | 102.47 | 3631.53 | 35.44 | 19.63 |
| NM_013542 | 14939 | 238.24 | 2842.26 | 11.93 | 185.57 | 1756.16 | 9.46 | 249.25 | 7554.5 | 30.31 | 17.23 |
| M12573 | 15511 | 58.18 | 1154.01 | 19.83 | 25.23 | 446.53 | 17.7 | 69.25 | 941.26 | 13.59 | 17.04 |
| NM_011337 | 20302 | 267.54 | 2340.01 | 8.75 | 95.01 | 2970.04 | 31.26 | 436.58 | 3000.83 | 6.87 | 15.63 |
| U72881 | 19734 | 43.4 | 448.32 | 10.33 | 47.31 | 1311.74 | 27.73 | 41.48 | 340.96 | 8.22 | 15.43 |
| NM_011454 | 20708 | 95.92 | 1908.44 | 19.9 | 66.89 | 1117.49 | 16.71 | 114.43 | 962.32 | 8.41 | 15.01 |
| M12573 | 15511 | 104.73 | 1706.78 | 16.3 | 44.57 | 639.61 | 14.35 | 108.02 | 1439.44 | 13.33 | 14.66 |
| AV309418 | 17988 | 126.65 | 588.61 | 4.65 | 103.03 | 311.64 | 3.02 | 82.66 | 2859.45 | 34.59 | 14.09 |
| M13227 | 18619 | 1006.56 | 12533.48 | 12.45 | 819.62 | 11806.54 | 14.4 | 917.86 | 11977.63 | 13.05 | 13.30 |
| AI987929 | 17988 | 87.36 | 379.51 | 4.34 | 52.76 | 226.81 | 4.3 | 63.48 | 1953.73 | 30.78 | 13.14 |
| NM_138648 | 108078 | 13.37 | 208.34 | 15.59 | 17.29 | 351.86 | 20.35 | 30.73 | 90.09 | 2.93 | 12.96 |
| AV162459 | 68612 | 415.52 | 2065.66 | 4.97 | 60.81 | 1392.81 | 22.9 | 255.58 | 1774.24 | 6.94 | 11.60 |
| BC015076 | 14012 | 40.73 | 313.46 | 7.7 | 34.11 | 296.98 | 8.71 | 24.3 | 429.15 | 17.66 | 11.36 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AK013312 | 12442 | 490.1 | 1992.99 | 4.07 | 63.95 | 1495.86 | 23.39 | 269.59 | 1774.29 | 6.58 | 11.35 |
| BC004702 | 11799 | 400.81 | 2084.32 | 5.2 | 89.3 | 1616.32 | 18.1 | 206.75 | 2157.13 | 10.43 | 11.24 |
| M12573 | 15511 | 173.32 | 2243.94 | 12.95 | 87.83 | 778.33 | 8.86 | 170.01 | 1903.83 | 11.2 | 11.00 |
| NM_013653 | 20304 | 583.38 | 5365.47 | 9.2 | 395.69 | 6362.05 | 16.08 | 795.22 | 5396.55 | 6.79 | 10.69 |
| NM_010212 | 14200 | 73.63 | 1229.38 | 16.7 | 126.57 | 997.21 | 7.88 | 85.75 | 626.59 | 7.31 | 10.63 |
| AK009012 | 71884 | 160.41 | 2180.34 | 13.59 | 169.77 | 1960.02 | 11.54 | 143.48 | 957.14 | 6.67 | 10.60 |
| BC010581 | 100039888 /// 16765 /// 623112 | 285.63 | 1341.21 | 4.7 | 45.51 | 783.34 | 17.21 | 142.88 | 1382.81 | 9.68 | 10.53 |
| AV204216 | 242341 | 18.63 | 137.93 | 7.4 | 25.5 | 403.36 | 15.82 | 34.54 | 284.71 | 8.24 | 10.49 |
| BC015076 | 14012 | 36.83 | 251.32 | 6.82 | 32.7 | 254.87 | 7.79 | 20.29 | 339.99 | 16.76 | 10.46 |
| NM_009129 | 20254 | 15.16 | 241.74 | 15.94 | 15.53 | 157.86 | 10.16 | 16.49 | 85.08 | 5.16 | 10.42 |
| BC028507 | 21942 | 136 | 958.64 | 7.05 | 149.19 | 499.87 | 3.35 | 139.55 | 2898.97 | 20.77 | 10.39 |
| NM_026473 | 67951 | 240.2 | 1791.56 | 7.46 | 308.51 | 1937.32 | 6.28 | 207.67 | 3562.59 | 17.15 | 10.30 |
| AK017673 | 68026 | 703.37 | 3223.15 | 4.58 | 153.15 | 2589.14 | 16.91 | 421.28 | 3744.57 | 8.89 | 10.13 |
| AK009873 | 76459 | 58.98 | 903.18 | 15.31 | 54.53 | 250.94 | 4.6 | 58.27 | 607.31 | 10.42 | 10.11 |
| NM_025581 | 66468 | 52.99 | 268.85 | 5.07 | 12.21 | 206.91 | 16.95 | 33.86 | 278.11 | 8.21 | 10.08 |
| BC003738 | 19362 | 72.54 | 382.74 | 5.28 | 24.04 | 252.91 | 10.52 | 32.7 | 463.8 | 14.18 | 9.99 |
| AK002933 | 64011 | 384.24 | 4596.58 | 11.96 | 333.63 | 4493.08 | 13.47 | 432.07 | 1930.41 | 4.47 | 9.97 |
| AI987929 | 17988 | 111.9 | 463.02 | 4.14 | 106.91 | 298.43 | 2.79 | 100.56 | 2305.13 | 22.92 | 9.95 |
| AV294537 | 239650 | 263.37 | 2861.61 | 10.87 | 190.96 | 1518.64 | 7.95 | 334.61 | 3552.8 | 10.62 | 9.81 |
| C77256 | 110611 | 186.22 | 1686.15 | 9.05 | 166.14 | 1582.19 | 9.52 | 183.92 | 1919.75 | 10.44 | 9.67 |
| BE985366 | 77619 | 90.12 | 560.93 | 6.22 | 67.79 | 424.73 | 6.26 | 96.79 | 1495.3 | 15.45 | 9.31 |
| BM120925 | 12125 | 42.65 | 701.34 | 16.45 | 47.52 | 338.77 | 7.13 | 49.6 | 203.62 | 4.11 | 9.23 |
| AK017673 | 68026 | 105.53 | 598.72 | 5.67 | 39.38 | 389.28 | 9.89 | 61.16 | 731.44 | 11.96 | 9.17 |
| X75483 | 12428 | 364.43 | 1549.19 | 4.25 | 69.21 | 1015.95 | 14.68 | 204.84 | 1654.58 | 8.08 | 9.00 |
| NM_033597 | 17863 | 36.94 | 216.46 | 5.86 | 44.76 | 358.83 | 8.02 | 27.94 | 345.1 | 12.35 | 8.74 |
| NM_011613 | 21943 | 109.59 | 1750.01 | 15.97 | 275.97 | 1776.93 | 6.44 | 101.84 | 381.19 | 3.74 | 8.72 |
| NM_011617 | 21948 | 229.61 | 1813.34 | 7.9 | 107.78 | 1024.93 | 9.51 | 173.04 | 1504.58 | 8.69 | 8.70 |
| NM_010790 | 17279 | 88.81 | 558.66 | 6.29 | 26.15 | 292.55 | 11.19 | 63.72 | 532.53 | 8.36 | 8.61 |
| BC009096 | 108907 | 338.25 | 1625.69 | 4.81 | 83.68 | 1048.33 | 12.53 | 217.18 | 1795.07 | 8.27 | 8.54 |
| BC010581 | 16765 | 1589.94 | 5253.41 | 3.3 | 285.86 | 4584.76 | 16.04 | 844.7 | 5234.96 | 6.2 | 8.51 |
| BE981853 | 72309 | 105.46 | 1198.18 | 11.36 | 78.48 | 555.6 | 7.08 | 166.5 | 1180.27 | 7.09 | 8.51 |
| NM_026358 | 67749 | 52.99 | 244.07 | 4.61 | 93.3 | 110.76 | 1.19 | 54.62 | 1053.72 | 19.29 | 8.36 |
| NM_011799 | 23834 | 56.89 | 308.38 | 5.42 | 26.33 | 211.14 | 8.02 | 34.52 | 399.71 | 11.58 | 8.34 |
| X75483 | 12428 | 395.8 | 1925.18 | 4.86 | 103.47 | 1234.27 | 11.93 | 284.52 | 2247.04 | 7.9 | 8.23 |
| NM_134066 | 105349 | 105.79 | 513.48 | 4.85 | 93.6 | 598.67 | 6.4 | 119.9 | 1593.1 | 13.29 | 8.18 |
| AK010391 | 71988 | 59.77 | 253.54 | 4.24 | 11.43 | 133.49 | 11.68 | 35.39 | 294.36 | 8.32 | 8.08 |
| BG065877 | 110611 | 404.34 | 2371.57 | 5.87 | 218.1 | 1899.09 | 8.71 | 371.62 | 3582.73 | 9.64 | 8.07 |
| AK009549 | 69621 | 243.71 | 1457.61 | 5.98 | 114.55 | 1103.83 | 9.64 | 231.17 | 1962.67 | 8.49 | 8.04 |
| BB356493 | 654795 | 107.58 | 846.26 | 7.87 | 160.05 | 1622.31 | 10.14 | 117.17 | 667.05 | 5.69 | 7.90 |
| NM_008479 | 16768 | 145.86 | 1046.69 | 7.18 | 138.03 | 1210.26 | 8.77 | 232.45 | 1652.41 | 7.11 | 7.69 |
| BE979441 | 330662 | 259.22 | 1501.19 | 5.79 | 180.93 | 1288.54 | 7.12 | 231.44 | 2247.66 | 9.71 | 7.54 |
| NM_008681 | 17988 | 193 | 691.02 | 3.58 | 202.57 | 552.85 | 2.73 | 194.3 | 3129.69 | 16.11 | 7.47 |
| D87867 | 22236 /// 394430 /// 394432 /// 394433 /// 394434 /// 394435 /// 394436 /// 94284 | 103.38 | 637.31 | 6.17 | 80.92 | 987.9 | 12.21 | 114.37 | 413.07 | 3.61 | 7.33 |
| AK011162 | 72107 | 21.57 | 129.32 | 6 | 11.23 | 83.08 | 7.4 | 16.98 | 140.55 | 8.28 | 7.23 |
| AV332575 | 70564 | 141.07 | 1117.27 | 7.92 | 120.96 | 843.29 | 6.97 | 115.35 | 756.49 | 6.56 | 7.15 |
| NM_009104 | 20135 | 261.79 | 1316.88 | 5.03 | 84.37 | 546.76 | 6.48 | 159.92 | 1531.79 | 9.58 | 7.03 |
| BB702047 | 52276 | 248.32 | 1058.73 | 4.26 | 64.89 | 680.43 | 10.49 | 154.01 | 953.59 | 6.19 | 6.98 |
| BC019755 | 213696 | 266.1 | 2191.29 | 8.23 | 308.32 | 1938.47 | 6.29 | 192.91 | 1218.64 | 6.32 | 6.95 |
| AU015121 | 268697 | 311.47 | 1320.63 | 4.24 | 62.93 | 668.42 | 10.62 | 211.69 | 1211.51 | 5.72 | 6.86 |
| BC003738 | 19362 | 32.48 | 197.24 | 6.07 | 16.89 | 126.7 | 7.5 | 32.22 | 219.85 | 6.82 | 6.80 |
| BB667581 | 12125 | 101.08 | 1212.68 | 12 | 128.43 | 592.15 | 4.61 | 102.45 | 350.73 | 3.42 | 6.68 |
| NM_080853 | 140919 | 547.69 | 2798.74 | 5.11 | 103.84 | 984.82 | 9.48 | 386.53 | 2088.4 | 5.4 | 6.66 |
| AK006467 | 75568 | 38.97 | 234.43 | 6.02 | 38.7 | 239.93 | 6.2 | 33.68 | 251.2 | 7.46 | 6.56 |
| NM_009127 | 20249 | 83.01 | 307.56 | 3.7 | 84.01 | 539.87 | 6.43 | 50.59 | 481.41 | 9.52 | 6.55 |
| NM_010555 | 16178 | 220.2 | 1421.28 | 6.45 | 660.3 | 2809.92 | 4.26 | 213.37 | 1889.76 | 8.86 | 6.52 |
| NM_011369 | 20419 | 121.86 | 709.24 | 5.82 | 58.76 | 307.36 | 5.23 | 87.15 | 736.33 | 8.45 | 6.50 |
| NM_007669 | 12575 | 654.48 | 3378.26 | 5.16 | 697.59 | 2253.54 | 3.23 | 393.85 | 4366.21 | 11.09 | 6.49 |
| NM_010373 | 14942 | 131.1 | 520.52 | 3.97 | 254.26 | 2076.29 | 8.17 | 109.3 | 790.59 | 7.23 | 6.46 |
| NM_009104 | 20135 | 326.79 | 1684.91 | 5.16 | 115.63 | 720.92 | 6.23 | 230.46 | 1806.55 | 7.84 | 6.41 |
| BQ180367 | 140919 | 668.86 | 4182.56 | 6.25 | 199.3 | 1525.01 | 7.65 | 562.26 | 2955.6 | 5.26 | 6.39 |
| NM_019631 | 56277 | 97.93 | 434.43 | 4.43 | 49.54 | 96.71 | 1.95 | 73.28 | 936.83 | 12.78 | 6.39 |
| AV301324 | 20135 | 643.82 | 2928.78 | 4.55 | 193.86 | 1168.64 | 6.03 | 350.97 | 3006.49 | 8.57 | 6.38 |
| AK010351 | 66977 | 134.31 | 633.64 | 4.72 | 36.39 | 249.61 | 6.86 | 85.79 | 649.26 | 7.57 | 6.38 |
| BC018397 | 12904 | 79.73 | 473.88 | 5.94 | 65.82 | 303.95 | 4.62 | 71.5 | 611.36 | 8.55 | 6.37 |
| AV251613 | 97086 | 33.44 | 234.53 | 7.01 | 39.8 | 221.31 | 5.56 | 39.1 | 252.86 | 6.47 | 6.35 |
| AF450241 | 171285 | 742.48 | 2936.35 | 3.95 | 162.98 | 1564.93 | 9.6 | 514.93 | 2780.8 | 5.4 | 6.32 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| BC027121 | 66442 | 202.22 | 893.22 | 4.42 | 71.03 | 470.33 | 6.62 | 113.65 | 889.74 | 7.83 | 6.29 |
| NM_007659 | 12534 | 523.86 | 1793.76 | 3.42 | 122.12 | 1093.38 | 8.95 | 301.74 | 1938.8 | 6.43 | 6.27 |
| NM_007629 | 12429 /// 268697 /// 434175 /// 667005 | 164.48 | 661.2 | 4.02 | 33.14 | 315.55 | 9.52 | 111.41 | 566.16 | 5.08 | 6.21 |
| AB032771 | 21943 | 103.06 | 956.93 | 9.29 | 149.31 | 899 | 6.02 | 79.46 | 262.5 | 3.3 | 6.20 |
| AY083458 | 235505 | 115.89 | 656.57 | 5.67 | 35.14 | 216.08 | 6.15 | 139.05 | 936.58 | 6.74 | 6.19 |
| NM_009127 | 20249 | 153.48 | 563.53 | 3.67 | 134.68 | 772.61 | 5.74 | 121.44 | 1085.82 | 8.94 | 6.12 |
| AF032460 | 12125 | 44.82 | 346.31 | 7.73 | 31.54 | 208.29 | 6.6 | 33.85 | 134.56 | 3.98 | 6.10 |
| BI081061 | 14793 | 285.63 | 1212.94 | 4.25 | 135.14 | 1064.1 | 7.87 | 209.58 | 1275.22 | 6.08 | 6.07 |
| AK018120 | 70727 | 22.14 | 235.21 | 10.63 | 16.39 | 77.13 | 4.71 | 27.56 | 73.73 | 2.68 | 6.01 |
| NM_011234 | 19361 | 187.22 | 822.96 | 4.4 | 71.59 | 380.27 | 5.31 | 119.49 | 992.27 | 8.3 | 6.00 |
| NM_023209 | 52033 | 149.65 | 629.07 | 4.2 | 46.98 | 293.25 | 6.24 | 77.43 | 584.91 | 7.55 | 6.00 |
| BB375974 | 80752 | 24.28 | 133.21 | 5.49 | 21.54 | 222.77 | 10.34 | 36.27 | 78 | 2.15 | 5.99 |
| AK014919 | 66336 | 51.39 | 298.93 | 5.82 | 36.02 | 259.75 | 7.21 | 57.28 | 280.34 | 4.89 | 5.97 |
| BB702754 | 18140 | 152.44 | 635.09 | 4.17 | 51.85 | 418.46 | 8.07 | 135.16 | 763.42 | 5.65 | 5.96 |
| BC019946 | 11910 | 135.01 | 551.19 | 4.08 | 221.82 | 1560.81 | 7.04 | 127.55 | 861.08 | 6.75 | 5.96 |
| NM_010558 | 16191 | 293.56 | 907.63 | 3.09 | 62.96 | 99.57 | 1.58 | 178.49 | 2302.56 | 12.9 | 5.86 |
| NM_009004 | 19348 | 69.7 | 387.85 | 5.56 | 27.71 | 144.25 | 5.21 | 54.25 | 367.05 | 6.77 | 5.85 |
| BB758432 | 330938 | 58.12 | 238.71 | 4.11 | 22.1 | 61.3 | 2.77 | 72.05 | 756.32 | 10.5 | 5.79 |
| AF079222 | 15366 | 64.93 | 343.18 | 5.29 | 36.41 | 159.42 | 4.38 | 51.83 | 398.54 | 7.69 | 5.79 |
| BC005799 | 76131 | 52.48 | 331.47 | 6.32 | 20.56 | 134.17 | 6.53 | 52.15 | 221.64 | 4.25 | 5.70 |
| AI266795 | 20193 | 129.19 | 769.6 | 5.96 | 167.03 | 772.77 | 4.63 | 135.34 | 844.69 | 6.24 | 5.61 |
| NM_010373 | 14942 | 154.2 | 501.86 | 3.25 | 280.61 | 1951.09 | 6.95 | 114.74 | 759.38 | 6.62 | 5.61 |
| AF002823 | 12235 | 127.53 | 521.08 | 4.09 | 53.1 | 277.79 | 5.23 | 93.8 | 703.2 | 7.5 | 5.61 |
| AK017688 | 70564 | 357.22 | 2074.29 | 5.81 | 299.33 | 1658.12 | 5.54 | 326.1 | 1769.95 | 5.43 | 5.59 |
| AA986082 | 73710 | 55.28 | 224.04 | 4.05 | 84.36 | 216.47 | 2.57 | 36.42 | 366.78 | 10.07 | 5.56 |
| AF181829 | 56193 | 169.67 | 663.63 | 3.91 | 78.35 | 691.32 | 8.82 | 170.92 | 674.32 | 3.95 | 5.56 |
| AF181829 | 56193 | 99.78 | 436.09 | 4.37 | 51.65 | 411.88 | 7.97 | 100.38 | 435.71 | 4.34 | 5.56 |
| AV132173 | 12615 | 382.48 | 1705.09 | 4.46 | 160.76 | 1346.28 | 8.37 | 314.95 | 1198.37 | 3.8 | 5.54 |
| BC005773 | 26558 | 61.33 | 216.63 | 3.53 | 47.82 | 204.31 | 4.27 | 44.22 | 389.48 | 8.81 | 5.54 |
| NM_011182 | 19159 | 64.08 | 729.63 | 11.39 | 200.3 | 543.55 | 2.71 | 68.77 | 171.94 | 2.5 | 5.53 |
| AK007630 | 12575 | 576.19 | 3112.8 | 5.4 | 852.89 | 2146.96 | 2.52 | 487.14 | 4120.42 | 8.46 | 5.46 |
| NM_016900 | 12390 | 275.34 | 1377.31 | 5 | 218.04 | 1028.07 | 4.71 | 247.57 | 1646.46 | 6.65 | 5.45 |
| NM_009647 | 100047616 /// 11639 | 111.03 | 244.55 | 2.2 | 79.07 | 92.72 | 1.17 | 95.85 | 1236.26 | 12.9 | 5.42 |
| BC003261 | 20877 | 134.54 | 578.16 | 4.3 | 57.3 | 327.17 | 5.71 | 128.34 | 781.35 | 6.09 | 5.37 |
| NM_007629 | 12429 /// 268697 | 233.48 | 863.03 | 3.7 | 86.74 | 632.05 | 7.29 | 151.2 | 754.06 | 4.99 | 5.33 |
| AF079222 | 15366 | 51.38 | 317.21 | 6.17 | 19.68 | 94.13 | 4.78 | 50.98 | 254.78 | 5 | 5.32 |
| C77054 | 18005 | 148.22 | 566.54 | 3.82 | 59.48 | 432.43 | 7.27 | 104.8 | 503.06 | 4.8 | 5.30 |
| NM_007691 | 12649 | 34.73 | 209.75 | 6.04 | 27.09 | 95.35 | 3.52 | 32.09 | 203.18 | 6.33 | 5.30 |
| BI794748 | 230259 | 86.29 | 532.49 | 6.17 | 167.4 | 727.36 | 4.34 | 112.41 | 601.24 | 5.35 | 5.29 |
| BB703394 | | 47.36 | 185.52 | 3.92 | 70.98 | 593.83 | 8.37 | 57.74 | 203.46 | 3.52 | 5.27 |
| AK010477 | 69745 | 658.21 | 3244.24 | 4.93 | 415.69 | 2540.46 | 6.11 | 568.21 | 2699.31 | 4.75 | 5.26 |
| NM_009707 | 11856 | 22.39 | 124.25 | 5.55 | 10.59 | 43.27 | 4.09 | 22.53 | 137.43 | 6.1 | 5.25 |
| NM_009760 | 12176 | 833.25 | 2306.52 | 2.77 | 587.18 | 886.04 | 1.51 | 600.54 | 6848.94 | 11.4 | 5.23 |
| NM_012057 | 27056 | 160.55 | 1072.57 | 6.68 | 109.64 | 369.9 | 3.37 | 233.05 | 1300.13 | 5.58 | 5.21 |
| BG060909 | 20250 | 428.25 | 1305.05 | 3.05 | 460.04 | 1107.78 | 2.41 | 358.99 | 3643.45 | 10.15 | 5.20 |
| NM_033597 | 17863 | 58.16 | 269.49 | 4.63 | 82.37 | 419.35 | 5.09 | 75 | 429.94 | 5.73 | 5.15 |
| BC003261 | 20877 | 126.58 | 459.97 | 3.63 | 39.52 | 230.56 | 5.83 | 96.12 | 555.56 | 5.78 | 5.08 |
| NM_009741 | 100046608 /// 12043 | 149.06 | 922.54 | 6.19 | 218.84 | 973.19 | 4.45 | 184.66 | 845.05 | 4.58 | 5.07 |
| NM_133888 | 100340 | 269.5 | 1473.26 | 5.47 | 214.19 | 1171.54 | 5.47 | 278.26 | 1174.95 | 4.22 | 5.05 |
| NM_016851 | 54139 | 73.8 | 326.02 | 4.42 | 60.6 | 413.6 | 6.83 | 49.4 | 188.74 | 3.82 | 5.02 |
| NM_009014 | 19363 | 61.66 | 287.21 | 4.66 | 53.04 | 285.79 | 5.39 | 50.17 | 251.05 | 5 | 5.02 |
| BB041150 | 107995 | 467.25 | 1746.69 | 3.74 | 138.32 | 920.52 | 6.65 | 292.06 | 1330.31 | 4.55 | 4.98 |
| BB463610 | 74041 | 64.78 | 280.92 | 4.34 | 61.27 | 187.95 | 3.07 | 40.61 | 298.88 | 7.36 | 4.92 |
| AF032969 | | 27.64 | 160.53 | 5.81 | 35.35 | 162.81 | 4.61 | 31.07 | 133.91 | 4.31 | 4.91 |
| AV084342 | 654824 | 193.07 | 507.23 | 2.63 | 74.93 | 106.64 | 1.42 | 174.24 | 1854.31 | 10.64 | 4.90 |
| AV224521 | 227753 | 504.64 | 1292.45 | 2.56 | 397.19 | 985.5 | 2.48 | 382.53 | 3640.68 | 9.52 | 4.85 |
| BM250782 | 21942 | 354.82 | 1548.21 | 4.36 | 418.65 | 1032.68 | 2.47 | 470.1 | 3625.74 | 7.71 | 4.85 |
| AA709993 | 20365 | 89.93 | 345.76 | 3.84 | 58.77 | 355.27 | 6.04 | 70.99 | 327.4 | 4.61 | 4.83 |
| BB408123 | 66214 | 44.38 | 158.78 | 3.58 | 78.2 | 345.34 | 4.42 | 40.69 | 262.38 | 6.45 | 4.82 |
| BI731319 | 23969 | 44.37 | 346.19 | 7.8 | 51.5 | 246.35 | 4.78 | 51.3 | 92.14 | 1.8 | 4.79 |
| BC019416 | 94346 | 104.43 | 475.81 | 4.56 | 95.46 | 434.58 | 4.55 | 102.19 | 531.11 | 5.2 | 4.77 |
| X64550 | 15366 | 83.03 | 442.5 | 5.33 | 48.14 | 181.94 | 3.78 | 78.67 | 408.55 | 5.19 | 4.77 |
| BG060909 | 20250 | 135.92 | 395.57 | 2.91 | 111.62 | 288.74 | 2.59 | 114.14 | 997.74 | 8.74 | 4.75 |
| BB497312 | 114644 | 85.76 | 279.09 | 3.25 | 73.61 | 326.75 | 4.44 | 85.39 | 556.34 | 6.52 | 4.74 |
| AK010166 | 71934 | 39.79 | 180.41 | 4.53 | 33.6 | 200.49 | 5.97 | 45.28 | 166.57 | 3.68 | 4.73 |
| BB827235 | 16551 | 102.37 | 428.5 | 4.19 | 58.45 | 244.1 | 4.18 | 69.27 | 399.73 | 5.77 | 4.71 |
| BB100249 | 19734 | 290.68 | 1034.96 | 3.56 | 312.77 | 2444.97 | 7.82 | 287.14 | 769.47 | 2.68 | 4.69 |
| AV307110 | 52276 | 243.71 | 839.6 | 3.45 | 97.67 | 563.34 | 5.77 | 178.02 | 856.73 | 4.81 | 4.68 |
| BM120925 | 12125 | 100.34 | 893.96 | 8.91 | 109.98 | 321.17 | 2.92 | 121.24 | 261.75 | 2.16 | 4.66 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AF004023 | 17470 | 540.63 | 2623.9 | 4.85 | 364.26 | 1805.23 | 4.96 | 494.9 | 2037.46 | 4.12 | 4.64 |
| BC016135 | 14697 | 213.79 | 1156.12 | 5.41 | 172.76 | 777.31 | 4.5 | 176.91 | 711.47 | 4.02 | 4.64 |
| AA197362 | 70466 | 177.07 | 727.74 | 4.11 | 84.22 | 392 | 4.65 | 136.2 | 700.24 | 5.14 | 4.63 |
| AW763765 | 193740 | 45.76 | 227.35 | 4.97 | 37.81 | 136.79 | 3.62 | 48.26 | 254.38 | 5.27 | 4.62 |
| NM_016904 | 54124 | 410.15 | 1540.06 | 3.75 | 239.83 | 1161.3 | 4.84 | 271.69 | 1413.88 | 5.2 | 4.60 |
| BM234447 | 16551 | 153.6 | 574.81 | 3.74 | 56.65 | 258.16 | 4.56 | 113.73 | 605.07 | 5.32 | 4.54 |
| BC006674 | 70385 | 103.38 | 437.72 | 4.23 | 60.65 | 204.88 | 3.38 | 78.23 | 470.2 | 6.01 | 4.54 |
| NM_025569 | 66447 | 295.5 | 969.39 | 3.28 | 182.7 | 694.87 | 3.8 | 239.61 | 1544.81 | 6.45 | 4.51 |
| NM_007997 | 14149 | 158.7 | 424.97 | 2.68 | 103.17 | 439.81 | 4.26 | 132.8 | 872.06 | 6.57 | 4.50 |
| AK005016 | 15473 | 221.47 | 1032.66 | 4.66 | 228.13 | 1234.12 | 5.41 | 232.4 | 789.59 | 3.4 | 4.49 |
| AK006234 | 66336 | 70.06 | 263.09 | 3.76 | 41.86 | 201.62 | 4.82 | 51.07 | 249.96 | 4.89 | 4.49 |
| BB559293 | 71653 | 114.78 | 520.15 | 4.53 | 87.93 | 321.95 | 3.66 | 108.46 | 566.92 | 5.23 | 4.47 |
| NM_026410 | 67849 | 122.54 | 436.02 | 3.56 | 76.61 | 360.27 | 4.7 | 106.33 | 525.3 | 4.94 | 4.40 |
| BQ176550 | 320051 | 118.89 | 647.54 | 5.45 | 80.05 | 422.86 | 5.28 | 80.07 | 197.04 | 2.46 | 4.40 |
| BI685685 | 68667 | 212.07 | 1108.62 | 5.23 | 145.12 | 580.73 | 4 | 226.01 | 874.32 | 3.87 | 4.37 |
| L21027 | 236539 /// 666422 /// 666875 /// 668576 /// 675010 /// 675316 /// 675710 /// 677380 | 640.09 | 2382.79 | 3.72 | 465.99 | 1958.33 | 4.2 | 597.72 | 3036.47 | 5.08 | 4.33 |
| BB789822 | 230259 | 124.11 | 509.37 | 4.1 | 130.79 | 537.03 | 4.11 | 123.55 | 571.2 | 4.62 | 4.28 |
| AF128218 | 20303 | 240.46 | 920.37 | 3.83 | 121.03 | 414.29 | 3.42 | 301.14 | 1675.4 | 5.56 | 4.27 |
| BI247584 | 110196 | 545.09 | 1164.39 | 2.14 | 306.51 | 900 | 2.94 | 351.44 | 2704.67 | 7.7 | 4.26 |
| W91024 | 319171 /// 665433 | 2363.54 | 7436.12 | 3.15 | 986.7 | 5295.56 | 5.37 | 2493.49 | 10521.67 | 4.22 | 4.25 |
| BB348062 | 56175 | 406.52 | 1764.96 | 4.34 | 244.57 | 1498.23 | 6.13 | 489.29 | 1095.77 | 2.24 | 4.24 |
| NM_016904 | 54124 | 1173.19 | 3958.65 | 3.37 | 728.09 | 3703.09 | 5.09 | 918.9 | 3877.33 | 4.22 | 4.23 |
| BC004827 | 107272 | 378.53 | 1416.33 | 3.74 | 255.66 | 1036.86 | 4.06 | 377.66 | 1838.69 | 4.87 | 4.22 |
| AK011615 | 71517 | 204.04 | 747.11 | 3.66 | 180.89 | 623.34 | 3.45 | 165.14 | 918.46 | 5.56 | 4.22 |
| NM_011524 | 21335 | 76.16 | 305.65 | 4.01 | 42.88 | 189.93 | 4.43 | 73.44 | 309.16 | 4.21 | 4.22 |
| AV025667 | 227753 | 450.34 | 1111.85 | 2.47 | 351.38 | 865.46 | 2.46 | 383.14 | 2949.81 | 7.7 | 4.21 |
| AF059567 | 12579 | 85.19 | 493.6 | 5.79 | 91.66 | 286.72 | 3.13 | 90.52 | 328.43 | 3.63 | 4.18 |
| U31625 | 12189 | 81.17 | 265.03 | 3.26 | 49.43 | 215.16 | 4.35 | 60.89 | 300.63 | 4.94 | 4.18 |
| AU045529 | 12236 | 102.96 | 468.02 | 4.55 | 49.89 | 171.58 | 3.44 | 86.27 | 389.03 | 4.51 | 4.17 |
| BB810450 | 22042 | 96.21 | 312.94 | 3.25 | 68.79 | 192.27 | 2.79 | 89.29 | 574.74 | 6.44 | 4.16 |
| D87867 | 22236 /// 394430 /// 394432 /// 394433 /// 394434 /// 394435 /// 394436 /// 94284 | 61.68 | 262.65 | 4.26 | 64.04 | 365.01 | 5.7 | 67.3 | 166.53 | 2.47 | 4.14 |
| BE628614 | 11746 | 210.55 | 720.22 | 3.42 | 119.29 | 509.24 | 4.27 | 148.6 | 699.53 | 4.71 | 4.13 |
| AA144045 | 20361 | 213.05 | 1439.52 | 6.76 | 196.4 | 575.56 | 2.93 | 205.44 | 555.14 | 2.7 | 4.13 |
| BB017021 | 242126 | 167.59 | 473.19 | 2.82 | 184.16 | 594.45 | 3.23 | 157.65 | 999.91 | 6.34 | 4.13 |
| BC021795 | 217845 | 167.24 | 522.49 | 3.12 | 158.54 | 947.87 | 5.98 | 168.74 | 551.17 | 3.27 | 4.12 |
| U80932 | 20878 | 146.94 | 525.03 | 3.57 | 80.32 | 279.66 | 3.48 | 105.36 | 555.88 | 5.28 | 4.11 |
| AI987929 | 17988 | 240.73 | 477.73 | 1.98 | 229.7 | 373.89 | 1.63 | 229.36 | 1995.68 | 8.7 | 4.10 |
| AK017038 | 71314 | 53.31 | 225.08 | 4.22 | 66.49 | 254.62 | 3.83 | 61 | 259.34 | 4.25 | 4.10 |
| C85740 | 12649 | 57.03 | 223.45 | 3.92 | 40.76 | 120.04 | 2.95 | 45.14 | 242.19 | 5.37 | 4.08 |
| AK004655 | 74107 | 267.88 | 863.89 | 3.22 | 79.94 | 354.56 | 4.44 | 169.53 | 772.95 | 4.56 | 4.07 |
| AV246882 | 235505 | 203.69 | 758.43 | 3.72 | 83.99 | 299.11 | 3.56 | 214.25 | 1053.75 | 4.92 | 4.07 |
| BC024131 | 211401 | 89.38 | 472.67 | 5.29 | 132.1 | 342.92 | 2.6 | 74.55 | 320.27 | 4.3 | 4.06 |
| AK011596 | 22042 | 701.42 | 2688.9 | 3.83 | 792.62 | 2091.17 | 2.64 | 904.52 | 5146.5 | 5.69 | 4.05 |
| NM_008350 | 16156 | 103.3 | 417.11 | 4.04 | 96.56 | 522 | 5.41 | 115.97 | 312.84 | 2.7 | 4.05 |
| BC025084 | 26886 | 69.52 | 255.61 | 3.68 | 42.54 | 176.69 | 4.15 | 58.1 | 248.48 | 4.28 | 4.04 |
| BE133150 | 68763 | 335.13 | 1463.88 | 4.37 | 381.39 | 1835.35 | 4.81 | 466.84 | 1358.7 | 2.91 | 4.03 |
| NM_023044 | 65221 | 357.08 | 1590.24 | 4.45 | 262.71 | 1310.09 | 4.99 | 333.31 | 879.47 | 2.64 | 4.03 |
| BC002008 | 16592 | 566.53 | 1934.44 | 3.41 | 662.73 | 1668.11 | 2.52 | 740.53 | 4554.08 | 6.15 | 4.03 |
| AK011178 | 72446 | 62.59 | 409.86 | 6.55 | 68.91 | 164.55 | 2.39 | 64.79 | 203.17 | 3.14 | 4.03 |
| AK002512 | 66060 | 161.92 | 521.48 | 3.22 | 210.78 | 637.56 | 3.02 | 179.11 | 1043.07 | 5.82 | 4.02 |
| AK010336 | 69716 | 166.36 | 574.63 | 3.45 | 153 | 480.44 | 3.14 | 112.1 | 612.87 | 5.47 | 4.02 |
| NM_008360 | 16173 | 280.86 | 821.02 | 2.92 | 149.66 | 715.05 | 4.78 | 266.31 | 1154.9 | 4.34 | 4.01 |
| AA796766 | 17750 | 1087.16 | 2915.37 | 2.68 | 3161.08 | 3931.66 | 1.24 | 1104.59 | 8925.99 | 8.08 | 4.00 |
| AK011311 | 72119 | 137.88 | 461.24 | 3.35 | 51.13 | 201.46 | 3.94 | 103.12 | 482.25 | 4.68 | 3.99 |
| NM_009502 | 22330 | 334.04 | 1178.91 | 3.53 | 290.43 | 1446.95 | 4.98 | 336.02 | 1151.87 | 3.43 | 3.98 |
| BC021499 | 215387 | 119.24 | 383.92 | 3.22 | 47.58 | 219.45 | 4.61 | 105.44 | 428.7 | 4.07 | 3.97 |
| BI739725 | 72895 | 315.65 | 1548.91 | 4.91 | 438.74 | 1529.33 | 3.49 | 409.75 | 1421.13 | 3.47 | 3.96 |
| BC011513 | 17863 | 39.37 | 115.91 | 2.94 | 44.23 | 182.15 | 4.12 | 39.48 | 183.13 | 4.64 | 3.90 |
| BG060909 | 20250 | 1539.33 | 3842.55 | 2.5 | 2363.91 | 3734.68 | 1.58 | 1161.75 | 8809.89 | 7.58 | 3.89 |
| AV213379 | 67041 | 325.66 | 1294.59 | 3.98 | 201.81 | 1039.35 | 5.15 | 449.88 | 1098.42 | 2.44 | 3.86 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AF177664 | 11856 | 193.85 | 659.05 | 3.4 | 81.1 | 230.02 | 2.84 | 151.31 | 804.29 | 5.32 | 3.85 |
| X17502 | 12035 | 84.51 | 298.11 | 3.53 | 77.44 | 274.57 | 3.55 | 99.83 | 447.65 | 4.48 | 3.85 |
| BC014865 | 67103 | 150.27 | 440.07 | 2.93 | 68.26 | 289.83 | 4.25 | 128.44 | 556.16 | 4.33 | 3.84 |
| AK019534 | 12745 | 96.84 | 309.32 | 3.19 | 69.11 | 261.35 | 3.78 | 73.73 | 333.03 | 4.52 | 3.83 |
| NM_010892 | 18005 | 63.04 | 224.08 | 3.55 | 40.82 | 161.52 | 3.96 | 46.6 | 185.17 | 3.97 | 3.83 |
| AJ294535 | 14768 | 1447.91 | 4607.84 | 3.18 | 799.56 | 3288.18 | 4.11 | 1139.65 | 4761.93 | 4.18 | 3.82 |
| AK009744 | 56405 | 237.39 | 676.3 | 2.85 | 409.09 | 2195.48 | 5.37 | 256.32 | 830.14 | 3.24 | 3.82 |
| L07264 | 15200 | 62.51 | 204.37 | 3.27 | 65.63 | 309.27 | 4.71 | 75.37 | 260.11 | 3.45 | 3.81 |
| BE986864 | 26909 | 39.97 | 146.94 | 3.68 | 35.39 | 53.98 | 1.53 | 26.29 | 161.73 | 6.15 | 3.79 |
| BM120495 | 52398 | 381.42 | 1196.3 | 3.14 | 242.41 | 858.94 | 3.54 | 305.27 | 1426.86 | 4.67 | 3.78 |
| AV208528 |  | 89.9 | 328.47 | 3.65 | 132.39 | 238.55 | 1.8 | 92.6 | 545.22 | 5.89 | 3.78 |
| AV035110 | 121022 | 779.6 | 3025.25 | 3.88 | 436.09 | 1814.18 | 4.16 | 738.39 | 2385.35 | 3.23 | 3.76 |
| BB043558 | 414108 | 77.4 | 309.39 | 4 | 38.65 | 117.45 | 3.04 | 62.26 | 262.42 | 4.22 | 3.75 |
| AF424701 | 216560 | 115.78 | 464.55 | 4.01 | 84.18 | 340.7 | 4.05 | 204.21 | 650.28 | 3.18 | 3.75 |
| NM_023223 | 107995 | 353.42 | 1001.05 | 2.83 | 157 | 580.3 | 3.7 | 210.23 | 984.89 | 4.68 | 3.74 |
| AV024771 | 211401 | 309.77 | 1368.49 | 4.42 | 546.36 | 1137.88 | 2.08 | 236.17 | 1105.78 | 4.68 | 3.73 |
| BB559878 | 11534 | 103.55 | 353.93 | 3.42 | 120.11 | 511.29 | 4.26 | 135.26 | 466.16 | 3.45 | 3.71 |
| AW986176 | 71819 | 231.26 | 616.41 | 2.67 | 108.61 | 543.33 | 5 | 171.42 | 592.18 | 3.45 | 3.71 |
| BB030680 | 30926 /// 620016 | 164.78 | 646.46 | 3.92 | 177.24 | 682.06 | 3.85 | 209.19 | 698.58 | 3.34 | 3.70 |
| BB865814 | 67501 | 309.31 | 845.2 | 2.73 | 168.85 | 891.43 | 5.28 | 239.52 | 741.17 | 3.09 | 3.70 |
| BC027271 | 121022 | 814.62 | 2600.64 | 3.19 | 329.73 | 1526.98 | 4.63 | 724.33 | 2366.86 | 3.27 | 3.70 |
| NM_009904 | 12745 | 219.65 | 661.8 | 3.01 | 142.67 | 548.39 | 3.84 | 163.45 | 692.25 | 4.24 | 3.70 |
| NM_021790 | 60411 | 110.41 | 427.48 | 3.87 | 110.97 | 311.1 | 2.8 | 97.4 | 430.89 | 4.42 | 3.70 |
| BF577722 | 67629 | 97.26 | 319.33 | 3.28 | 69.61 | 241.62 | 3.47 | 93.3 | 398.06 | 4.27 | 3.67 |
| AV211098 | 207175 | 327.25 | 1064.6 | 3.25 | 279.99 | 1152.9 | 4.12 | 323.46 | 1171.29 | 3.62 | 3.66 |
| AK005954 | 71846 | 280.81 | 668.03 | 2.38 | 263.63 | 501.18 | 1.9 | 211 | 1415.68 | 6.71 | 3.66 |
| AI606403 | 76594 | 259.19 | 708.63 | 2.73 | 154.06 | 704.09 | 4.57 | 215.09 | 764.86 | 3.56 | 3.62 |
| BC004801 | 319554 | 219.8 | 574.81 | 2.62 | 174.79 | 354.66 | 2.03 | 171.02 | 1058.1 | 6.19 | 3.61 |
| W34859 | 239555 | 288.13 | 1051.65 | 3.65 | 315.76 | 912.47 | 2.89 | 304.67 | 1305.44 | 4.28 | 3.61 |
| NM_007984 | 14086 | 408.28 | 1182.65 | 2.9 | 521.17 | 1203.82 | 2.31 | 354.56 | 1983.04 | 5.59 | 3.60 |
| AV216491 | 107272 | 425.5 | 1273.39 | 2.99 | 374.21 | 1138.48 | 3.04 | 356.53 | 1700.13 | 4.77 | 3.60 |
| NM_026613 | 68201 | 136.98 | 407.38 | 2.97 | 70.73 | 316.46 | 4.47 | 121.48 | 402.14 | 3.31 | 3.58 |
| NM_007971 | 14056 | 516.52 | 1390.65 | 2.69 | 159.85 | 896.33 | 5.61 | 637 | 1545.67 | 2.43 | 3.58 |
| NM_133655 | 12520 | 56.71 | 209.66 | 3.7 | 133.66 | 310.05 | 2.32 | 66.67 | 312.97 | 4.69 | 3.57 |
| BB810450 | 22042 | 289 | 868.69 | 3.01 | 277.85 | 687.29 | 2.47 | 311.62 | 1618.45 | 5.19 | 3.56 |
| BI134269 | 103203 | 101.55 | 354.01 | 3.49 | 89.76 | 260.96 | 2.91 | 82.85 | 353.19 | 4.26 | 3.55 |
| AK013095 | 69263 | 249.76 | 837.63 | 3.35 | 463.38 | 1210.53 | 2.61 | 236.88 | 1095.66 | 4.63 | 3.53 |
| BC022752 | 56857 | 509.63 | 1990.11 | 3.91 | 297.97 | 1029.34 | 3.45 | 478.18 | 1536.21 | 3.21 | 3.52 |
| NM_030690 | 75646 | 295.91 | 981.38 | 3.32 | 208.82 | 986.04 | 4.72 | 213.38 | 535.25 | 2.51 | 3.52 |
| BB702347 | 54392 | 337.59 | 985.73 | 2.92 | 154.67 | 534.64 | 3.46 | 232.7 | 966.72 | 4.15 | 3.51 |
| NM_013750 | 27280 | 166.82 | 499.25 | 2.99 | 158.38 | 474.82 | 3 | 150.4 | 681.27 | 4.53 | 3.51 |
| BC013542 | 67182 | 144.44 | 620.58 | 4.3 | 162.52 | 648.83 | 3.99 | 125.49 | 279.73 | 2.23 | 3.51 |
| AK012148 | 51944 | 115.29 | 402.37 | 3.49 | 61.25 | 243.47 | 3.98 | 97.5 | 295.57 | 3.03 | 3.50 |
| AV033355 | 101490 | 53.85 | 302.8 | 5.62 | 78.84 | 193.25 | 2.45 | 83.45 | 203.18 | 2.43 | 3.50 |
| NM_023422 | 68024 | 571.26 | 2076.96 | 3.64 | 836.67 | 2038.77 | 2.44 | 525.71 | 2310.07 | 4.39 | 3.49 |
| BI739353 | 29858 | 258.98 | 915.88 | 3.54 | 401.72 | 938.69 | 2.34 | 201.24 | 918.58 | 4.56 | 3.48 |
| BB787809 | 21335 | 174.86 | 543.62 | 3.11 | 136.78 | 418.74 | 3.06 | 119.54 | 510.74 | 4.27 | 3.48 |
| BB445036 | 14064 | 89.48 | 199.18 | 2.23 | 9.86 | 58.11 | 5.9 | 58.58 | 134.92 | 2.3 | 3.48 |
| AY090098 | 76933 | 2972.78 | 10550.74 | 3.55 | 2834.4 | 12962.61 | 4.57 | 4171.64 | 9590.52 | 2.3 | 3.47 |
| NM_007793 | 13014 | 1060.75 | 3016.46 | 2.84 | 820.27 | 3555.26 | 4.33 | 1125.74 | 3641.32 | 3.23 | 3.47 |
| BM200578 | 105988 | 98.94 | 246.45 | 2.49 | 48.59 | 163.88 | 3.37 | 71.88 | 325.43 | 4.53 | 3.46 |
| BB224405 | 20778 | 52.04 | 126.63 | 2.43 | 46.14 | 117.9 | 2.56 | 49.43 | 265.44 | 5.37 | 3.45 |
| BB144704 | 11303 | 157.06 | 528.84 | 3.37 | 149.49 | 381.02 | 2.55 | 153.48 | 678.31 | 4.42 | 3.45 |
| BB407702 | 319707 | 68.7 | 280.22 | 4.08 | 84.05 | 245.66 | 2.92 | 86.87 | 289.28 | 3.33 | 3.44 |
| NM_009132 | 20259 | 37.92 | 159.79 | 4.21 | 57.38 | 154.79 | 2.7 | 42.8 | 146.29 | 3.42 | 3.44 |
| AV270035 | 76843 | 131.27 | 399.77 | 3.05 | 94.81 | 346.75 | 3.66 | 102.25 | 368.43 | 3.6 | 3.44 |
| BG083485 | 20677 | 67.72 | 245.3 | 3.62 | 46.97 | 220.25 | 4.69 | 75.22 | 150.76 | 2 | 3.44 |
| BM208112 | 54141 | 89.87 | 280.39 | 3.12 | 60.72 | 181.27 | 2.99 | 69.1 | 289.35 | 4.19 | 3.43 |
| C79445 | 627110 /// 631582 /// 73710 | 31.75 | 92.58 | 2.92 | 39.64 | 80.25 | 2.02 | 24.36 | 130.43 | 5.35 | 3.43 |
| NM_133217 | 170752 | 57.75 | 177.71 | 3.08 | 52.97 | 89.94 | 1.7 | 44.09 | 242.31 | 5.5 | 3.43 |
| AI119761 | 100040353 /// 100046169 | 81.68 | 257.24 | 3.15 | 71.51 | 253.25 | 3.54 | 32.31 | 116.14 | 3.59 | 3.43 |
| BC027435 | 68014 | 108.57 | 351.43 | 3.24 | 96.1 | 197.13 | 2.05 | 76.87 | 383.15 | 4.98 | 3.42 |
| BC021385 | 217830 | 117.93 | 399.78 | 3.39 | 98.79 | 263.69 | 2.67 | 113.85 | 476.87 | 4.19 | 3.42 |
| AV025559 | 227753 | 399.17 | 926.74 | 2.32 | 347.46 | 697.3 | 2.01 | 357.88 | 2086.52 | 5.83 | 3.39 |
| BB821996 | 75939 | 193.94 | 517.7 | 2.67 | 120.65 | 395.59 | 3.28 | 134.06 | 563.77 | 4.21 | 3.39 |
| NM_009862 | 12544 | 117.56 | 348 | 2.96 | 73.93 | 185.85 | 2.51 | 87.6 | 411.16 | 4.69 | 3.39 |
| BG919998 | 53416 | 320.86 | 1100.83 | 3.43 | 218.94 | 840.33 | 3.84 | 410.38 | 1177.66 | 2.87 | 3.38 |
| BC003475 | 22151 | 253.78 | 932.56 | 3.67 | 450.58 | 1378.1 | 3.06 | 320.58 | 1090.79 | 3.4 | 3.38 |
| AV298107 | 69554 | 293.25 | 1039.9 | 3.55 | 313.4 | 856.69 | 2.73 | 246.22 | 933.85 | 3.79 | 3.36 |
| BC005475 | 233406 | 562.24 | 1404.26 | 2.5 | 136.36 | 540.65 | 3.96 | 634.32 | 2256.38 | 3.56 | 3.34 |
| AF036898 | 18974 | 154.96 | 470.7 | 3.04 | 111.29 | 222.24 | 2 | 110.85 | 551.66 | 4.98 | 3.34 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| BB558905 | 56175 | 463.85 | 1630.66 | 3.52 | 308.85 | 1453.04 | 4.7 | 582.66 | 1037.96 | 1.78 | 3.33 |
| AK014608 | 74041 | 105.3 | 353.85 | 3.36 | 101.99 | 270.48 | 2.65 | 95.57 | 381.71 | 3.99 | 3.33 |
| AK020278 | 381319 | 605.38 | 1441.62 | 2.38 | 540.1 | 1768.04 | 3.27 | 362.55 | 1573.64 | 4.34 | 3.33 |
| BC005475 | 233406 | 286.56 | 717.89 | 2.51 | 69.42 | 280.51 | 4.04 | 344.47 | 1180.95 | 3.43 | 3.33 |
| BG916502 | 229841 | 112.18 | 319.5 | 2.85 | 44.11 | 162.07 | 3.67 | 75.25 | 260.56 | 3.46 | 3.33 |
| BC004727 | 67776 | 736.66 | 1679.74 | 2.28 | 182.84 | 908.08 | 4.97 | 602.12 | 1630.41 | 2.71 | 3.32 |
| NM_053090 | 84652 | 471.11 | 1310.88 | 2.78 | 306.25 | 782.76 | 2.56 | 341.51 | 1574.02 | 4.61 | 3.32 |
| NM_028803 | 74185 | 206.94 | 545.81 | 2.64 | 290.87 | 365.33 | 1.26 | 277.88 | 1680.1 | 6.05 | 3.32 |
| NM_133762 | 76044 | 240.86 | 662.86 | 2.75 | 133.59 | 480.4 | 3.6 | 195.75 | 705.49 | 3.6 | 3.32 |
| BB443362 | 223691 | 29.2 | 120.95 | 4.14 | 54.43 | 165.05 | 3.03 | 41.82 | 115.96 | 2.77 | 3.31 |
| NM_008284 | 15461 | 412.61 | 1718.17 | 4.16 | 409.72 | 1090.17 | 2.66 | 500.62 | 1554.57 | 3.11 | 3.31 |
| AV228517 | 17119 | 161.11 | 528.69 | 3.28 | 182.46 | 488.36 | 2.68 | 151.4 | 595.77 | 3.93 | 3.30 |
| NM_009502 | 22330 | 62.08 | 211.08 | 3.4 | 44.31 | 187.05 | 4.22 | 73.25 | 165.39 | 2.26 | 3.29 |
| AI840508 | 100039163 /// 100039840 /// 100040109 /// 100040898 /// 100041245 /// 100041342 /// 100042349 /// 100042427 /// 100042746 /// 100043724 /// 100043853 /// 100044628 /// 100045141 /// 100045230 /// 100046067 /// 100046937 /// 100047232 /// 100047352 /// 100 | 365.44 | 1169.75 | 3.2 | 399.46 | 860.89 | 2.16 | 459.57 | 2064.62 | 4.49 | 3.28 |
| BM208112 | 54141 | 65.77 | 185.77 | 2.82 | 32.47 | 106.03 | 3.27 | 47.41 | 178.48 | 3.76 | 3.28 |
| BC025460 | 68298 | 537.68 | 1195.82 | 2.22 | 185.07 | 894.3 | 4.83 | 440.26 | 1218.93 | 2.77 | 3.27 |
| NM_009445 | 22137 | 77.03 | 250.79 | 3.26 | 36.9 | 104.01 | 2.82 | 63.88 | 238.4 | 3.73 | 3.27 |
| AA153477 | 21991 | 1614.64 | 4662.33 | 2.89 | 838.97 | 2051.5 | 2.45 | 1848.04 | 8189.79 | 4.43 | 3.26 |
| BB528391 | 59126 | 136.76 | 423.31 | 3.1 | 128.91 | 468.6 | 3.64 | 114.5 | 344.39 | 3.01 | 3.25 |
| NM_007900 | 13605 | 264.44 | 647.59 | 2.45 | 87.13 | 362.58 | 4.16 | 178.4 | 553.71 | 3.1 | 3.24 |
| BM877490 | 75317 | 59.19 | 199.65 | 3.37 | 27.96 | 69.26 | 2.48 | 43.08 | 166.45 | 3.86 | 3.24 |
| NM_024438 | 68082 | 344.37 | 810.9 | 2.35 | 113.98 | 494.59 | 4.34 | 273.52 | 819.7 | 3 | 3.23 |
| BM211413 | 21973 | 775.99 | 2040.29 | 2.63 | 320.44 | 1240.3 | 3.87 | 691.3 | 2188.06 | 3.17 | 3.22 |
| AV126179 | 74107 | 67.11 | 200.99 | 3 | 31.97 | 82.6 | 2.58 | 40.45 | 165.39 | 4.09 | 3.22 |
| NM_009255 | 20720 | 6229.72 | 14318.9 | 2.3 | 2810.77 | 13072.29 | 4.65 | 5667.23 | 15378.31 | 2.71 | 3.22 |
| NM_023294 | 67052 | 118 | 316.93 | 2.69 | 73.04 | 177.86 | 2.44 | 78.87 | 356.51 | 4.52 | 3.22 |
| NM_021891 | 60530 | 328.39 | 893.26 | 2.72 | 151.26 | 381.71 | 2.52 | 233.31 | 1025.77 | 4.4 | 3.21 |
| BC026795 | 69263 | 221.81 | 652.92 | 2.94 | 393.28 | 874.29 | 2.22 | 179.23 | 800.39 | 4.47 | 3.21 |
| BG061840 | 100039214 /// 100039229 /// 100039556 /// 100039762 /// 100039827 /// 100039840 /// 100039959 /// 100040001 /// 100040053 /// 100040109 /// 100040634 /// 100040898 /// 100041006 /// 100041204 /// 100041236 /// 100041245 /// 100041325 /// 100041342 /// 100 | 168.29 | 591.82 | 3.52 | 219.36 | 394.21 | 1.8 | 217.06 | 936.25 | 4.31 | 3.21 |
| AU018569 | 224171 | 114.45 | 437.96 | 3.83 | 139.32 | 245.01 | 1.76 | 81.73 | 329.39 | 4.03 | 3.21 |
| BB725358 | 215387 | 295.87 | 766.36 | 2.59 | 157.63 | 494.08 | 3.13 | 228.19 | 889.53 | 3.9 | 3.21 |
| BB218965 | | 338.89 | 1385.67 | 4.09 | 435.36 | 1155.63 | 2.65 | 341.02 | 979.72 | 2.87 | 3.20 |
| BC024862 | 381045 | 279.09 | 642.39 | 2.3 | 186.71 | 393.37 | 2.11 | 246.87 | 1278.35 | 5.18 | 3.20 |
| AV040390 | 72243 | 53.23 | 176.57 | 3.32 | 46.5 | 135.2 | 2.91 | 47.52 | 157.9 | 3.32 | 3.18 |
| AI324988 | 17218 | 734.82 | 1823.22 | 2.48 | 523.62 | 1392.34 | 2.66 | 493.12 | 2168.61 | 4.4 | 3.18 |
| BB311061 | 56876 | 230.21 | 675.39 | 2.93 | 182.9 | 620.52 | 3.39 | 180.8 | 579.78 | 3.21 | 3.18 |
| BC027197 | 211389 | 376.78 | 1250.98 | 3.32 | 205.85 | 664.03 | 3.23 | 327.17 | 967.63 | 2.96 | 3.17 |
| BG067086 | 269582 | 160.24 | 382.18 | 2.39 | 73.71 | 219.55 | 2.98 | 93.21 | 385.15 | 4.13 | 3.17 |
| BI151440 | 12495 | 451.58 | 772.99 | 1.71 | 186.55 | 262.72 | 1.41 | 364.72 | 2322.97 | 6.37 | 3.16 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| NM_009791 | 12316 | 161.42 | 404.01 | 2.5 | 62.16 | 259.75 | 4.18 | 109.4 | 307.87 | 2.81 | 3.16 |
| C77256 | 110611 | 376.95 | 902.46 | 2.39 | 179.11 | 554.76 | 3.1 | 319.33 | 1264.34 | 3.96 | 3.15 |
| AV347825 | 433100 | 85.2 | 231.56 | 2.72 | 56.31 | 215.98 | 3.84 | 58.84 | 169.74 | 2.88 | 3.15 |
| NM_013888 | 30045 | 473.84 | 1380.82 | 2.91 | 306.85 | 1230.77 | 4.01 | 519.76 | 1304.68 | 2.51 | 3.14 |
| AK014312 | 17022 | 2635.11 | 5584.24 | 2.12 | 1301.33 | 5555.4 | 4.27 | 2019.91 | 6129.42 | 3.03 | 3.14 |
| NM_026202 | 67501 | 253.93 | 590.83 | 2.33 | 126.16 | 577.42 | 4.58 | 190.38 | 476.11 | 2.5 | 3.14 |
| AV062214 | 11746 | 129.45 | 291.94 | 2.26 | 76.32 | 228.61 | 3 | 78.17 | 323.09 | 4.13 | 3.13 |
| NM_026633 | 68241 | 95.08 | 294.78 | 3.1 | 101.62 | 280.24 | 2.76 | 81.28 | 287.09 | 3.53 | 3.13 |
| NM_028232 | 72415 | 158.19 | 412.34 | 2.61 | 93.42 | 270.21 | 2.89 | 116.98 | 448.91 | 3.84 | 3.11 |
| AK006387 | 17436 /// 630951 /// 677317 | 226.03 | 465.97 | 2.06 | 130.71 | 250.19 | 1.91 | 212.09 | 1137.77 | 5.36 | 3.11 |
| BI465645 |  | 40.35 | 100.22 | 2.48 | 62.84 | 96.31 | 1.53 | 39.56 | 210.34 | 5.32 | 3.11 |
| NM_025539 | 66401 | 547.51 | 999.48 | 1.83 | 188.47 | 858.69 | 4.56 | 422.42 | 1232.85 | 2.92 | 3.10 |
| BC005440 | 19217 | 1179.52 | 2698.34 | 2.29 | 207.14 | 875.32 | 4.23 | 767.48 | 2130.17 | 2.78 | 3.10 |
| AK009885 | 100036521 | 472.99 | 1042.16 | 2.2 | 126.83 | 534.57 | 4.21 | 348.07 | 1000.1 | 2.87 | 3.09 |
| NM_024435 | 67405 | 93.18 | 242.72 | 2.6 | 63.3 | 182.16 | 2.88 | 74.59 | 283.21 | 3.8 | 3.09 |
| BB667349 |  | 130.31 | 393.77 | 3.02 | 42.2 | 97.13 | 2.3 | 105 | 412.76 | 3.93 | 3.08 |
| NM_018790 | 11838 | 93.4 | 451.66 | 4.84 | 137.14 | 378.61 | 2.76 | 99.06 | 156.68 | 1.58 | 3.06 |
| AW554436 | 11431 | 97.63 | 366.9 | 3.76 | 169.77 | 511.6 | 3.01 | 151.16 | 362.12 | 2.4 | 3.06 |
| AK003744 | 73720 | 66.69 | 247.49 | 3.71 | 81.57 | 202.73 | 2.49 | 63.27 | 186.35 | 2.95 | 3.05 |
| AK014503 | 22062 | 587.49 | 1686.98 | 2.87 | 375.84 | 1312.59 | 3.49 | 673.6 | 1874.7 | 2.78 | 3.05 |
| BB426900 | 329973 | 35.38 | 92.26 | 2.61 | 39.34 | 93.25 | 2.37 | 38.15 | 158.75 | 4.16 | 3.05 |
| AV316937 | 68549 | 109.02 | 309.5 | 2.84 | 74.84 | 197.27 | 2.64 | 71.11 | 259.21 | 3.65 | 3.04 |
| BC010826 | 70186 | 1682.42 | 4085.42 | 2.43 | 1333.93 | 2536.09 | 1.9 | 1714.49 | 8233.09 | 4.8 | 3.04 |
| NM_013471 | 11746 | 427.99 | 1037.43 | 2.42 | 288.78 | 861.76 | 2.98 | 313.71 | 1167.23 | 3.72 | 3.04 |
| NM_025779 | 66815 | 514.85 | 1121.65 | 2.18 | 259.21 | 877.78 | 3.39 | 379.68 | 1344.71 | 3.54 | 3.04 |
| AK013636 | 72938 | 151.8 | 427.96 | 2.82 | 131.24 | 427.78 | 3.26 | 146.09 | 443.14 | 3.03 | 3.04 |
| BC005590 | 20193 | 249.35 | 686.37 | 2.75 | 210.36 | 668.33 | 3.18 | 230.6 | 731.48 | 3.17 | 3.03 |
| NM_019718 | 56350 | 900.82 | 2540.36 | 2.82 | 647.62 | 2204.71 | 3.4 | 762.66 | 2132.78 | 2.8 | 3.01 |
| BB198687 |  | 165.4 | 426.07 | 2.58 | 197.67 | 359.96 | 1.82 | 146.68 | 677.73 | 4.62 | 3.01 |
| AV000569 | 217149 | 747.1 | 1836.8 | 2.46 | 469.55 | 1299.02 | 2.77 | 639.42 | 2407.27 | 3.76 | 3.00 |
| AK018331 | 76205 | 344.84 | 1011.73 | 2.93 | 300.21 | 950.73 | 3.17 | 340.47 | 977.83 | 2.87 | 2.99 |
| NM_013755 | 27357 | 913.78 | 2066.37 | 2.26 | 434.33 | 1704.7 | 3.92 | 856.84 | 2335.63 | 2.73 | 2.97 |
| AV253087 | 19221 | 60.93 | 220.55 | 3.62 | 196.96 | 364.52 | 1.85 | 61.65 | 210.44 | 3.41 | 2.96 |
| NM_019517 | 56175 | 529.98 | 1598.25 | 3.02 | 359.61 | 1565.87 | 4.35 | 795.02 | 1177.12 | 1.48 | 2.95 |
| NM_023587 | 70757 | 483.47 | 1361.35 | 2.82 | 368.72 | 1394.46 | 3.78 | 638.89 | 1434.31 | 2.25 | 2.95 |
| NM_008566 | 17218 | 384.49 | 868.74 | 2.26 | 282.56 | 750.79 | 2.66 | 279.09 | 1098.06 | 3.93 | 2.95 |
| BB667085 | 100040353 /// 100046169 | 84.33 | 271.39 | 3.22 | 75.41 | 248.22 | 3.29 | 45.11 | 105.75 | 2.34 | 2.95 |
| BM247465 | 108961 | 111.44 | 273.16 | 2.45 | 83.45 | 265.15 | 3.18 | 91.69 | 294.6 | 3.21 | 2.95 |
| U31625 | 12189 | 64.14 | 180.68 | 2.82 | 46.79 | 140.04 | 2.99 | 60.49 | 182.67 | 3.02 | 2.94 |
| BC003476 | 16149 | 301.39 | 1215.1 | 4.03 | 311.57 | 867.77 | 2.79 | 291.69 | 584.33 | 2 | 2.94 |
| NM_009401 | 21941 | 45.74 | 110.64 | 2.42 | 53.9 | 70.56 | 1.31 | 59.79 | 303.51 | 5.08 | 2.94 |
| NM_008776 | 18476 | 321.54 | 810.19 | 2.52 | 325.9 | 712.84 | 2.19 | 405.88 | 1663.24 | 4.1 | 2.94 |
| BE457796 | 74103 | 34.23 | 159.69 | 4.67 | 50.47 | 111.93 | 2.22 | 28.71 | 54.75 | 1.91 | 2.93 |
| BC002008 | 16592 /// 547041 /// 620603 | 1417.5 | 3869.75 | 2.73 | 1398.38 | 3196.17 | 2.29 | 1887.69 | 7141.88 | 3.78 | 2.93 |
| BB284482 | 14586 | 465.34 | 1443 | 3.1 | 110.09 | 380.03 | 3.45 | 482.09 | 1067.78 | 2.21 | 2.92 |
| BB131147 | 56699 | 73.5 | 306.12 | 4.16 | 156.76 | 387.65 | 2.47 | 121.38 | 258.53 | 2.13 | 2.92 |
| Y19235 | 22062 | 248.15 | 747.28 | 3.01 | 199.31 | 588.25 | 2.95 | 356.38 | 995.95 | 2.79 | 2.92 |
| AI447570 |  | 65 | 159.7 | 2.46 | 64.5 | 259.17 | 4.02 | 62.97 | 142.51 | 2.26 | 2.91 |
| BB104669 | 73804 | 146.16 | 455.03 | 3.11 | 106.92 | 238.18 | 2.23 | 122.74 | 413.93 | 3.37 | 2.90 |
| AI462899 | 78405 | 134.46 | 326.3 | 2.43 | 94.49 | 232.06 | 2.46 | 123.21 | 470.86 | 3.82 | 2.90 |
| AF199491 | 100047134 /// 12457 | 127.31 | 180.72 | 1.42 | 218.16 | 266.83 | 1.22 | 96.74 | 585.74 | 6.05 | 2.90 |
| BC003428 | 66929 | 348.96 | 856.39 | 2.45 | 220.12 | 553.91 | 2.52 | 259.74 | 959.79 | 3.7 | 2.89 |
| BB702754 | 18140 | 126.61 | 325.95 | 2.57 | 79.96 | 228.67 | 2.86 | 105.65 | 341.84 | 3.24 | 2.89 |
| AU019438 | 69456 | 455.89 | 1404.37 | 3.08 | 426.46 | 1140.71 | 2.67 | 427.37 | 1242.49 | 2.91 | 2.89 |
| AK013867 | 70218 | 97.12 | 294.46 | 3.03 | 65.71 | 167.67 | 2.55 | 90.64 | 278.91 | 3.08 | 2.89 |
| C87524 | 13070 | 52.74 | 181.85 | 3.45 | 51.09 | 58.19 | 1.14 | 45.81 | 186.41 | 4.07 | 2.89 |
| NM_020010 | 13121 | 538.03 | 1040.2 | 1.93 | 595.7 | 837.11 | 1.41 | 347.31 | 1840.44 | 5.3 | 2.88 |
| AV354744 | 16601 /// 70273 | 206.72 | 687.21 | 3.32 | 263.74 | 655.59 | 2.49 | 157.05 | 445.01 | 2.83 | 2.88 |
| BC011083 | 15461 | 349.98 | 1307.84 | 3.74 | 418.79 | 928.3 | 2.22 | 435.38 | 1156.1 | 2.66 | 2.87 |
| BM237177 | 225010 | 321.92 | 957.29 | 2.97 | 168.67 | 526.03 | 3.12 | 262.36 | 664.29 | 2.53 | 2.87 |
| AU017667 | 27357 | 1966.85 | 4060.45 | 2.06 | 810.62 | 3023.38 | 3.73 | 1563.62 | 4371.13 | 2.8 | 2.86 |
| NM_030690 | 75646 | 113.84 | 330.81 | 2.91 | 73.69 | 252.9 | 3.43 | 88.36 | 199.04 | 2.25 | 2.86 |
| AK008813 | 100042498 /// 100046671 | 243.44 | 467.94 | 1.92 | 309.77 | 1107.23 | 3.57 | 182.13 | 554.79 | 3.05 | 2.85 |
| AV031928 | 66257 | 144.72 | 361.91 | 2.5 | 106.19 | 308.91 | 2.91 | 110.97 | 346.64 | 3.12 | 2.84 |
| BB139986 | 64214 | 67.54 | 222.81 | 3.3 | 19.55 | 57.61 | 2.95 | 52.58 | 120.07 | 2.28 | 2.84 |
| NM_011694 | 22333 | 729.15 | 1733.33 | 2.38 | 654.16 | 1409.08 | 2.15 | 833.32 | 3321.35 | 3.99 | 2.84 |
| AV213379 | 67041 | 851.6 | 2372.79 | 2.79 | 452.36 | 1870.98 | 4.14 | 1123.12 | 1773.03 | 1.58 | 2.84 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| BB667958 | 328066 | 644.27 | 1602.7 | 2.49 | 211.22 | 809.69 | 3.83 | 741.58 | 1601.88 | 2.16 | 2.83 |
| NM_008017 | 14211 | 774.96 | 1426.52 | 1.84 | 176.12 | 791.66 | 4.49 | 612.96 | 1304.32 | 2.13 | 2.82 |
| J04620 | 19075 | 358.71 | 834.42 | 2.33 | 197.19 | 656.38 | 3.33 | 323.51 | 905.3 | 2.8 | 2.82 |
| BC003427 | 110033 | 132.5 | 393.22 | 2.97 | 97.33 | 202.77 | 2.08 | 107.64 | 367.5 | 3.41 | 2.82 |
| NM_007793 | 13014 | 2387.56 | 5508.93 | 2.31 | 1623.49 | 5814.98 | 3.58 | 2440.01 | 6238.82 | 2.56 | 2.82 |
| BB758819 | 20133 | 847.41 | 1722.44 | 2.03 | 352.76 | 1127.54 | 3.2 | 624.08 | 1999.74 | 3.2 | 2.81 |
| BI466124 | 70466 | 89.91 | 253.55 | 2.82 | 58.62 | 147.63 | 2.52 | 87.09 | 269.36 | 3.09 | 2.81 |
| BG797460 | 229317 | 299.36 | 880.95 | 2.94 | 395.8 | 1041.07 | 2.63 | 326.77 | 929.76 | 2.85 | 2.81 |
| J04620 | 19075 | 245.4 | 565.88 | 2.31 | 143.62 | 437.24 | 3.04 | 205.45 | 628.34 | 3.06 | 2.80 |
| BC004585 | 20460 | 111.91 | 286.66 | 2.56 | 109.57 | 306.78 | 2.8 | 103.96 | 317.1 | 3.05 | 2.80 |
| NM_009477 | 22271 | 62.35 | 210.47 | 3.38 | 53.83 | 113.38 | 2.11 | 78.09 | 228.33 | 2.92 | 2.80 |
| BE991735 | 100048700 /// 66170 | 177.32 | 471.95 | 2.66 | 194.06 | 605.53 | 3.12 | 166.62 | 436.63 | 2.62 | 2.80 |
| BE848253 | 108000 | 152.75 | 376.53 | 2.46 | 69.64 | 221.62 | 3.18 | 106.69 | 294.52 | 2.76 | 2.80 |
| AF100171 | 17349 | 55.9 | 151.84 | 2.72 | 146.91 | 381.12 | 2.59 | 51.92 | 160.18 | 3.09 | 2.80 |
| NM_054055 | 114644 | 196.33 | 342.45 | 1.74 | 145.15 | 382.01 | 2.63 | 174.35 | 701.42 | 4.02 | 2.80 |
| BC021637 | 12514 | 103.49 | 289.71 | 2.8 | 56.5 | 249.55 | 4.42 | 132.75 | 154.93 | 1.17 | 2.80 |
| AV000765 | 108689 | 249.91 | 490.19 | 1.96 | 81.87 | 319.97 | 3.91 | 207.34 | 520.77 | 2.51 | 2.79 |
| AW488914 | 272551 | 85.42 | 226.55 | 2.65 | 102.57 | 206.91 | 2.02 | 68.9 | 254.6 | 3.7 | 2.79 |
| BM208103 | 80986 | 153.39 | 384.77 | 2.51 | 93.34 | 253.35 | 2.71 | 112.73 | 353.77 | 3.14 | 2.79 |
| NM_007634 | 12449 | 112.61 | 295.19 | 2.62 | 45.89 | 93.66 | 2.04 | 72.76 | 268.34 | 3.69 | 2.78 |
| NM_009037 | 19672 | 150.08 | 433.89 | 2.89 | 113.54 | 330.5 | 2.91 | 146.98 | 372.03 | 2.53 | 2.78 |
| NM_020010 | 13121 | 117.97 | 269.97 | 2.29 | 140.67 | 209.81 | 1.49 | 90.64 | 411.97 | 4.55 | 2.78 |
| NM_009415 | 21991 | 2727.89 | 6245.71 | 2.29 | 1292.54 | 2780.01 | 2.15 | 3167.77 | 12295.37 | 3.88 | 2.77 |
| AK017734 | 75712 | 144.34 | 392.4 | 2.72 | 114.28 | 314.18 | 2.75 | 111.56 | 316.3 | 2.84 | 2.77 |
| BF122715 | 71238 | 143.62 | 321.2 | 2.24 | 69.78 | 280.81 | 4.02 | 129.81 | 266.15 | 2.05 | 2.77 |
| NM_019976 | 56742 | 133.92 | 371.82 | 2.78 | 114.17 | 332.45 | 2.91 | 125.46 | 327.57 | 2.61 | 2.77 |
| NM_023203 | 66422 | 488.77 | 1102.52 | 2.26 | 267.89 | 784.47 | 2.93 | 344.74 | 1069.73 | 3.1 | 2.76 |
| AK014530 | 28042 | 475.22 | 1243.09 | 2.62 | 292.3 | 704.59 | 2.41 | 363.98 | 1181.37 | 3.25 | 2.76 |
| NM_023516 | 69573 | 392.43 | 465.18 | 1.19 | 350.92 | 360.24 | 1.03 | 373.15 | 2252.98 | 6.04 | 2.75 |
| BC022648 | 69706 | 99.15 | 241.84 | 2.44 | 71.51 | 160.18 | 2.24 | 88.09 | 315.41 | 3.58 | 2.75 |
| BG068387 | 229841 | 100.42 | 178.34 | 1.78 | 39.82 | 148.1 | 3.72 | 71.79 | 197.87 | 2.76 | 2.75 |
| NM_007512 | 11983 | 1357.31 | 3589.65 | 2.64 | 1266.56 | 3286.29 | 2.59 | 1253.73 | 3782.3 | 3.02 | 2.75 |
| AW556344 | 216238 | 308.32 | 893.6 | 2.9 | 242.32 | 766.24 | 3.16 | 277.76 | 606.02 | 2.18 | 2.75 |
| AV078914 | 15108 | 1264.77 | 3005.48 | 2.38 | 705.98 | 2038.32 | 2.89 | 1354.49 | 4008.67 | 2.96 | 2.74 |
| AW108522 | 67092 | 74.62 | 164.37 | 2.2 | 54.03 | 106.46 | 1.97 | 67.85 | 274.01 | 4.04 | 2.74 |
| AW208668 | 67138 | 551.87 | 988.39 | 1.79 | 102.63 | 439.33 | 4.28 | 494.08 | 1050.05 | 2.13 | 2.73 |
| NM_021515 | 11636 | 119.69 | 316.43 | 2.64 | 104.23 | 260.31 | 2.5 | 113.6 | 346.96 | 3.05 | 2.73 |
| AA960125 | 73724 | 207.77 | 462.38 | 2.23 | 94.22 | 352.61 | 3.74 | 167.17 | 369.23 | 2.21 | 2.73 |
| BB530332 | 69955 | 107.16 | 365.15 | 3.41 | 146.14 | 390.75 | 2.67 | 114.47 | 240.83 | 2.1 | 2.73 |
| BG064119 | 100047893 /// 68815 | 300.23 | 581.79 | 1.94 | 137.67 | 576.72 | 4.19 | 270.01 | 551.81 | 2.04 | 2.72 |
| BF535947 | 22325 | 131.56 | 359.12 | 2.73 | 144.69 | 352.65 | 2.44 | 147.97 | 444.28 | 3 | 2.72 |
| AV216412 | 13685 | 396.38 | 789.1 | 1.99 | 310.93 | 630.66 | 2.03 | 494.2 | 2046.49 | 4.14 | 2.72 |
| AW123929 | 320946 | 38.09 | 131.28 | 3.45 | 78.12 | 182.45 | 2.34 | 41.92 | 98.86 | 2.36 | 2.72 |
| NM_023066 | 65973 | 315.05 | 700.24 | 2.22 | 166.75 | 479.75 | 2.88 | 311.36 | 945.81 | 3.04 | 2.71 |
| AK017612 | 70545 | 150.46 | 261.12 | 1.74 | 110.57 | 348.41 | 3.15 | 97.75 | 316.71 | 3.24 | 2.71 |
| BB227643 | 237887 | 213.02 | 589.35 | 2.77 | 115.51 | 328.8 | 2.85 | 212.61 | 531.72 | 2.5 | 2.71 |
| NM_033622 | 24099 | 174.67 | 433.17 | 2.48 | 116.48 | 340.47 | 2.92 | 142.72 | 385.21 | 2.7 | 2.70 |
| NM_010354 | 227753 | 609.49 | 1133.51 | 1.86 | 380.61 | 699.09 | 1.84 | 652.41 | 2857.96 | 4.38 | 2.69 |
| AI385771 | 20873 | 338.67 | 849.99 | 2.51 | 208.85 | 514.22 | 2.46 | 216.16 | 671.55 | 3.11 | 2.69 |
| BB381550 |  | 51.61 | 136.1 | 2.64 | 46.81 | 82.72 | 1.77 | 46.01 | 168.86 | 3.67 | 2.69 |
| BF453953 | 66311 | 104.92 | 353.74 | 3.37 | 355.87 | 537.04 | 1.51 | 108.05 | 344.09 | 3.18 | 2.69 |
| NM_133662 | 15937 | 598.18 | 2256.17 | 3.77 | 301.74 | 599.93 | 1.99 | 684.2 | 1565.3 | 2.29 | 2.68 |
| NM_010715 | 16881 | 389.11 | 819.23 | 2.11 | 259.4 | 775.65 | 2.99 | 377.7 | 1108.44 | 2.93 | 2.68 |
| M17962 | 13646 /// 13648 | 69.81 | 260.32 | 3.73 | 50.07 | 81.11 | 1.62 | 70.4 | 185.89 | 2.64 | 2.66 |
| BB076574 | 56421 | 1005.22 | 1703.43 | 1.69 | 396.52 | 970.8 | 2.45 | 785.61 | 3012.62 | 3.83 | 2.66 |
| NM_019665 | 56297 | 286.28 | 887.61 | 3.1 | 221.99 | 661.15 | 2.98 | 317.12 | 598.38 | 1.89 | 2.66 |
| BB311718 | 230904 | 49.89 | 160.82 | 3.22 | 46.21 | 85.67 | 1.85 | 49.68 | 143.97 | 2.9 | 2.66 |
| AV219447 | 54138 | 1102.33 | 2047.02 | 1.86 | 651.05 | 1942.27 | 2.98 | 800.88 | 2499.83 | 3.12 | 2.65 |
| BM199355 | 12745 | 167.79 | 391.66 | 2.33 | 126.78 | 356.01 | 2.81 | 143.44 | 403.13 | 2.81 | 2.65 |
| BB538449 | 70454 | 324.61 | 682.91 | 2.1 | 161.21 | 545.83 | 3.39 | 261.16 | 640.88 | 2.45 | 2.65 |
| BB320288 | 57740 | 202.29 | 495.04 | 2.45 | 112.43 | 283.72 | 2.52 | 186.8 | 555.64 | 2.97 | 2.65 |
| NM_023217 | 66522 | 183.07 | 490.48 | 2.68 | 69.32 | 114.76 | 1.66 | 139.46 | 502.1 | 3.6 | 2.65 |
| BC022165 | 13143 | 151.74 | 294.95 | 1.94 | 75.66 | 210.11 | 2.78 | 80.37 | 258.84 | 3.22 | 2.65 |
| AK016617 | 28042 | 190.63 | 543.6 | 2.85 | 136.02 | 320.03 | 2.35 | 177.33 | 482.38 | 2.72 | 2.64 |
| BB827235 | 16551 | 158.54 | 448.94 | 2.83 | 104.32 | 235.2 | 2.25 | 148.92 | 422.83 | 2.84 | 2.64 |
| AK002609 | 68346 | 203.23 | 319.69 | 1.57 | 64.6 | 255.38 | 3.95 | 182.61 | 438.21 | 2.4 | 2.64 |
| AW553715 | 230857 | 848.11 | 2169.46 | 2.56 | 1119.66 | 2261.87 | 2.02 | 637.06 | 2119.16 | 3.33 | 2.64 |
| NM_007421 | 11565 | 101.09 | 224.24 | 2.22 | 93.19 | 198.95 | 2.14 | 79.08 | 281.04 | 3.55 | 2.64 |
| BC004801 | 319554 | 482.62 | 951.83 | 1.97 | 334.71 | 542.22 | 1.62 | 374.85 | 1610.34 | 4.3 | 2.63 |
| BI731319 | 23969 | 69.87 | 248.57 | 3.56 | 93.57 | 209.25 | 2.24 | 54.6 | 113.32 | 2.08 | 2.63 |
| BB706685 | 71865 | 72.33 | 97.6 | 1.35 | 30.4 | 96.48 | 3.17 | 44.51 | 149.06 | 3.35 | 2.62 |
| BC014860 | 104418 | 599.89 | 2553.13 | 4.26 | 709.61 | 1747.49 | 2.46 | 1192.33 | 1364.5 | 1.14 | 2.62 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| BC021427 | 15366 | 201.35 | 626.37 | 3.11 | 169.3 | 343.18 | 2.03 | 205.29 | 557.67 | 2.72 | 2.62 |
| AK016786 | 71804 | 83.84 | 227.19 | 2.71 | 79.32 | 144.77 | 1.83 | 68.61 | 227.49 | 3.32 | 2.62 |
| NM_010386 | 14998 | 245.37 | 609.51 | 2.48 | 256.08 | 664.8 | 2.6 | 267.59 | 741.97 | 2.77 | 2.62 |
| M25487 | 100046213 /// 319179 /// 319185 /// 319186 /// 319188 /// 319189 /// 665596 /// 665622 /// 68024 | 1568.71 | 3202.62 | 2.04 | 1636.43 | 3260.71 | 1.99 | 1089.79 | 4147.7 | 3.81 | 2.61 |
| NM_053261 | 114663 | 900.87 | 1711.3 | 1.9 | 601.55 | 1225.26 | 2.04 | 879.05 | 3415.86 | 3.89 | 2.61 |
| M64266 | 12326 | 431.26 | 961.45 | 2.23 | 259.67 | 802.88 | 3.09 | 409.06 | 1026.77 | 2.51 | 2.61 |
| BB540053 | 217653 | 165.75 | 337.87 | 2.04 | 70.88 | 203.7 | 2.87 | 116.57 | 340.55 | 2.92 | 2.61 |
| NM_028744 | 67073 | 50.31 | 161.15 | 3.2 | 45.47 | 109.68 | 2.41 | 64.27 | 141.48 | 2.2 | 2.60 |
| NM_013602 | 17748 | 1657.52 | 3309.16 | 2 | 2699.6 | 4047.58 | 1.5 | 2151.87 | 9268.68 | 4.31 | 2.60 |
| NM_010398 | 667803 | 299.85 | 637.51 | 2.13 | 209.36 | 453.9 | 2.17 | 306.24 | 1076.38 | 3.51 | 2.60 |
| BM220475 | 100038946 /// 380608 /// 72536 | 1025.16 | 3477.04 | 3.39 | 994.5 | 2664.94 | 2.68 | 1165.47 | 2012.8 | 1.73 | 2.60 |
| BB018660 | 381259 | 346.95 | 909.47 | 2.62 | 255.46 | 774.04 | 3.03 | 457.92 | 984.68 | 2.15 | 2.60 |
| X83932 | 20190 | 39.18 | 101 | 2.58 | 37.67 | 140.26 | 3.72 | 41.54 | 62.03 | 1.49 | 2.60 |
| BC025110 | 68927 | 596.13 | 1398.9 | 2.35 | 568.14 | 1309.1 | 2.3 | 522.31 | 1631.2 | 3.12 | 2.59 |
| AK011522 | 100047091 /// 72160 | 340.11 | 819.9 | 2.41 | 287.75 | 754.07 | 2.62 | 323.61 | 887.86 | 2.74 | 2.59 |
| AF212320 | 26934 | 436.34 | 888.51 | 2.04 | 216.72 | 687.36 | 3.17 | 379.79 | 971.4 | 2.56 | 2.59 |
| M23182 | 18646 | 151.19 | 264.39 | 1.75 | 103.77 | 128.46 | 1.24 | 127.51 | 604.64 | 4.74 | 2.58 |
| NM_009403 | 21949 | 145.77 | 286.36 | 1.96 | 157.23 | 1083.51 | 6.89 | 135.25 | 119 | −1.14 | 2.57 |
| BB830191 | 67733 | 228.66 | 470.16 | 2.06 | 107.23 | 421.86 | 3.93 | 221.61 | 377.68 | 1.7 | 2.56 |
| NM_025464 | 66279 | 244.54 | 561.63 | 2.3 | 124.65 | 390.36 | 3.13 | 202.92 | 458.44 | 2.26 | 2.56 |
| NM_013754 | 27356 | 292.67 | 680.23 | 2.32 | 273.63 | 734.44 | 2.68 | 260.04 | 697.56 | 2.68 | 2.56 |
| BB251322 | 110033 | 1188.07 | 2626.59 | 2.21 | 831.4 | 1652.06 | 1.99 | 739.77 | 2567.16 | 3.47 | 2.56 |
| BM234652 | 50527 | 1245.07 | 2007.72 | 1.61 | 862.21 | 1069.03 | 1.24 | 1247.9 | 6003.9 | 4.81 | 2.55 |
| NM_025872 | 66964 | 177.09 | 555.31 | 3.14 | 224.91 | 448.51 | 1.99 | 174.35 | 441.03 | 2.53 | 2.55 |
| AU044383 | 75316 | 236.43 | 808.82 | 3.42 | 996.93 | 1403.29 | 1.41 | 324.52 | 910.52 | 2.81 | 2.55 |
| NM_023380 | 67742 | 612.36 | 1486.16 | 2.43 | 451.78 | 1371.19 | 3.04 | 763.08 | 1646.94 | 2.16 | 2.54 |
| NM_009829 | 12444 | 276.27 | 509.7 | 1.84 | 97.49 | 314.48 | 3.23 | 291.11 | 744.9 | 2.56 | 2.54 |
| NM_010135 | 13800 | 37.64 | 73.84 | 1.96 | 43.19 | 127.4 | 2.95 | 37.75 | 102.63 | 2.72 | 2.54 |
| NM_011655 | 22154 | 3825.9 | 7807.34 | 2.04 | 2435.39 | 6736 | 2.77 | 3386.23 | 9520.05 | 2.81 | 2.54 |
| BC005581 | 69554 | 315.29 | 900.02 | 2.85 | 337.85 | 826.63 | 2.45 | 347.71 | 805.24 | 2.32 | 2.54 |
| BC008103 | 229524 | 319.7 | 703.32 | 2.2 | 127.24 | 426.31 | 3.35 | 278.24 | 573.85 | 2.06 | 2.54 |
| BM250919 | 218977 | 119.75 | 331.08 | 2.76 | 92.03 | 193.78 | 2.11 | 105.59 | 289.26 | 2.74 | 2.54 |
| NM_019699 | 56473 | 52.39 | 105.21 | 2.01 | 58.89 | 106.32 | 1.81 | 49.47 | 187.33 | 3.79 | 2.54 |
| AV048291 | 67389 | 366.06 | 773.59 | 2.11 | 409.69 | 900.42 | 2.2 | 283.01 | 931.6 | 3.29 | 2.53 |
| AV349681 | 66964 | 97.75 | 321.76 | 3.29 | 210.32 | 369.63 | 1.76 | 85.24 | 217.66 | 2.55 | 2.53 |
| AK006283 | 67454 | 102.29 | 220.73 | 2.16 | 25.94 | 56.8 | 2.19 | 79.16 | 257.46 | 3.25 | 2.53 |
| AW537828 | 21991 | 3220.28 | 6817.48 | 2.12 | 1628.76 | 3386.99 | 2.08 | 3485.51 | 11822.06 | 3.39 | 2.53 |
| BB230296 | 12238 | 813.05 | 2192.84 | 2.7 | 635.32 | 1703.07 | 2.68 | 991.61 | 2171.97 | 2.19 | 2.52 |
| NM_026024 | 67196 | 171 | 441.75 | 2.58 | 87.76 | 213.29 | 2.43 | 172.46 | 440.86 | 2.56 | 2.52 |
| BG063931 | 233575 | 286.23 | 875.11 | 3.06 | 241.7 | 688.27 | 2.85 | 357.37 | 588.18 | 1.65 | 2.52 |
| BI684556 | 14211 | 232.37 | 290.6 | 1.25 | 37.59 | 184.49 | 4.91 | 229.45 | 318.18 | 1.39 | 2.52 |
| NM_025757 | 66771 | 131.65 | 318.09 | 2.42 | 76.68 | 203.81 | 2.66 | 148.26 | 362.71 | 2.45 | 2.51 |
| NM_030696 | 80879 | 346.49 | 594.53 | 1.72 | 265.85 | 246.09 | −1.08 | 344.31 | 2372.12 | 6.89 | 2.51 |
| AV092324 | 108992 | 220.64 | 711.11 | 3.22 | 167.24 | 496.97 | 2.97 | 190.84 | 254.27 | 1.33 | 2.51 |
| NM_008922 | 19076 | 168.83 | 416.22 | 2.47 | 178.25 | 395.39 | 2.22 | 163.73 | 464 | 2.83 | 2.51 |
| BB238604 | 70645 | 85.06 | 205.89 | 2.42 | 69.66 | 148.76 | 2.14 | 90.76 | 268.5 | 2.96 | 2.51 |
| NM_026584 | 68153 | 548.13 | 1156.22 | 2.11 | 340.97 | 635.48 | 1.86 | 401.15 | 1414.92 | 3.53 | 2.50 |
| NM_025427 | 66214 | 90.53 | 147.24 | 1.63 | 99.3 | 240.09 | 2.42 | 80.19 | 277 | 3.45 | 2.50 |
| AF305501 | 63959 | 375.62 | 1014.14 | 2.7 | 339.36 | 980.89 | 2.89 | 378.61 | 718.39 | 1.9 | 2.50 |
| BM114601 | 109115 | 169.62 | 390.03 | 2.3 | 170.94 | 436.65 | 2.55 | 170.52 | 450.34 | 2.64 | 2.50 |
| AF181829 | 56193 | 123.2 | 298.03 | 2.42 | 93.13 | 255.97 | 2.75 | 126.7 | 294.08 | 2.32 | 2.50 |
| AU018569 | 224171 | 81.18 | 243.71 | 3 | 102.82 | 162.06 | 1.58 | 66.56 | 192.4 | 2.89 | 2.49 |
| NM_011405 | 20540 | 57.44 | 150.26 | 2.62 | 58.82 | 188.43 | 3.2 | 62.01 | 102.49 | 1.65 | 2.49 |
| BB758819 | 20133 | 653.44 | 1358.15 | 2.08 | 329.58 | 908.03 | 2.76 | 556.66 | 1462.35 | 2.63 | 2.49 |
| NM_019971 | 54635 | 247.36 | 578.66 | 2.34 | 90.53 | 304.39 | 3.36 | 172.83 | 304.16 | 1.76 | 2.49 |
| BG076317 | 72828 | 108.56 | 350.5 | 3.23 | 97.46 | 189.97 | 1.95 | 113.45 | 258.62 | 2.28 | 2.49 |
| AV286809 | 58887 | 319.28 | 890.78 | 2.79 | 362.05 | 1063.91 | 2.94 | 318.89 | 549.24 | 1.72 | 2.48 |
| BC016095 | 228421 | 132.18 | 342.69 | 2.59 | 98.12 | 213.84 | 2.18 | 111.81 | 299.92 | 2.68 | 2.48 |
| X69698 | 20527 | 510.09 | 982.99 | 1.93 | 245.56 | 598.15 | 2.44 | 421.58 | 1292.77 | 3.07 | 2.48 |
| BB142324 | 14609 | 104.3 | 240.81 | 2.31 | 61.21 | 160.82 | 2.63 | 69.99 | 174.92 | 2.5 | 2.48 |
| BE956483 | 74438 | 60.57 | 146.31 | 2.42 | 21.38 | 33.69 | 1.58 | 45.35 | 155.89 | 3.44 | 2.48 |
| BC008259 | 66541 | 1072.35 | 1915.54 | 1.79 | 313.43 | 1179.85 | 3.76 | 881.91 | 1649.55 | 1.87 | 2.47 |
| BM054266 | 66848 | 466.6 | 945.35 | 2.03 | 161.29 | 597.22 | 3.7 | 413.86 | 699.14 | 1.69 | 2.47 |
| BB224658 | 70546 | 178.25 | 391.61 | 2.2 | 132.9 | 322.03 | 2.42 | 177.9 | 497.57 | 2.8 | 2.47 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AF248489 | 54189 | 70.84 | 216.31 | 3.05 | 62.99 | 127.47 | 2.02 | 73.87 | 173.6 | 2.35 | 2.47 |
| BF021309 | 67121 | 62.42 | 165.29 | 2.65 | 39.2 | 89.18 | 2.27 | 56.43 | 141.31 | 2.5 | 2.47 |
| BC003914 | 58875 | 893.54 | 1985.16 | 2.22 | 464.63 | 1476.39 | 3.18 | 1020.8 | 2047.8 | 2.01 | 2.47 |
| AV174021 | 19272 | 377.69 | 617.77 | 1.64 | 96.59 | 217.05 | 2.25 | 212.84 | 747.65 | 3.51 | 2.47 |
| BB070019 | 17155 | 828.63 | 1983.31 | 2.39 | 699.39 | 2053.5 | 2.94 | 861.99 | 1760.79 | 2.04 | 2.46 |
| NM_010585 | 16438 | 477.74 | 1098.55 | 2.3 | 334.45 | 843.53 | 2.52 | 568.49 | 1444.32 | 2.54 | 2.45 |
| AV036172 | 22333 | 1134.8 | 2200.47 | 1.94 | 937.26 | 1773.69 | 1.89 | 1005.47 | 3552.11 | 3.53 | 2.45 |
| NM_016843 | 54138 | 835.56 | 1747.75 | 2.09 | 549.6 | 1743.89 | 3.17 | 933.28 | 1956.06 | 2.1 | 2.45 |
| NM_023200 | 66385 | 538.4 | 1373.74 | 2.55 | 442.56 | 972.35 | 2.2 | 436.82 | 1142.22 | 2.61 | 2.45 |
| AF042856 | 15234 | 52.58 | 145.34 | 2.76 | 62.62 | 151.29 | 2.42 | 61.33 | 133.58 | 2.18 | 2.45 |
| NM_009195 | 20498 | 107.49 | 295.9 | 2.75 | 83.46 | 199.92 | 2.4 | 123.08 | 270.99 | 2.2 | 2.45 |
| NM_011871 | 23992 | 148.6 | 360.82 | 2.43 | 96.09 | 283.56 | 2.95 | 156.1 | 305.81 | 1.96 | 2.45 |
| AK009370 | 66365 | 112.68 | 234.14 | 2.08 | 92.01 | 281.12 | 3.06 | 79.98 | 175.87 | 2.2 | 2.45 |
| BB405795 | 211586 /// 319491 | 302.07 | 759.26 | 2.51 | 332.34 | 744.53 | 2.24 | 250.19 | 645.46 | 2.58 | 2.44 |
| BM209618 | 20525 | 643.84 | 1061.52 | 1.65 | 870.79 | 814.01 | −1.07 | 540.98 | 3643.79 | 6.74 | 2.44 |
| NM_138953 | 192657 | 1376.38 | 3759.63 | 2.73 | 1258.69 | 2791.57 | 2.22 | 1438.15 | 3398.36 | 2.36 | 2.44 |
| BB028312 | 14137 | 604.18 | 986.32 | 1.63 | 447.16 | 611.1 | 1.37 | 390.53 | 1682.08 | 4.31 | 2.44 |
| BG076333 | 17768 | 669.24 | 1272.4 | 1.9 | 368.38 | 1147.26 | 3.11 | 599.31 | 1364.31 | 2.28 | 2.43 |
| BB410537 | 72415 | 78.45 | 163.08 | 2.08 | 47.82 | 134.56 | 2.81 | 74.32 | 177.52 | 2.39 | 2.43 |
| AV086243 | 236900 | 452.41 | 1078.62 | 2.38 | 409.55 | 930.36 | 2.27 | 465.27 | 1223.26 | 2.63 | 2.43 |
| AK011112 | 100048391 /// 72461 | 322.09 | 852.42 | 2.65 | 263.76 | 665.14 | 2.52 | 315.65 | 667.18 | 2.11 | 2.43 |
| AI875447 | 208884 | 318.36 | 507.07 | 1.59 | 129.15 | 196.19 | 1.52 | 224.6 | 931.35 | 4.15 | 2.42 |
| BB277912 | 227154 | 314.13 | 709.06 | 2.26 | 130.11 | 391.83 | 3.01 | 276.5 | 550.09 | 1.99 | 2.42 |
| BB251459 | 106344 | 181.09 | 391.79 | 2.16 | 114.12 | 295.15 | 2.59 | 148.21 | 371.81 | 2.51 | 2.42 |
| BC011081 | 17436 /// 630951 /// 677317 | 103.28 | 253.6 | 2.46 | 110.83 | 162.83 | 1.47 | 151.73 | 505.4 | 3.33 | 2.42 |
| NM_133838 | 98878 | 91.12 | 239.65 | 2.63 | 95.73 | 207.71 | 2.17 | 106.14 | 260.59 | 2.46 | 2.42 |
| X82786 | 17345 | 750.52 | 1203.54 | 1.6 | 258.13 | 822.71 | 3.19 | 433.62 | 1068.82 | 2.46 | 2.42 |
| NM_138656 | 192156 | 179.77 | 341.58 | 1.9 | 143.66 | 347.19 | 2.42 | 155.68 | 456.45 | 2.93 | 2.42 |
| M75135 | 20527 | 1107.22 | 1792.38 | 1.62 | 412.54 | 1079.92 | 2.62 | 852.99 | 2555.5 | 3 | 2.41 |
| AW120830 | 100047012 /// 22193 | 502.63 | 1303.39 | 2.59 | 1249.43 | 2081.86 | 1.67 | 411.09 | 1222.64 | 2.97 | 2.41 |
| NM_010119 | 13660 | 613.61 | 1293.95 | 2.11 | 568.79 | 1381.29 | 2.43 | 482.7 | 1293.4 | 2.68 | 2.41 |
| BB755745 | 231986 | 73.41 | 245.72 | 3.35 | 78.27 | 154.31 | 1.97 | 63.83 | 121.07 | 1.9 | 2.41 |
| BG067649 | 13858 | 531.57 | 1112.31 | 2.09 | 372.8 | 939.68 | 2.52 | 455.05 | 1189.45 | 2.61 | 2.41 |
| BI647951 |  | 488.07 | 1018.07 | 2.09 | 603.91 | 954.44 | 1.58 | 333.9 | 1181.49 | 3.54 | 2.40 |
| NM_009254 | 20719 | 4324.48 | 8815.12 | 2.04 | 2577.54 | 7653.55 | 2.97 | 4104.03 | 8987.83 | 2.19 | 2.40 |
| AI551117 | 230857 | 361.35 | 896.93 | 2.48 | 304.74 | 927.09 | 3.04 | 392.44 | 659.86 | 1.68 | 2.40 |
| AK002294 | 67876 | 175.21 | 340.61 | 1.94 | 123.04 | 439.22 | 3.57 | 132.71 | 223.77 | 1.69 | 2.40 |
| BE456717 | 69982 | 57.8 | 120.39 | 2.08 | 80 | 199.36 | 2.49 | 58.77 | 154.11 | 2.62 | 2.40 |
| BB769890 | 242341 | 128.95 | 191.39 | 1.48 | 123.43 | 486.24 | 3.94 | 156.98 | 277.19 | 1.77 | 2.40 |
| X81633 | 54141 | 78.3 | 210.39 | 2.69 | 67.22 | 125.51 | 1.87 | 73.94 | 193.48 | 2.62 | 2.39 |
| BE951628 | 217653 | 64.44 | 137.68 | 2.14 | 43.03 | 111.65 | 2.59 | 52.78 | 129.15 | 2.45 | 2.39 |
| M19413 | 26947 | 68.51 | 147.72 | 2.16 | 73.62 | 162.3 | 2.2 | 70.64 | 199.33 | 2.82 | 2.39 |
| U31625 | 12189 | 47.57 | 106.33 | 2.24 | 30.25 | 82.27 | 2.72 | 50.63 | 111.72 | 2.21 | 2.39 |
| AV309164 | 54138 | 2298.33 | 4156.35 | 1.81 | 1295.22 | 3717.88 | 2.87 | 1744.1 | 4332.91 | 2.48 | 2.39 |
| AV216768 | 236539 /// 665516 /// 666036 /// 668771 /// 675316 | 793.79 | 2312.96 | 2.91 | 770.34 | 1873.01 | 2.43 | 865.59 | 1573.86 | 1.82 | 2.39 |
| BE914497 | 18641 | 477.37 | 880.94 | 1.85 | 254.86 | 336.91 | 1.32 | 699.66 | 2788.54 | 3.99 | 2.39 |
| NM_133667 | 18604 | 131.1 | 442.63 | 3.38 | 127.1 | 330.16 | 2.6 | 151.15 | 178.87 | 1.18 | 2.39 |
| AK017897 | 74732 | 808.6 | 1064.81 | 1.32 | 929.78 | 2728.04 | 2.93 | 575.68 | 1670.63 | 2.9 | 2.38 |
| AK009101 | 69456 | 620.47 | 1359 | 2.19 | 510.64 | 1198.47 | 2.35 | 513.75 | 1343.26 | 2.61 | 2.38 |
| AK005093 | 13999 | 378.13 | 812.73 | 2.15 | 343.28 | 789.27 | 2.3 | 268.48 | 726.03 | 2.7 | 2.38 |
| BB032012 | 67554 | 378.17 | 880.39 | 2.33 | 285.5 | 570.29 | 2 | 308.27 | 870.09 | 2.82 | 2.38 |
| NM_018736 | 17535 | 370.18 | 805.23 | 2.18 | 171.03 | 513.75 | 3 | 360.04 | 709.29 | 1.97 | 2.38 |
| AK007410 | 23882 | 112.29 | 210.37 | 1.87 | 140.01 | 163.25 | 1.17 | 126.23 | 519.33 | 4.11 | 2.38 |
| AK011345 | 109212 | 185.5 | 430.92 | 2.32 | 96.41 | 221.7 | 2.3 | 137.75 | 347.08 | 2.52 | 2.38 |
| BB209605 | 403202 | 336.05 | 833.81 | 2.48 | 207.16 | 459.05 | 2.22 | 231.05 | 562.52 | 2.43 | 2.38 |
| M14537 | 11443 | 73.96 | 130.42 | 1.76 | 88.36 | 295.13 | 3.34 | 68.75 | 139.56 | 2.03 | 2.38 |
| BB529913 | 12014 | 57.02 | 162.95 | 2.86 | 125.21 | 683.86 | 5.46 | 85.91 | 71.61 | −1.2 | 2.37 |
| AK015705 | 56224 | 60.9 | 142.21 | 2.34 | 61.46 | 130.47 | 2.12 | 53.47 | 142.13 | 2.66 | 2.37 |
| NM_019390 | 16905 | 259.71 | 479.56 | 1.85 | 586.53 | 1463.54 | 2.5 | 265.13 | 735.16 | 2.77 | 2.37 |
| BG065877 | 110611 | 1412.61 | 2695.94 | 1.91 | 856.1 | 1850.41 | 2.16 | 1302.74 | 3957.86 | 3.04 | 2.37 |
| BC003427 | 110033 | 109.24 | 287.4 | 2.63 | 96.31 | 170.43 | 1.77 | 97.53 | 264.03 | 2.71 | 2.37 |
| AV286396 | 227937 | 94.22 | 226.26 | 2.4 | 86.18 | 201.67 | 2.34 | 86.12 | 203.15 | 2.36 | 2.37 |
| AF037370 | 12865 | 53.99 | 94.82 | 1.76 | 51.82 | 94.25 | 1.82 | 48.76 | 171.48 | 3.52 | 2.37 |
| NM_010119 | 13660 | 830.86 | 1724.37 | 2.08 | 730.29 | 1717.43 | 2.35 | 660.74 | 1759.26 | 2.66 | 2.36 |
| BB034567 | 102932 | 397.03 | 836.83 | 2.11 | 272.96 | 770.33 | 2.82 | 350.91 | 758.75 | 2.16 | 2.36 |
| BC021466 | 77219 | 242.87 | 401.01 | 1.65 | 61.65 | 203.45 | 3.3 | 185.84 | 397.65 | 2.14 | 2.36 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| NM_010027 | 13202 | 1011.65 | 1867.37 | 1.85 | 792.72 | 2256.17 | 2.85 | 878.66 | 2088.97 | 2.38 | 2.36 |
| BC019781 | 66821 | 170.59 | 367.89 | 2.16 | 116.16 | 278.9 | 2.4 | 143.08 | 360.58 | 2.52 | 2.36 |
| BE631955 | 103397 | 48.97 | 152.96 | 3.12 | 52.16 | 120.96 | 2.32 | 62.04 | 101.76 | 1.64 | 2.36 |
| BI663320 | 15382 | 1891.58 | 4174 | 2.21 | 2885.11 | 4480.43 | 1.55 | 1611.8 | 5340.51 | 3.31 | 2.36 |
| AF039026 | 27007 | 4028.69 | 5392.85 | 1.34 | 770.81 | 3491.69 | 4.53 | 2362.4 | 2837.53 | 1.2 | 2.36 |
| BC003335 | 106344 | 326.43 | 738.92 | 2.26 | 251.15 | 595.44 | 2.37 | 291.91 | 713.37 | 2.44 | 2.36 |
| NM_008087 | 14453 | 166.95 | 447.02 | 2.68 | 159.45 | 277.64 | 1.74 | 140.31 | 371.25 | 2.65 | 2.36 |
| NM_013463 | 11605 | 192.7 | 371.25 | 1.93 | 113.02 | 318.01 | 2.81 | 163.72 | 381.22 | 2.33 | 2.36 |
| AI788952 | 15926 | 148.29 | 289.96 | 1.96 | 63.33 | 142.26 | 2.25 | 125.47 | 359.11 | 2.86 | 2.36 |
| AK013116 | 69270 | 106 | 217.6 | 2.05 | 85.47 | 167.82 | 1.96 | 80.39 | 245.86 | 3.06 | 2.36 |
| BM200015 | 72479 | 382.08 | 808.35 | 2.12 | 221.06 | 641.71 | 2.9 | 414.7 | 847.24 | 2.04 | 2.35 |
| AW259452 | 68695 | 87.75 | 161.68 | 1.84 | 46.07 | 120.73 | 2.62 | 70.62 | 182.83 | 2.59 | 2.35 |
| BB072090 | 59009 | 64.95 | 127.29 | 1.96 | 47.9 | 104.41 | 2.18 | 48.83 | 142.21 | 2.91 | 2.35 |
| BB805796 | 58875 | 993.32 | 2263.27 | 2.28 | 553.85 | 1692.03 | 3.06 | 1229.35 | 2095.62 | 1.7 | 2.35 |
| NM_008355 | 16163 | 313.92 | 457.7 | 1.46 | 283.95 | 479.77 | 1.69 | 275.09 | 1068.94 | 3.89 | 2.35 |
| U20658 | 22410 | 139.01 | 387.48 | 2.79 | 201.77 | 411.82 | 2.04 | 136.87 | 302.45 | 2.21 | 2.35 |
| AV031928 | 66257 | 131.55 | 294.95 | 2.24 | 129.87 | 268.25 | 2.07 | 124.41 | 337.93 | 2.72 | 2.34 |
| BM209618 | 20525 | 550.93 | 974.8 | 1.77 | 685.54 | 829.7 | 1.21 | 752.18 | 3042.79 | 4.05 | 2.34 |
| AV114522 | 65970 | 546.61 | 1237.63 | 2.26 | 170.78 | 478.57 | 2.8 | 479.82 | 942.74 | 1.96 | 2.34 |
| NM_025363 | 66117 | 231.08 | 572.02 | 2.48 | 219.81 | 497.33 | 2.26 | 238.46 | 543.23 | 2.28 | 2.34 |
| AK017206 | 76000 | 97.61 | 237.71 | 2.44 | 163.55 | 462.74 | 2.83 | 109.55 | 187.97 | 1.72 | 2.33 |
| NM_016763 | 15108 | 2533.94 | 4934.12 | 1.95 | 1553.89 | 3734.97 | 2.4 | 2514.9 | 6611.46 | 2.63 | 2.33 |
| NM_012025 | 26934 | 381.39 | 614.92 | 1.61 | 196.74 | 615.34 | 3.13 | 320.18 | 717.12 | 2.24 | 2.33 |
| AK007017 | 67015 | 216.64 | 463.95 | 2.14 | 277.71 | 599.03 | 2.16 | 222.7 | 596.04 | 2.68 | 2.33 |
| NM_009773 | 12236 | 158.5 | 453.08 | 2.86 | 102.82 | 193.07 | 1.88 | 157.27 | 353.02 | 2.24 | 2.33 |
| BB469274 | 71675 | 319.17 | 640.89 | 2.01 | 141.1 | 384.5 | 2.72 | 224.94 | 504.26 | 2.24 | 2.32 |
| BM120495 | 52398 | 270.91 | 641.9 | 2.37 | 267 | 575.87 | 2.16 | 300.41 | 729.54 | 2.43 | 2.32 |
| NM_010685 | 16784 | 396.48 | 740.66 | 1.87 | 204.11 | 527.15 | 2.58 | 392.18 | 981.14 | 2.5 | 2.32 |
| BC016495 | 225994 | 194.99 | 407.3 | 2.09 | 223.5 | 440.86 | 1.97 | 139.24 | 403.07 | 2.89 | 2.32 |
| NM_021788 | 60406 | 561.26 | 970.49 | 1.73 | 537.78 | 965.25 | 1.79 | 562.73 | 1924.62 | 3.42 | 2.31 |
| BG065056 | 108912 | 130.47 | 305.92 | 2.34 | 90.52 | 182.96 | 2.02 | 125.17 | 323.31 | 2.58 | 2.31 |
| NM_010807 | 17357 | 213.05 | 436.76 | 2.05 | 320.81 | 880.3 | 2.74 | 355.02 | 758.82 | 2.14 | 2.31 |
| AF309644 | 19301 | 218.17 | 541.34 | 2.48 | 243.44 | 517.88 | 2.13 | 208.94 | 483.92 | 2.32 | 2.31 |
| BB771921 | 70387 | 211.08 | 419.01 | 1.99 | 86.27 | 229.82 | 2.66 | 175.32 | 399.73 | 2.28 | 2.31 |
| BB793369 | 12972 | 166.18 | 344.21 | 2.07 | 126.99 | 245.14 | 1.93 | 118.34 | 346.87 | 2.93 | 2.31 |
| AK010745 | 73689 | 943.1 | 2157.26 | 2.29 | 765.59 | 1888.6 | 2.47 | 880.87 | 1900.07 | 2.16 | 2.31 |
| BB284309 | 320438 | 135.05 | 232.38 | 1.72 | 55.76 | 159.3 | 2.86 | 124.48 | 291.8 | 2.34 | 2.31 |
| NM_133726 | 70356 | 1045.02 | 2091.85 | 2 | 628.72 | 1869.36 | 2.97 | 1049.75 | 2040.35 | 1.94 | 2.30 |
| BC013820 | 20166 | 80.97 | 257.34 | 3.18 | 81.83 | 121.64 | 1.49 | 124.22 | 278.44 | 2.24 | 2.30 |
| BG076066 |  | 312.64 | 650.79 | 2.08 | 312.23 | 597.88 | 1.91 | 286.64 | 833.07 | 2.91 | 2.30 |
| BC019745 | 83921 | 241.98 | 604.06 | 2.5 | 325.2 | 641.89 | 1.97 | 150.17 | 364.77 | 2.43 | 2.30 |
| BC003916 | 67669 | 674.01 | 1052.86 | 1.56 | 191.61 | 692.88 | 3.62 | 698.22 | 1203.82 | 1.72 | 2.30 |
| BC021914 | 100047565 /// 67468 | 589.4 | 1754.38 | 2.98 | 960.76 | 1513.86 | 1.58 | 554.68 | 1291.81 | 2.33 | 2.30 |
| AV244484 | 75750 | 71.53 | 89.78 | 1.26 | 80.33 | 144.89 | 1.8 | 54.35 | 207.9 | 3.83 | 2.30 |
| K00083 | 15978 | 1830.88 | 5434.63 | 2.97 | 2781.68 | 6019.57 | 2.16 | 2884.76 | 5035.9 | 1.75 | 2.29 |
| BC024334 | 68117 | 341.07 | 729.75 | 2.14 | 246.41 | 588.82 | 2.39 | 320.13 | 749.49 | 2.34 | 2.29 |
| BC028439 | 66395 | 253 | 581.4 | 2.3 | 430.15 | 680.74 | 1.58 | 203.23 | 607.69 | 2.99 | 2.29 |
| BB089991 | 26949 | 177.7 | 444.06 | 2.5 | 251.24 | 581.69 | 2.32 | 243.44 | 499.44 | 2.05 | 2.29 |
| AK002313 | 68607 | 422.53 | 819.16 | 1.94 | 264.71 | 679.62 | 2.57 | 340.97 | 804.64 | 2.36 | 2.29 |
| NM_024188 | 67041 | 2520.35 | 4745.13 | 1.88 | 1158.27 | 3746.69 | 3.23 | 2443.18 | 4274.32 | 1.75 | 2.29 |
| AV139821 | 100039683 /// 100045937 /// 270106 /// 76281 | 1514.23 | 2577.14 | 1.7 | 692.35 | 2181.07 | 3.15 | 1117.51 | 2241.49 | 2.01 | 2.29 |
| BC006809 | 29858 | 328.85 | 877.07 | 2.67 | 499.62 | 891.08 | 1.78 | 340.2 | 820.03 | 2.41 | 2.29 |
| BC023398 | 69634 | 218.84 | 350.96 | 1.6 | 179.64 | 202.41 | 1.13 | 213.02 | 876.96 | 4.12 | 2.28 |
| BC021308 | 76123 | 142.2 | 276 | 1.94 | 93.55 | 178 | 1.9 | 80.63 | 242.03 | 3 | 2.28 |
| BG076333 | 17768 | 719.92 | 1549.15 | 2.15 | 491.42 | 1321.44 | 2.69 | 804.85 | 1601.27 | 1.99 | 2.28 |
| NM_009647 | 100047616 /// 11639 | 170.87 | 237.92 | 1.39 | 177.96 | 192.28 | 1.08 | 153.09 | 667.06 | 4.36 | 2.28 |
| AV110584 | 17357 | 289.58 | 593.26 | 2.05 | 418.9 | 1039.04 | 2.48 | 402.49 | 926.68 | 2.3 | 2.28 |
| NM_025331 | 66066 | 805.58 | 2134.1 | 2.65 | 791.79 | 2048.39 | 2.59 | 784.07 | 1238.6 | 1.58 | 2.27 |
| AK002387 | 100048247 /// 76073 | 613.02 | 1061.31 | 1.73 | 790.79 | 1309.24 | 1.66 | 552.79 | 1898.56 | 3.43 | 2.27 |
| AK002320 | 100044663 /// 621156 /// 68316 | 409.69 | 834.45 | 2.04 | 285.92 | 704.85 | 2.47 | 351.61 | 811.64 | 2.31 | 2.27 |
| BC021914 | 67468 | 506.97 | 1673.1 | 3.3 | 793.28 | 1247.68 | 1.57 | 665.62 | 1293.95 | 1.94 | 2.27 |
| AV000840 | 105633 | 373.53 | 910.73 | 2.44 | 394.4 | 713.37 | 1.81 | 336.3 | 861.68 | 2.56 | 2.27 |
| BG064696 | 69549 | 151.27 | 347.6 | 2.3 | 164.18 | 415.76 | 2.53 | 171.37 | 340.05 | 1.98 | 2.27 |
| BE447255 |  | 910.88 | 2665.3 | 2.93 | 2635.64 | 4066.15 | 1.54 | 1499.68 | 3491.82 | 2.33 | 2.27 |
| U95030 | 11658 | 1084.63 | 2531.53 | 2.33 | 974.86 | 2822.05 | 2.89 | 1393.92 | 2206.23 | 1.58 | 2.27 |
| NM_008253 | 15354 | 337.04 | 1003.46 | 2.98 | 967.21 | 1283.1 | 1.33 | 334.52 | 833.91 | 2.49 | 2.27 |
| AF069051 | 30939 | 527.14 | 1145.94 | 2.17 | 506.14 | 1074.43 | 2.12 | 363.3 | 913.12 | 2.51 | 2.27 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AK017691 | 76816 | 175.42 | 357.41 | 2.04 | 113.61 | 224.76 | 1.98 | 152.6 | 424.7 | 2.78 | 2.27 |
| BC012247 | 67880 | 275.62 | 657.22 | 2.38 | 262.56 | 638.46 | 2.43 | 305.33 | 604.16 | 1.98 | 2.26 |
| BE859736 | 68949 | 1370.36 | 3100.41 | 2.26 | 1680.73 | 3691.52 | 2.2 | 1540.59 | 3591.51 | 2.33 | 2.26 |
| AV345051 | 234094 | 63.07 | 145.34 | 2.3 | 64.04 | 96.32 | 1.5 | 55.76 | 166.48 | 2.99 | 2.26 |
| NM_011020 | 18415 | 376.98 | 791.46 | 2.1 | 252.79 | 547.69 | 2.17 | 304.97 | 765.88 | 2.51 | 2.26 |
| BB222127 | 67458 | 292.87 | 615.94 | 2.1 | 275.61 | 550.01 | 2 | 222.35 | 596.77 | 2.68 | 2.26 |
| BG063931 | 233575 | 350.15 | 835.71 | 2.39 | 232.71 | 676.59 | 2.91 | 400.94 | 589.21 | 1.47 | 2.26 |
| BB667677 | 66271 | 1182.92 | 2540.76 | 2.15 | 907.17 | 2398.42 | 2.64 | 1074.2 | 2111.72 | 1.97 | 2.25 |
| NM_025304 | 30949 | 496.97 | 1135.68 | 2.29 | 296.78 | 786.89 | 2.65 | 489.99 | 890.53 | 1.82 | 2.25 |
| AK019325 | 100038882 /// 100044225 /// 53606 /// 677168 | 135.75 | 250.47 | 1.85 | 131.31 | 339.33 | 2.58 | 154.84 | 360.51 | 2.33 | 2.25 |
| BF683028 | 14933 | 88.16 | 257.75 | 2.92 | 109.7 | 197.52 | 1.8 | 112.28 | 228.88 | 2.04 | 2.25 |
| AV114231 | 100045971 /// 67623 | 36.65 | 109.45 | 2.99 | 59.58 | 117.5 | 1.97 | 68.65 | 123.45 | 1.8 | 2.25 |
| AI510297 | 212772 | 747.62 | 1653.34 | 2.21 | 642.05 | 1496.82 | 2.33 | 945.01 | 2088.86 | 2.21 | 2.25 |
| NM_026172 | 67460 | 283.38 | 543.53 | 1.92 | 158.36 | 425.41 | 2.69 | 251.61 | 538.43 | 2.14 | 2.25 |
| C79823 | 67036 | 831.08 | 1490.54 | 1.79 | 549.84 | 1675.61 | 3.05 | 924.48 | 1759.63 | 1.9 | 2.25 |
| BB407228 | 17220 | 543.44 | 1153.09 | 2.12 | 412.13 | 832.73 | 2.02 | 464.67 | 1209.54 | 2.6 | 2.25 |
| C81400 | 65970 | 354.97 | 928.88 | 2.62 | 151.75 | 392 | 2.58 | 463.46 | 714.59 | 1.54 | 2.25 |
| AI639807 | 67138 | 222.53 | 401.27 | 1.8 | 66.27 | 181.23 | 2.73 | 187.53 | 413.56 | 2.21 | 2.25 |
| AV013305 | 68808 | 97.02 | 169.98 | 1.75 | 41.18 | 122.53 | 2.98 | 67.99 | 136.33 | 2.01 | 2.25 |
| BC006736 | 75430 | 131.16 | 298.24 | 2.27 | 193.89 | 316.21 | 1.63 | 114.26 | 322.88 | 2.83 | 2.24 |
| AK005765 | 75497 | 66.89 | 159.82 | 2.39 | 76.49 | 171.91 | 2.25 | 95.95 | 200.88 | 2.09 | 2.24 |
| BC028766 | 78372 | 575 | 1135.33 | 1.97 | 520.86 | 1039.93 | 2 | 445.69 | 1230.65 | 2.76 | 2.24 |
| BG070186 | 211651 | 82.5 | 185.79 | 2.25 | 64.94 | 106.23 | 1.64 | 61.07 | 173.26 | 2.84 | 2.24 |
| NM_011196 | 19218 | 250.15 | 433.21 | 1.73 | 72.45 | 159.08 | 2.2 | 237 | 660.93 | 2.79 | 2.24 |
| BI409701 | 230752 | 766.41 | 1687.35 | 2.2 | 655.18 | 1835.75 | 2.8 | 696.19 | 1199.58 | 1.72 | 2.24 |
| BB702347 | 54392 | 240.9 | 420.5 | 1.75 | 101.49 | 210.09 | 2.07 | 177.57 | 514.83 | 2.9 | 2.24 |
| BG084230 | 66824 | 2308.11 | 4656.25 | 2.02 | 1570.39 | 3959.3 | 2.52 | 2117.18 | 4599.81 | 2.17 | 2.24 |
| BG069095 | 15900 | 164.33 | 443.76 | 2.7 | 232.96 | 290.95 | 1.25 | 166.06 | 458.74 | 2.76 | 2.24 |
| AV216351 | 30954 /// 668686 /// 676549 | 209.09 | 549.85 | 2.63 | 367.86 | 648.54 | 1.76 | 290.31 | 673.32 | 2.32 | 2.24 |
| NM_019499 | 56150 | 806.31 | 1783.33 | 2.21 | 625.03 | 1297.34 | 2.08 | 635.46 | 1528.32 | 2.41 | 2.23 |
| NM_025960 | 67091 | 536.31 | 991.29 | 1.85 | 406.57 | 665.59 | 1.64 | 499.92 | 1605.17 | 3.21 | 2.23 |
| NM_009387 | 21877 | 361.07 | 791.68 | 2.19 | 178.71 | 436.65 | 2.44 | 425.11 | 880.13 | 2.07 | 2.23 |
| BB010153 | 75007 | 229.55 | 511.83 | 2.23 | 153.68 | 351.56 | 2.29 | 212.09 | 461.47 | 2.18 | 2.23 |
| NM_024438 | 68082 | 1202.76 | 1938.91 | 1.61 | 414.93 | 1255.6 | 3.03 | 970.87 | 1988.01 | 2.05 | 2.23 |
| AK012087 | 70028 | 409.01 | 993.15 | 2.43 | 299.34 | 668.91 | 2.23 | 448.93 | 911.23 | 2.03 | 2.23 |
| BG071597 | 70361 | 393.35 | 658.4 | 1.67 | 188.13 | 538.32 | 2.86 | 329.89 | 712.02 | 2.16 | 2.23 |
| AA590970 | 29816 | 978.65 | 2273.73 | 2.32 | 1131.76 | 2806.34 | 2.48 | 1366.65 | 2568.48 | 1.88 | 2.23 |
| BI963682 | 106878 | 617.43 | 1319.64 | 2.14 | 846.28 | 1507.9 | 1.78 | 539.29 | 1486.93 | 2.76 | 2.23 |
| AI747289 | 74122 | 594.89 | 1279.15 | 2.15 | 492.17 | 1078.35 | 2.19 | 554.39 | 1299.71 | 2.34 | 2.23 |
| BB826401 | 216858 | 160.35 | 231.96 | 1.45 | 135.46 | 181.64 | 1.34 | 121.31 | 471.7 | 3.89 | 2.23 |
| NM_028744 | 67073 | 136.17 | 289.09 | 2.12 | 115.34 | 229.34 | 1.99 | 115.19 | 296.58 | 2.57 | 2.23 |
| D17546 | 12822 | 100.3 | 156.74 | 1.56 | 96.56 | 149.85 | 1.55 | 97.62 | 348.37 | 3.57 | 2.23 |
| NM_009121 | 20229 | 2658.38 | 6379.28 | 2.4 | 2273.63 | 4705.76 | 2.07 | 3331.15 | 7332.47 | 2.2 | 2.22 |
| NM_010492 | 15893 | 340.53 | 742.88 | 2.18 | 370.64 | 868.5 | 2.34 | 298.59 | 643.45 | 2.15 | 2.22 |
| BB833716 | 22129 | 320.1 | 759.59 | 2.37 | 220.15 | 596.86 | 2.71 | 268.3 | 425.57 | 1.59 | 2.22 |
| NM_011146 | 19016 | 142.78 | 332.27 | 2.33 | 109.94 | 227.28 | 2.07 | 281.17 | 634.22 | 2.26 | 2.22 |
| NM_009448 | 22146 /// 626534 | 104.73 | 285.8 | 2.73 | 146.82 | 264.61 | 1.8 | 140.53 | 299.29 | 2.13 | 2.22 |
| AF199010 | 56524 | 276.28 | 548.5 | 1.99 | 315.75 | 572.41 | 1.81 | 232.45 | 661.4 | 2.85 | 2.22 |
| BC011292 | 20524 | 384.9 | 635.19 | 1.65 | 210.85 | 572.73 | 2.72 | 325.01 | 739.05 | 2.27 | 2.21 |
| NM_134079 | 11534 | 130.22 | 239.85 | 1.84 | 117.04 | 271.83 | 2.32 | 125.99 | 312.42 | 2.48 | 2.21 |
| BC023421 | 73833 | 732.18 | 1363.03 | 1.86 | 571.57 | 1267.79 | 2.22 | 694.65 | 1768.83 | 2.55 | 2.21 |
| BB794772 | 17909 | 111.99 | 236.43 | 2.11 | 109.27 | 237.89 | 2.18 | 107.95 | 252.21 | 2.34 | 2.21 |
| BE456782 | 71268 | 421.65 | 780.04 | 1.85 | 466.57 | 1035.79 | 2.22 | 358.79 | 916.27 | 2.55 | 2.21 |
| AK004037 | 64658 | 565.92 | 1068.33 | 1.89 | 264.22 | 732.49 | 2.77 | 470.15 | 921.37 | 1.96 | 2.21 |
| AV095209 | 270685 | 611.5 | 950.03 | 1.55 | 580.73 | 631.1 | 1.09 | 589.02 | 2340.01 | 3.97 | 2.20 |
| NM_134095 | 28075 | 617.52 | 981.56 | 1.59 | 351.01 | 915.92 | 2.61 | 622.52 | 1499.49 | 2.41 | 2.20 |
| AW537824 | 100044896 /// 109232 | 47.15 | 86.85 | 1.84 | 52.74 | 80.33 | 1.52 | 47.21 | 153.31 | 3.25 | 2.20 |
| AF366401 | 55942 | 712.13 | 1295.31 | 1.82 | 476.15 | 782.87 | 1.64 | 555.53 | 1749.47 | 3.15 | 2.20 |
| M63801 | 14609 | 153.26 | 315.52 | 2.06 | 83 | 202.82 | 2.44 | 113.99 | 240.21 | 2.11 | 2.20 |
| BC006732 | 13056 | 118.85 | 191.8 | 1.61 | 211.89 | 215.16 | 1.02 | 64.21 | 254.93 | 3.97 | 2.20 |
| BQ044016 | 13800 | 98.57 | 153.55 | 1.56 | 96.2 | 243.23 | 2.53 | 101.99 | 255.87 | 2.51 | 2.20 |
| BG076340 | 80291 | 1985.77 | 3800.81 | 1.91 | 1507.13 | 4161.49 | 2.76 | 2240.96 | 4300.04 | 1.92 | 2.20 |
| AI115397 | 114663 | 371.71 | 518.77 | 1.4 | 193.3 | 301.78 | 1.56 | 295.42 | 1072.93 | 3.63 | 2.20 |
| BM502719 | 280411 | 166.21 | 288.16 | 1.73 | 92.41 | 184.1 | 1.99 | 113.99 | 326.87 | 2.87 | 2.20 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| AK007802 | 100043855 /// 100044632 /// 15382 /// 434856 /// 654467 /// 665646 | 2306.22 | 4615.71 | 2 | 2473.13 | 4634.17 | 1.87 | 2106.86 | 5707.9 | 2.71 | 2.19 |
| NM_018871 | 22628 | 274.03 | 538.79 | 1.97 | 122.79 | 272.35 | 2.22 | 205.21 | 489.72 | 2.39 | 2.19 |
| BE853286 | 109711 | 88.86 | 155.16 | 1.75 | 128.1 | 417.77 | 3.26 | 84.37 | 132.52 | 1.57 | 2.19 |
| NM_026410 | 67849 | 441.78 | 958.42 | 2.17 | 356.73 | 717.13 | 2.01 | 464.14 | 1107.49 | 2.39 | 2.19 |
| BG965431 | 27388 | 272.57 | 499.47 | 1.83 | 170.36 | 478.96 | 2.81 | 284.24 | 549.97 | 1.93 | 2.19 |
| AF059029 | 108058 | 121.47 | 262.01 | 2.16 | 137.67 | 304.38 | 2.21 | 124.7 | 273.71 | 2.19 | 2.19 |
| BB200911 | | 60.69 | 87.55 | 1.44 | 108.51 | 295.29 | 2.72 | 71.84 | 171.74 | 2.39 | 2.18 |
| BM207588 | 20525 | 870.24 | 1561.19 | 1.79 | 1316.83 | 1212.54 | −1.09 | 785.5 | 4594.38 | 5.85 | 2.18 |
| BB095626 | 67458 | 397.22 | 849.24 | 2.14 | 354.66 | 724.22 | 2.04 | 313.98 | 745.38 | 2.37 | 2.18 |
| BG066131 | 233806 | 350.16 | 878.11 | 2.51 | 352.39 | 776.93 | 2.2 | 340.17 | 627.15 | 1.84 | 2.18 |
| NM_010371 | 14940 | 122.87 | 207.98 | 1.69 | 86.43 | 168.74 | 1.95 | 114.57 | 331.58 | 2.89 | 2.18 |
| BB133021 | 320209 | 116.24 | 267.26 | 2.3 | 71.57 | 164.72 | 2.3 | 100.56 | 194.1 | 1.93 | 2.18 |
| NM_023707 | 100040208 /// 100044143 /// 73626 | 63.8 | 144 | 2.26 | 111.99 | 252.52 | 2.25 | 75.38 | 152.61 | 2.02 | 2.18 |
| NM_020282 | 18105 | 863.39 | 1299.75 | 1.51 | 225.82 | 735.58 | 3.26 | 934.45 | 1634.43 | 1.75 | 2.17 |
| BB621938 | 99382 | 320.32 | 632.51 | 1.97 | 531.76 | 1294.36 | 2.43 | 325.09 | 690.56 | 2.12 | 2.17 |
| AI837704 | 234593 | 192.58 | 368.75 | 1.91 | 133.17 | 312.18 | 2.34 | 178.82 | 405.85 | 2.27 | 2.17 |
| NM_025415 | 100039474 /// 100044764 /// 66197 | 1340.3 | 2512.77 | 1.87 | 1772.04 | 3113.49 | 1.76 | 1220.23 | 3519.33 | 2.88 | 2.17 |
| AK004190 | 30057 | 1070.76 | 2125.21 | 1.98 | 983.05 | 2179.45 | 2.22 | 973.71 | 2244.85 | 2.31 | 2.17 |
| AI316747 | 107684 | 406.91 | 1087.87 | 2.67 | 662.1 | 1022.84 | 1.54 | 306.94 | 705.57 | 2.3 | 2.17 |
| AV270020 | 212999 | 361.22 | 977.37 | 2.71 | 285.78 | 452.67 | 1.58 | 420.39 | 931.56 | 2.22 | 2.17 |
| AK011367 | 70533 | 227.69 | 629.16 | 2.76 | 450.26 | 744.38 | 1.65 | 258.4 | 542.83 | 2.1 | 2.17 |
| BI134771 | 14586 | 137.31 | 353.85 | 2.58 | 72.4 | 138.32 | 1.91 | 162.64 | 328.23 | 2.02 | 2.17 |
| BB025778 | 319266 | 121.22 | 229.05 | 1.89 | 71.93 | 177.27 | 2.46 | 104.28 | 225.14 | 2.16 | 2.17 |
| NM_009448 | 22146 /// 626534 | 1684.11 | 2661.79 | 1.58 | 1266.98 | 2429.3 | 1.92 | 1220.8 | 3644.61 | 2.99 | 2.16 |
| NM_010191 | 14137 | 469.76 | 881.28 | 1.88 | 337.4 | 546.31 | 1.62 | 433.99 | 1297.33 | 2.99 | 2.16 |
| BG919998 | 53416 | 184.6 | 458.87 | 2.49 | 166.79 | 313.58 | 1.88 | 199.88 | 422.9 | 2.12 | 2.16 |
| BM205349 | 75317 | 72.77 | 172.84 | 2.38 | 43.42 | 67.01 | 1.54 | 63.97 | 164.61 | 2.57 | 2.16 |
| AU043467 | 69928 | 69.7 | 145.95 | 2.09 | 54.09 | 113.78 | 2.1 | 68.84 | 158.58 | 2.3 | 2.16 |
| AF196480 | 23947 | 385.91 | 754.74 | 1.96 | 272.67 | 577.53 | 2.12 | 280.37 | 672.03 | 2.4 | 2.16 |
| BM230253 | 72155 | 86.77 | 173.94 | 2 | 66.54 | 134.96 | 2.03 | 75.96 | 186.18 | 2.45 | 2.16 |
| BB360213 | 214058 | 46.89 | 89.52 | 1.91 | 43.13 | 94.34 | 2.19 | 52.91 | 125.79 | 2.38 | 2.16 |
| AY075132 | 71586 | 655.92 | 1310.53 | 2 | 498.49 | 1085.15 | 2.18 | 522.76 | 1196.23 | 2.29 | 2.16 |
| BC019453 | 108143 | 414.53 | 658.59 | 1.59 | 156.64 | 474.25 | 3.03 | 399.55 | 740.16 | 1.85 | 2.16 |
| NM_009748 | 12068 | 374.66 | 606.82 | 1.62 | 137.44 | 380.16 | 2.77 | 285.82 | 593.77 | 2.08 | 2.16 |
| AK012154 | 23874 | 118.94 | 244.53 | 2.06 | 141.01 | 384.08 | 2.72 | 116.22 | 196.93 | 1.69 | 2.16 |
| BB070019 | 17155 | 878.3 | 2056.25 | 2.34 | 1000.59 | 2248.59 | 2.25 | 1056.7 | 1975.67 | 1.87 | 2.15 |
| AK012776 | 353208 | 494.8 | 1028.93 | 2.08 | 325.85 | 797.69 | 2.45 | 475.19 | 914.84 | 1.93 | 2.15 |
| BB243653 | | 162.43 | 451.75 | 2.78 | 136.52 | 218.16 | 1.6 | 157.76 | 328.63 | 2.08 | 2.15 |
| BM234794 | 68166 | 60.56 | 126.48 | 2.09 | 73.95 | 132.94 | 1.8 | 58.25 | 149.75 | 2.57 | 2.15 |
| NM_019716 | 56452 | 240.37 | 532.67 | 2.22 | 450.27 | 679.89 | 1.51 | 205.57 | 559.86 | 2.72 | 2.15 |
| AK007802 | 15382 | 2118.75 | 4079.6 | 1.93 | 2572.13 | 4324.75 | 1.68 | 1868.01 | 5296.65 | 2.84 | 2.15 |
| NM_019780 | 56433 | 1339.3 | 2520.41 | 1.88 | 812.6 | 2249.34 | 2.77 | 1374.47 | 2478.48 | 1.8 | 2.15 |
| NM_030254 | 80286 | 607.71 | 1556.76 | 2.56 | 634.28 | 1496.83 | 2.36 | 736.27 | 1129.41 | 1.53 | 2.15 |
| BE692107 | 18124 | 128.53 | 330.88 | 2.57 | 91 | 242.3 | 2.66 | 131.45 | 159.47 | 1.21 | 2.15 |
| NM_018734 | 55932 | 576.2 | 1177.43 | 2.04 | 380.97 | 1041.87 | 2.73 | 943.14 | 1575.89 | 1.67 | 2.15 |
| AK002362 | 17918 | 498.15 | 1013.69 | 2.03 | 425.85 | 1035.34 | 2.43 | 450.7 | 893.23 | 1.98 | 2.15 |
| BB268139 | 268291 | 292.17 | 478.62 | 1.64 | 198.75 | 316.09 | 1.59 | 241.15 | 773.11 | 3.21 | 2.15 |
| BM118729 | 75007 | 134.38 | 310.85 | 2.31 | 112.38 | 245.67 | 2.19 | 168.89 | 327.13 | 1.94 | 2.15 |
| BC008166 | 100039683 /// 100045937 /// 100047518 /// 76281 | 541.8 | 1014.2 | 1.87 | 352.22 | 960.16 | 2.73 | 478.75 | 875.54 | 1.83 | 2.14 |
| AK003874 | 71793 | 252.16 | 556.25 | 2.21 | 337.94 | 632.59 | 1.87 | 254.23 | 597.44 | 2.35 | 2.14 |
| BI658203 | 212999 | 158.79 | 433.18 | 2.73 | 128.53 | 228.94 | 1.78 | 164.14 | 315.65 | 1.92 | 2.14 |
| BG070404 | 76843 | 60.74 | 151.96 | 2.5 | 73.45 | 141.32 | 1.92 | 63.15 | 127.06 | 2.01 | 2.14 |
| NM_019999 | 56695 | 448.99 | 728.93 | 1.62 | 217.42 | 674.88 | 3.1 | 480.31 | 818.21 | 1.7 | 2.14 |
| BC010332 | 50784 | 345.58 | 608.07 | 1.76 | 291.95 | 480.92 | 1.65 | 292.28 | 878.11 | 3 | 2.14 |
| AV330726 | 14609 | 95.36 | 198.82 | 2.08 | 51.9 | 112.46 | 2.17 | 63.75 | 137.89 | 2.16 | 2.14 |
| NM_008380 | 16323 | 246.71 | 490.33 | 1.99 | 167.77 | 356.37 | 2.12 | 256.36 | 587.32 | 2.29 | 2.13 |
| BC003284 | 73828 | 182.72 | 394.53 | 2.16 | 180.03 | 351.04 | 1.95 | 168.77 | 386.59 | 2.29 | 2.13 |
| BB150520 | 13209 | 131.92 | 390.76 | 2.96 | 125.39 | 238.88 | 1.91 | 153.72 | 234.77 | 1.53 | 2.13 |
| AV215438 | 17357 /// 668321 | 241.54 | 481.36 | 1.99 | 376.42 | 860.75 | 2.29 | 345.49 | 728.01 | 2.11 | 2.13 |
| NM_008021 | 14235 | 68.25 | 149.89 | 2.2 | 62.79 | 138.97 | 2.21 | 75.27 | 148.94 | 1.98 | 2.13 |
| BI903628 | 66400 | 526.66 | 804.01 | 1.53 | 212.96 | 584.82 | 2.75 | 365.98 | 767.08 | 2.1 | 2.13 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| BC022954 | 20964 | 150.99 | 315.84 | 2.09 | 154.79 | 335.08 | 2.16 | 150.66 | 321.03 | 2.13 | 2.13 |
| AK011781 | 72482 | 368.97 | 783.49 | 2.12 | 402.22 | 874.87 | 2.18 | 429.35 | 887.4 | 2.07 | 2.12 |
| AV354240 | 14586 | 285.34 | 687.04 | 2.41 | 92.19 | 203.13 | 2.2 | 282.3 | 495.71 | 1.76 | 2.12 |
| BM207954 | 211586 /// 319491 | 132.97 | 355.74 | 2.68 | 186.11 | 358.97 | 1.93 | 144.12 | 253.75 | 1.76 | 2.12 |
| AK004813 | 71729 | 114.85 | 229.81 | 2 | 123.12 | 192.85 | 1.57 | 122.31 | 342.74 | 2.8 | 2.12 |
| AA561726 | 236539 /// 665516 /// 666036 /// 668771 /// 675316 | 894.4 | 2211.05 | 2.47 | 792.56 | 1751.42 | 2.21 | 970.56 | 1639.1 | 1.69 | 2.12 |
| NM_010119 | 13660 | 365.59 | 824.06 | 2.25 | 387.03 | 919.68 | 2.38 | 477.84 | 827.31 | 1.73 | 2.12 |
| NM_030678 | 14936 | 154.26 | 269.79 | 1.75 | 75.18 | 126.76 | 1.69 | 160.38 | 468.14 | 2.92 | 2.12 |
| NM_025424 | 66208 | 87.31 | 208.02 | 2.38 | 109.03 | 204.45 | 1.88 | 112.42 | 236.13 | 2.1 | 2.12 |
| BM114154 | 100045217 /// 230157 | 45.83 | 89.89 | 1.96 | 47.77 | 105.25 | 2.2 | 56.27 | 123.33 | 2.19 | 2.12 |
| AI510221 | 67391 | 1582.14 | 3111.4 | 1.97 | 1411.29 | 3101.61 | 2.2 | 1421.27 | 3078.8 | 2.17 | 2.11 |
| BC024597 | 75812 | 426.4 | 1002.61 | 2.35 | 389 | 934.89 | 2.4 | 385.34 | 611.63 | 1.59 | 2.11 |
| NM_025951 | 67073 | 327.54 | 638.78 | 1.95 | 313.34 | 621.01 | 1.98 | 295.9 | 714.02 | 2.41 | 2.11 |
| NM_009196 | 20501 | 219.26 | 345.15 | 1.57 | 423.39 | 595.75 | 1.41 | 178.49 | 598.5 | 3.35 | 2.11 |
| BE991811 | 217124 | 153.07 | 327.14 | 2.14 | 174.71 | 346.06 | 1.98 | 227.39 | 502.44 | 2.21 | 2.11 |
| NM_026202 | 67501 | 124.28 | 212.69 | 1.71 | 59 | 182.03 | 3.09 | 94.63 | 143.89 | 1.52 | 2.11 |
| BM937727 |  | 55.68 | 113.35 | 2.04 | 46.28 | 96.82 | 2.09 | 41.82 | 91.57 | 2.19 | 2.11 |
| NM_008838 | 18701 | 646.49 | 1105.49 | 1.71 | 260.12 | 708.62 | 2.72 | 576.03 | 1088.02 | 1.89 | 2.11 |
| AF339910 | 18605 | 149.95 | 286.73 | 1.91 | 196.62 | 546.79 | 2.78 | 179.98 | 293.65 | 1.63 | 2.11 |
| BB204380 | 12775 | 116.65 | 191.11 | 1.64 | 137.73 | 466.38 | 3.39 | 138.11 | 177.28 | 1.28 | 2.10 |
| NM_009214 | 20603 /// 671878 | 1410.31 | 2648.78 | 1.88 | 826.65 | 2378.81 | 2.88 | 1570.37 | 2436.69 | 1.55 | 2.10 |
| AK010029 | 67041 | 1000.78 | 1771.85 | 1.77 | 379.19 | 1188.34 | 3.13 | 1072.11 | 1501.58 | 1.4 | 2.10 |
| BB234940 | 12305 | 238.19 | 442.78 | 1.86 | 85.43 | 152.92 | 1.79 | 158.52 | 420.8 | 2.65 | 2.10 |
| NM_023066 | 65973 | 139.62 | 244.97 | 1.75 | 106.53 | 186.79 | 1.75 | 114.91 | 321.93 | 2.8 | 2.10 |
| AF054581 |  | 387.49 | 719.75 | 1.86 | 287.52 | 555.07 | 1.93 | 515.31 | 1286.19 | 2.5 | 2.10 |
| NM_009344 | 21664 | 861.85 | 2080.96 | 2.41 | 1191.19 | 2312.98 | 1.94 | 1247.49 | 2415.97 | 1.94 | 2.10 |
| BC004752 | 69660 | 658.25 | 1496.89 | 2.27 | 637.43 | 1163.45 | 1.83 | 648.47 | 1418.61 | 2.19 | 2.10 |
| AV253518 | 20322 | 200.38 | 553 | 2.76 | 174.07 | 322.3 | 1.85 | 309.94 | 521.1 | 1.68 | 2.10 |
| AV370040 | 242484 | 940.81 | 1674.95 | 1.78 | 260.98 | 861.5 | 3.3 | 1062.97 | 1271.43 | 1.2 | 2.09 |
| BG069767 | 27050 | 503.85 | 1244.51 | 2.47 | 583.81 | 999.46 | 1.71 | 513.39 | 1077.36 | 2.1 | 2.09 |
| BC021523 | 223752 | 187.79 | 519.51 | 2.77 | 298.3 | 575.17 | 1.93 | 200.64 | 317.95 | 1.58 | 2.09 |
| NM_009929 | 12822 | 93.5 | 167.48 | 1.79 | 119.46 | 139.15 | 1.16 | 95.94 | 319.36 | 3.33 | 2.09 |
| BB458835 | 30926 | 1904.97 | 3577.2 | 1.88 | 1423.81 | 3262.87 | 2.29 | 1855.3 | 3888.38 | 2.1 | 2.09 |
| AA590970 | 29816 | 417.25 | 871.49 | 2.09 | 404.66 | 1077.25 | 2.66 | 648.07 | 987.57 | 1.52 | 2.09 |
| NM_011132 | 18973 | 157.76 | 303.81 | 1.93 | 130.9 | 239.58 | 1.83 | 136.81 | 342.77 | 2.51 | 2.09 |
| BC016456 | 69459 | 500.33 | 1318.78 | 2.64 | 398.24 | 991.56 | 2.49 | 810.56 | 918.35 | 1.13 | 2.09 |
| AF229434 | 21936 | 3829.32 | 6414.36 | 1.68 | 2319.14 | 5236.34 | 2.26 | 3630.77 | 8432.08 | 2.32 | 2.09 |
| AV020390 | 22333 | 1586.75 | 2743.35 | 1.73 | 1440.29 | 2343.62 | 1.63 | 1492.22 | 4334.1 | 2.9 | 2.09 |
| BC003432 | 110842 | 1260.28 | 2260.06 | 1.79 | 719.58 | 1915.71 | 2.66 | 1214.07 | 2196.63 | 1.81 | 2.09 |
| BG064103 | 22029 | 1657.49 | 2001.82 | 1.21 | 276.65 | 1053.75 | 3.81 | 1696.66 | 2103.28 | 1.24 | 2.09 |
| BE197524 | 14469 | 921.3 | 1466.75 | 1.59 | 427.68 | 1264.7 | 2.96 | 1020.19 | 1739.73 | 1.71 | 2.09 |
| NM_007657 | 12527 | 258.3 | 640.17 | 2.48 | 743.21 | 1811.34 | 2.44 | 281.15 | 375.66 | 1.34 | 2.09 |
| NM_021477 | 268859 | 216 | 435.03 | 2.01 | 66.74 | 175.65 | 2.63 | 196.48 | 318.55 | 1.62 | 2.09 |
| NM_016741 | 20778 | 154.46 | 300.25 | 1.94 | 123.02 | 280.83 | 2.28 | 164.44 | 334.92 | 2.04 | 2.09 |
| BM234652 | 50527 | 1284.17 | 1549.71 | 1.21 | 544.42 | 717.48 | 1.32 | 1200.86 | 4463.11 | 3.72 | 2.08 |
| BI151440 | 12495 | 510.71 | 615.15 | 1.2 | 222.7 | 240.05 | 1.08 | 362.98 | 1442.58 | 3.97 | 2.08 |
| AV302436 | 665401 /// 67383 /// 677553 | 224.87 | 495.37 | 2.2 | 192.1 | 420.47 | 2.19 | 193.91 | 361.17 | 1.86 | 2.08 |
| BC009150 | 67286 | 172.24 | 281.69 | 1.64 | 137.49 | 297.34 | 2.16 | 133.09 | 326.15 | 2.45 | 2.08 |
| AK003718 | 15258 | 538.29 | 1402.81 | 2.61 | 413.83 | 1003.86 | 2.43 | 702.68 | 843.39 | 1.2 | 2.08 |
| BC017138 | 109168 | 182.03 | 337.79 | 1.86 | 158.53 | 344.31 | 2.17 | 179.27 | 396.94 | 2.21 | 2.08 |
| NM_021782 | 547223 /// 60505 /// 637754 | 138.6 | 127.85 | −1.08 | 64.67 | 322.94 | 4.99 | 173.12 | 402.73 | 2.33 | 2.08 |
| BB093469 | 69941 | 103.7 | 203.05 | 1.96 | 110.93 | 170.58 | 1.54 | 104.73 | 286.97 | 2.74 | 2.08 |
| NM_009895 | 12700 | 769.56 | 2010.58 | 2.61 | 2197.33 | 3217.86 | 1.46 | 816.94 | 1764.37 | 2.16 | 2.08 |
| AV280756 | 207607 | 186.17 | 354.22 | 1.9 | 130.26 | 323.17 | 2.48 | 186.86 | 344.84 | 1.85 | 2.08 |
| AW553304 | 12014 | 69.22 | 130.87 | 1.89 | 108.51 | 592.51 | 5.46 | 74.69 | 66.87 | −1.12 | 2.08 |
| AU019880 |  | 89.44 | 275.12 | 3.08 | 79.87 | 120.44 | 1.51 | 139.26 | 228.92 | 1.64 | 2.08 |
| BB093351 | 381306 | 60.16 | 106.61 | 1.77 | 46.76 | 70.76 | 1.51 | 47.27 | 138.76 | 2.94 | 2.07 |
| BB204486 | 224870 /// 236539 /// 382931 /// 385344 /// 545530 /// 627427 /// 630761 /// | 822.79 | 2005.8 | 2.44 | 777.18 | 1634.54 | 2.1 | 888.79 | 1489.06 | 1.68 | 2.07 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| | 630896 /// 637235 /// 665516 /// 666036 /// 666422 /// 666875 /// 668506 /// 668576 /// 668771 /// 675010 /// 675316 /// 675710 /// 677380 | | | | | | | | | | |
| BC024693 | 67199 | 878.46 | 1507.91 | 1.72 | 601.52 | 1655.75 | 2.75 | 946.07 | 1655.99 | 1.75 | 2.07 |
| BM234765 | 20620 | 251.52 | 609.35 | 2.42 | 256.43 | 483.21 | 1.88 | 246.08 | 472.14 | 1.92 | 2.07 |
| NM_007987 | 14102 | 161.54 | 300.03 | 1.86 | 111.05 | 294.22 | 2.65 | 178.93 | 305.4 | 1.71 | 2.07 |
| BF016392 | 77777 | 117.95 | 223.94 | 1.9 | 101.47 | 238.61 | 2.35 | 100.57 | 198.26 | 1.97 | 2.07 |
| BB833716 | 22129 | 589.32 | 1228.16 | 2.08 | 448.5 | 1006.74 | 2.24 | 454.44 | 858.68 | 1.89 | 2.07 |
| AV260647 | 67005 | 662.22 | 1034.78 | 1.56 | 360.65 | 758.99 | 2.1 | 487.01 | 1240.67 | 2.55 | 2.07 |
| NM_025512 | 66361 | 355.97 | 804.52 | 2.26 | 334.20 | 711.07 | 2.13 | 366.16 | 665.97 | 1.82 | 2.07 |
| AK004037 | 64658 | 185.95 | 349.53 | 1.88 | 78.13 | 178.71 | 2.29 | 155.91 | 317.7 | 2.04 | 2.07 |
| AK009497 | 69568 | 231.62 | 504.37 | 2.18 | 214.26 | 420.12 | 1.96 | 209.12 | 431.04 | 2.06 | 2.07 |
| NM_019990 | 56018 | 301.65 | 748.92 | 2.48 | 498.47 | 706.01 | 1.42 | 381.8 | 876.16 | 2.29 | 2.06 |
| BB458178 | 105501 | 1619.06 | 2764.03 | 1.71 | 838.26 | 2302.2 | 2.75 | 1393.3 | 2392.59 | 1.72 | 2.06 |
| AV059518 | 67117 | 1004.35 | 2096.53 | 2.09 | 812.5 | 1495.08 | 1.84 | 875.54 | 1966.67 | 2.25 | 2.06 |
| NM_016761 | 100042970 /// 100044006 /// 100044746 /// 16580 | 150.11 | 263.77 | 1.76 | 116.64 | 202.4 | 1.74 | 114.01 | 305.41 | 2.68 | 2.06 |
| BB364961 | | 94.25 | 185.35 | 1.97 | 126.27 | 227.47 | 1.8 | 104.46 | 250.5 | 2.4 | 2.06 |
| BF303544 | 56491 | 303.74 | 827.85 | 2.73 | 579.36 | 1186.27 | 2.05 | 714.05 | 981.92 | 1.38 | 2.05 |
| BC008238 | 56791 | 64.44 | 149.3 | 2.32 | 74.24 | 167.46 | 2.26 | 62.27 | 98.28 | 1.58 | 2.05 |
| BB449218 | 67071 | 47.01 | 87.24 | 1.86 | 72.29 | 149.22 | 2.06 | 52.92 | 118.36 | 2.24 | 2.05 |
| AK010005 | 71924 | 97.02 | 200.95 | 2.07 | 77 | 124.61 | 1.62 | 107.26 | 263.9 | 2.46 | 2.05 |
| BE988432 | 65247 | 81.76 | 181.22 | 2.22 | 94.4 | 179.31 | 1.9 | 100.41 | 203.97 | 2.03 | 2.05 |
| AV328388 | 17196 | 80.37 | 183.33 | 2.28 | 165.49 | 179.66 | 1.09 | 60.5 | 168.21 | 2.78 | 2.05 |
| BF466605 | 66337 | 86.7 | 179.45 | 2.07 | 75.43 | 176.79 | 2.34 | 90.6 | 157.56 | 1.74 | 2.05 |
| AF237702 | 20425 | 78.83 | 161.9 | 2.05 | 95.54 | 142.64 | 1.49 | 73.59 | 192.35 | 2.61 | 2.05 |
| NM_011303 | 20148 | 441.15 | 1194.82 | 2.71 | 484.38 | 850.3 | 1.76 | 658.59 | 1105.49 | 1.68 | 2.05 |
| NM_007522 | 12015 | 219.43 | 377.29 | 1.72 | 121.38 | 294.96 | 2.43 | 193.24 | 384.13 | 1.99 | 2.05 |
| BE950435 | 74023 | 83.79 | 176.86 | 2.11 | 91.21 | 138.74 | 1.52 | 81.33 | 204.17 | 2.51 | 2.05 |
| NM_010585 | 16438 | 886.88 | 1569.08 | 1.77 | 555.3 | 1047.89 | 1.89 | 786.94 | 1946.85 | 2.47 | 2.04 |
| BI658203 | 212999 | 246.06 | 666.61 | 2.71 | 201.82 | 296.34 | 1.47 | 309.75 | 603.72 | 1.95 | 2.04 |
| BB283759 | 12995 | 169.17 | 320.39 | 1.89 | 149.9 | 272.91 | 1.82 | 158.89 | 383.65 | 2.41 | 2.04 |
| NM_024223 | 68337 | 134.34 | 302.57 | 2.25 | 168.69 | 230.75 | 1.37 | 124.29 | 310.88 | 2.5 | 2.04 |
| AI461712 | 70984 | 186.98 | 397.5 | 2.13 | 106.63 | 153.04 | 1.44 | 146.56 | 373.65 | 2.55 | 2.04 |
| BC008161 | 68533 | 837.11 | 1573.77 | 1.88 | 1771.7 | 2217.11 | 1.25 | 761.56 | 2269.65 | 2.98 | 2.04 |
| NM_021451 | 58801 | 768.72 | 1937.88 | 2.52 | 1358.05 | 1745.57 | 1.29 | 959.46 | 2206.59 | 2.3 | 2.04 |
| X58876 | 17246 | 852.2 | 1607.24 | 1.89 | 779.75 | 1578.04 | 2.02 | 839.5 | 1850.15 | 2.2 | 2.04 |
| AK015214 | 67138 | 386.78 | 642.92 | 1.66 | 218.2 | 565.61 | 2.59 | 364.51 | 678.97 | 1.86 | 2.04 |
| BC028439 | 66395 | 283.56 | 606.1 | 2.14 | 401.36 | 617.71 | 1.54 | 270.17 | 655.51 | 2.43 | 2.04 |
| AU019491 | 51944 | 338.52 | 699.66 | 2.07 | 269.43 | 534.46 | 1.98 | 309.96 | 637.11 | 2.06 | 2.04 |
| BC006736 | 75430 | 205.52 | 392.31 | 1.91 | 226.36 | 366.34 | 1.62 | 175.59 | 452.11 | 2.58 | 2.04 |
| BE952632 | 26378 | 215.19 | 422.63 | 1.96 | 140.13 | 294.26 | 2.1 | 179.78 | 368.52 | 2.05 | 2.04 |
| BB751158 | 17454 | 152.38 | 286.13 | 1.88 | 181.48 | 269.77 | 1.49 | 192.06 | 526.42 | 2.74 | 2.04 |
| BB782705 | 14679 | 116.44 | 380.3 | 3.27 | 224.41 | 391.87 | 1.75 | 197.19 | 215.7 | 1.09 | 2.04 |
| NM_009980 | 13017 | 154.06 | 318.08 | 2.06 | 79.52 | 176.79 | 2.23 | 187.47 | 340.63 | 1.82 | 2.04 |
| AF196480 | 23947 | 126.41 | 259.97 | 2.06 | 83.81 | 186.31 | 2.22 | 122.17 | 222.16 | 1.82 | 2.03 |
| BQ031123 | 66264 | 102.05 | 232.32 | 2.28 | 112.64 | 221.97 | 1.97 | 95.48 | 176.31 | 1.85 | 2.03 |
| BB770972 | 100047967 /// 237436 | 87.95 | 162.77 | 1.85 | 75.82 | 132.03 | 1.74 | 69.54 | 174.47 | 2.51 | 2.03 |
| BB114398 | 12816 | 85.23 | 147.26 | 1.73 | 64.54 | 166.23 | 2.58 | 75.77 | 135.04 | 1.78 | 2.03 |
| BB315555 | 18537 | 1525.52 | 2402.91 | 1.58 | 615.47 | 1821.05 | 2.96 | 1365.82 | 2119.74 | 1.55 | 2.03 |
| NM_024194 | 67144 | 319.91 | 663.11 | 2.07 | 281.38 | 456.04 | 1.62 | 271.37 | 650 | 2.4 | 2.03 |
| BB706079 | 20873 | 185.78 | 401.68 | 2.16 | 145.07 | 281.29 | 1.94 | 176.97 | 351.8 | 1.99 | 2.03 |
| AK006658 | 73327 | 146.58 | 352.15 | 2.4 | 157.48 | 265.95 | 1.69 | 151.13 | 301.73 | 2 | 2.03 |
| BC015270 | 97114 | 59.74 | 120.94 | 2.02 | 40.71 | 61.97 | 1.52 | 59.26 | 151.41 | 2.55 | 2.03 |
| NM_007830 | 13167 | 1090.59 | 1828.06 | 1.68 | 798.3 | 1502.71 | 1.88 | 861.53 | 2174.24 | 2.52 | 2.03 |
| BC019420 | 70544 | 575.76 | 1219.78 | 2.12 | 586.76 | 1169.57 | 1.99 | 527.67 | 1039.22 | 1.97 | 2.03 |
| BB039269 | 14609 | 144.89 | 264.86 | 1.83 | 85.6 | 182.53 | 2.13 | 103.11 | 218.96 | 2.12 | 2.03 |
| BB120594 | 30957 | 90.31 | 174.93 | 1.94 | 60.48 | 104.55 | 1.73 | 77.59 | 187.1 | 2.41 | 2.03 |
| AK016473 | 100037282 /// 66832 | 1409.46 | 2640.12 | 1.87 | 793.48 | 2060.87 | 2.6 | 1379.82 | 2212.52 | 1.6 | 2.02 |

TABLE 1-continued

| Accession | Entrez Gene | Control 1 | Anergic 1 | Upregulation 1 (fold) | Control 2 | Anergic 2 | Upregulation 2 (fold) | Control 3 | Anergic 3 | Upregulation 3 (fold) | Average Upregulation (fold) |
|---|---|---|---|---|---|---|---|---|---|---|---|
| NM_012010 | 100039419 /// 100048746 /// 26905 | 874.78 | 1524.28 | 1.74 | 652.74 | 1250.4 | 1.92 | 594.62 | 1430.83 | 2.41 | 2.02 |
| BG060677 | 223255 | 415.2 | 873.33 | 2.1 | 729.75 | 1318.27 | 1.81 | 356.3 | 767.84 | 2.16 | 2.02 |
| BB376573 | 68127 | 270.52 | 502.5 | 1.86 | 151.09 | 401.9 | 2.66 | 177.29 | 274.31 | 1.55 | 2.02 |
| NM_019670 | 56419 | 179.53 | 318.58 | 1.77 | 92.77 | 218.63 | 2.36 | 155.76 | 302.74 | 1.94 | 2.02 |
| AK005139 | 68262 | 756.51 | 925.39 | 1.22 | 396.96 | 749.3 | 1.89 | 579.83 | 1709.58 | 2.95 | 2.02 |
| Z25469 | 19128 | 347.58 | 694.16 | 2 | 170.15 | 501.31 | 2.95 | 337.85 | 374.69 | 1.11 | 2.02 |
| NM_016923 | 17087 | 359.9 | 621.34 | 1.73 | 140.36 | 436.16 | 3.11 | 329.85 | 403.68 | 1.22 | 2.02 |
| BB397062 | 69863 | 217.84 | 456.79 | 2.1 | 277.01 | 420.78 | 1.52 | 161.15 | 390.83 | 2.43 | 2.02 |
| BE630073 |  | 163.8 | 309.05 | 1.89 | 101.53 | 263.76 | 2.6 | 193.18 | 302.11 | 1.56 | 2.02 |
| AI426175 | 100900 | 626.1 | 1256.56 | 2.01 | 569.34 | 1239.36 | 2.18 | 573.67 | 1064.89 | 1.86 | 2.02 |
| BG067251 | 72085 | 147.01 | 281.62 | 1.92 | 71.23 | 110.09 | 1.55 | 138.45 | 357.5 | 2.58 | 2.02 |
| NM_013832 | 19415 | 113.33 | 271.27 | 2.39 | 102.42 | 225.54 | 2.2 | 116.54 | 169.65 | 1.46 | 2.02 |
| AK008567 | 67899 | 927.84 | 2002.88 | 2.16 | 1040.81 | 2496.92 | 2.4 | 1155.56 | 1711.06 | 1.48 | 2.01 |
| NM_025360 | 66111 | 1018.21 | 2009.44 | 1.97 | 770.14 | 2006.65 | 2.61 | 1368.97 | 2004.86 | 1.46 | 2.01 |
| BG063199 | 103080 | 202.82 | 365.1 | 1.8 | 164.91 | 244.77 | 1.48 | 154.9 | 426.81 | 2.76 | 2.01 |
| BC019957 | 67102 | 148.33 | 282.24 | 1.9 | 139.15 | 270.12 | 1.94 | 150.57 | 331.04 | 2.2 | 2.01 |
| BI143942 | 20322 | 330.53 | 768.54 | 2.33 | 296.29 | 528.36 | 1.78 | 432.9 | 833.21 | 1.92 | 2.01 |
| NM_026125 | 67389 | 429.31 | 771.39 | 1.8 | 522.64 | 997.74 | 1.91 | 485.65 | 1125.31 | 2.32 | 2.01 |
| BB172698 | 69367 | 583.96 | 1019.4 | 1.75 | 334.44 | 796.27 | 2.38 | 488.29 | 926.77 | 1.9 | 2.01 |
| AK005032 | 71779 | 145.08 | 314.45 | 2.17 | 134.29 | 262.74 | 1.96 | 155.49 | 295.59 | 1.9 | 2.01 |
| NM_133348 | 70025 | 4384.05 | 7588.24 | 1.73 | 2480.38 | 6749.69 | 2.72 | 4535.38 | 7109.42 | 1.57 | 2.01 |
| BB324206 | 218236 | 374.74 | 702.68 | 1.88 | 301.06 | 683.13 | 2.27 | 400.58 | 747.82 | 1.87 | 2.01 |
| BG071041 | 212377 | 232.05 | 498.76 | 2.15 | 656.87 | 1044.35 | 1.59 | 216.8 | 494.78 | 2.28 | 2.01 |
| BQ179335 | 24056 | 37.76 | 90.77 | 2.4 | 76.87 | 90.46 | 1.18 | 49.3 | 120.29 | 2.44 | 2.01 |
| BE200196 | 76273 | 2542.42 | 5294.28 | 2.08 | 2546.38 | 4782.64 | 1.88 | 2200.03 | 4520.38 | 2.05 | 2.00 |
| NM_008229 | 15182 | 633.88 | 1065.85 | 1.68 | 390.97 | 1141.26 | 2.92 | 879.36 | 1239.53 | 1.41 | 2.00 |
| NM_008206 | 15001 | 196.35 | 475.03 | 2.42 | 274.64 | 466.48 | 1.7 | 200.48 | 378.75 | 1.89 | 2.00 |
| NM_019686 | 56506 | 101.08 | 250.03 | 2.47 | 170.56 | 388.02 | 2.27 | 106.61 | 135.09 | 1.27 | 2.00 |
| AK020053 | 77875 | 94.12 | 118.61 | 1.26 | 94.44 | 130.59 | 1.38 | 97.26 | 327.71 | 3.37 | 2.00 |
| AV355474 |  | 97.17 | 126.6 | 1.3 | 102.46 | 167.2 | 1.63 | 70.57 | 217.16 | 3.08 | 2.00 |
| NM_008828 | 18655 /// 668435 | 6457.37 | 11634.83 | 1.8 | 5061.11 | 8114 | 1.6 | 5753.57 | 14971.56 | 2.6 | 2.00 |
| NM_030717 | 80907 | 608.06 | 1009.11 | 1.66 | 186.63 | 556.61 | 2.98 | 550.13 | 747.46 | 1.36 | 2.00 |
| BM876680 | 77048 | 324.56 | 735.36 | 2.27 | 275.94 | 583.24 | 2.11 | 363.74 | 588.38 | 1.62 | 2.00 |
| NM_016850 | 54123 | 279.37 | 335.24 | 1.2 | 129.76 | 383.74 | 2.96 | 261.54 | 481.08 | 1.84 | 2.00 |
| BC010318 | 74551 | 204.82 | 373.34 | 1.82 | 132.2 | 331.05 | 2.5 | 224.79 | 378.12 | 1.68 | 2.00 |

TABLE 2

| | Gene name | Description | Alternate names |
|---|---|---|---|
| 1 | Ccl1 | chemokine (C-C motif) ligand 1 | SCYA1, I-309, TCA3, P500, SISe |
| 2 | Crtam | cytotoxic and regulatory T cell molecule | CD355 |
| 3 | Egr2 | early growth response 2 | AT591; CMT1D; CMT4E; KROX20 |
| 4 | Rasgef1a | RasGEF domain family, member 1A | CG48531 2FLJ378171CG4853 gene product |
| 5 | Car12 | carbonic anhydrase XII | CA12carbonic anhydrase XIICAXIIHsT188161 carbonic anhydrase 12Carbonate dehydratase XII carbonic dehydrataseTumor antigen HOM-RCC-3.1.32 3 EC 4.2.1.13CA-XII2 3 |
| 6 | Fhl2 | four and a half LIM domains 2 | AAG11; DRAL; FHL-2; SLIM-3; SLIM3 |
| 7 | Pscd3 | cytohesin 3 | Cyth-3, cytohesin 31 2 ARF nucleotide-binding site opener 32 3ARNO31 2 3 5 PH, SEC7 and coiled-coil domain-containing protein 32 3GRP11 2 3 5 cytohesin-32PSCD31 2 3 5 Grp13pleckstrin homology, Sec7 and coiled-coil domains 31 2 Protein ARNO33General receptor of phosphoinositides 12 3 |

TABLE 2-continued

| Gene name | Description | Alternate names |
|---|---|---|
| 8 Pacsin1 | protein kinase C and casein kinase substrate in neurons 1 | protein kinase C and casein kinase substrate in neurons SDPIKIAA13793 protein kinase C and casein kinase substrate in neurons protein syndapin I |
| 9 Tnfrs9/4-1BB | tumor necrosis factor (ligand) superfamily, member 9 | CD137 |
| 10 Bcl2l11 | BCL2-like 11 (apoptosis facilitator) | BCL2-like 11 (apoptosis facilitator)BIM-beta7BIM1bcl-2 interacting mediator of cell deathBOD1bcl-2 interacting protein BimBimEL1 bcl-2-like protein 11BimL1 bcl-2-related ovarian death agonistBimS1 bcl2-L-11BAM2 B + C18cl2-L-113BIM-alpha6 Bcl2-interacting mediator of cell deathBIM-beta6 |
| 11 Gnb5 | guanine nucleotide binding protein (G protein), beta 5 | guanine nucleotide binding protein (G protein), beta 5gbeta5GB5guanine nucleotide-binding protein subunit beta-5Transducin beta chain 5guanine nucleotide-binding protein, beta subunit 5LG protein, beta subunit 5L Gbeta5G protein, beta-5 subunit |
| 12 Sdr39u1 | short chain dehydrogenase/reductase family 39U, member 1 | short chain dehydrogenase/reductase family 39U, member 1C14orf124HCDIShort-chain dehydrogenase/reductase family 39U memberchromosome 14 open reading frame 124epimerase family protein SDR39U |
| 13 Arc | activity-regulated cytoskeleton-associated protein | |
| 14 Tnfsfl1 | tumor necrosis factor (ligand) superfamily, member 11 | tumor necrosis factor (ligand) superfamily, member 11 + D19 Receptor activator of nuclear factor kappa-B ligandOPGLTNF-related activation-induced cytokine TRANCEOPTB22 ODF hRANKL2RANKLreceptor activator of nuclear factor kappa B ligandCD254sOdfOsteoclast differentiation factor tumor necrosis factor ligand superfamily memberOsteoprotegerin ligandCD254 antigen |
| 15 1190002H23Rik | regulator of cell cycle | regulator of cell cyclebA157L14.2RGC32Response gene to complement 32 proteinC13orf15chromosome 13 open reading frame 15RGC-32regulator of cell cycle RGCC |
| 16 Sema7a | semaphorin 7A, GPI membrane anchor (John Milton Hagen blood group) | |
| 17 Nrgn | neurogranin (protein kinase C substrate, RC3) | |
| 18 Gucy1a3 | guanylate cyclase 1, soluble, alpha 3 | |
| 19 Crabp2 | cellular retinoic acid binding protein 2 | |
| 20 Bach2 | BTB and CNC homology 1, basic leucine zipper transcription factor 2 | |

TABLE 2-continued

| | Gene name | Description | Alternate names |
|---|---|---|---|
| 21 | Nmi | N-myc (and STAT) interactor | N-myc (and STAT) interactorN-myc-interactorN-myc interactorNmiN-myc and STAT interactor |
| 22 | Pdk2 | pyruvate dehydrogenase kinase, isozyme 2 | |
| 23 | Dgkz | diacylglycerol kinase, zeta | |
| 24 | Mtss1 | metastasis suppressor 1 | |
| 25 | Cd74 | CD74 molecule, major histocompatibility complex, class II invariant chain | CD 74 molecule, major histocompatibility complex, class II invariant chain CD 74 antigen (invariant polypeptide of major histocompatibility complex, class II |
| 26 | Ptgfm | | |
| 27 | Klf9 | kinesin family member 9 | |
| 28 | Rai14 | retinoic acid induced 14 | |
| 29 | Lag3 | lymphocyte-activation gene 3 | |
| 30 | Slc17a6 | solute carrier family 17 (sodium-dependent inorganic phosphate cotransporter), member 6 | |
| 31 | Trpm4 | transient receptor potential cation channel, subfamily M, member 4 | |
| 32 | E130308A19Rik | uncharacterized protein KIAA1958 | KIAA1958 |
| 33 | Ryr1 | ryanodine receptor 1 (skeletal) | |
| 34 | A2bp1 | RNA binding protein, fox-1 homolog (*C. elegans*) 1 | |
| 35 | Pros1 | protein S (alpha) | protein S (alpha) |
| 36 | Ece1 | endothelin converting enzyme 1 | |
| 37 | Olr1 | oxidized low density lipoprotein (lectin-like) receptor 1 | |
| 38 | Stk32c | serine/threonine kinase 32C | |
| 39 | Exph5 | exophilin 5 | exophilin 5KIAA0624SLAC2Bexophilin-5SLAC2-Bsynaptotagmin-like homologue lacking C2 domains bSlp homolog lacking C2 domains bSlaC2-bSynaptotagmin-like protein homolog lacking C2 domains b |
| 40 | Jazf1 | JAZF zinc finger 1 | |
| 41 | Nelf | nasal embryonic LHRH factor | |
| 42 | Ddx11 | DEAD/H (Asp-Glu-Ala-Asp/His) box helicase 11 | probable ATP-dependent RNA helicase DDX11 |
| 43 | Repin1 | replication initiator 1 | |
| 44 | Cib2 | calcium and integrin binding family member 2 | |
| 45 | Tspan5 | tetraspanin 5 | |
| 46 | Cish | cytokine inducible SH2-containing protein | |
| 47 | Ttc3 | tetratricopeptide repeat domain 3 | DCRR1 RNF105 TPRD TPRDIII Tetratricopeptide repeat protein 3 RING finger protein 1052 TPR repeat protein D TPRDI TPRDII tetratricopeptide repeat protein 3 (TPR repeat protein D)11 E3 ubiquitin-protein ligase TTC3 EC 6.3.2.- Protein DCRR1 |
| 48 | Arl3 | ADP-ribosylation factor-like 3 | |
| 49 | Fam195a | family with sequence similarity 195, member A | |
| 50 | Slc13a3 | solute carrier family 13 (sodium-dependent dicarboxylate transporter), member 3 | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bailey T. et al., *Nucleic Acids Res.* 37:W202-8, 2009.
Baixeras E., et al., *J Exp Med.* 176(2):327-37, 1992.
Bernardini G., et al., *Blood.* 96(13):4039-45, 2000.
Bouillet P. and O'Reilly L. A. *Nat Rev Immunol.* 9:514-519, 2009.
Chai J. G., et al., *Eur J Immunol.* 29(2):686-92, 1999.
Chavrier P., et al., *EMBO J.* 7(1):29-35, 1988.
Chuaqui R. F., et al., *Nat Genet.* 32 Suppl: 509-14, 2002.
Curran M. A., et al., *PLoS ONE.* 6(4):e19499, 2011.
Czopik A. K., et al., *Immunity.* 24(5):591-600, 2006.
Diez-Guerra F. J. *IUBMB Life.* 62(8):597-606, 2010.
Draghici S., et al., *TRENDS in Genetics.* 22(2):101-109, 2006.
Du Pasquier L. *C R Biol.* 327(6):591-601, 2004.
Fitch F. W., et al., *Curr Protoc Immunol.* Chapter 3, Unit 3 13, 2006.
Gajewski T. F. and Fitch F. W. *J Immunol.* 144(2):548-56, 1990.
Gajewski T. F., et al., *Curr Opin Immunol.* 23(2):286-92, 2011.
Gandhi M. K., et al., *Blood.* 108(7):2280-9, 2006.
Grosso J. F., et al., *J Clin Invest.* 117(11):3383-92, 2007.
Hall J. A., et al., *Immunity.* 35(1):13-22, 2011.
Harris J. E., et al., *J Immunol.* 173(12):7331-8, 2004.
Hoelzinger D. B., et al., *J Immunol.* 184(12):6833-42, 2010.
Huang C. T., et al., *Immunity.* 21(4):502-13, 2004.
Naeve G. S., et al., *Proc Natl Acad Sci USA.* 94(6):2648-53, 1997.
Nedivi E., et al., *Proc Natl Acad Sci USA.* 93(5):2048-53, 1996.
Nedivi E., et al., *Science.* 281(5384):1863-6, 1998.
Olenchock B. A., et al., *Nat Immunol.* 7(11):1174-81, 2006.
Patwardhan S., et al., *Oncogene.* 6(6):917-28, 1991.
Safford M., et al., *Nat Immunol.* 6(5):472-80, 2005.
Schwartz R. H. *Annu Rev Immunol.* 21:305-34, 2003.
Soler D., et al., *J Immunol.* 177(10):6940-51, 2006.
Suzuki K., et al., *Nat Immunol.* 9(1):17-23, 2008.
Suzuki K., et al. *Nature.* 446(7136):680-4, 2007.
Takeuchi A., et al., *J Immunol.* 183(7):4220-8, 2009.
Triebel F., et al., *J Exp Med.* 171(5):1393-405, 1990.
Valouev A., et al., *Nat Methods.* 5(9):829-34, 2008.
Wan Y. Y., et al., *Proc Natl Aca Sci USA.* 97(25): 13784-9, 2000.
Wang C., et al., *Immunological Rev.* 229:192-215, 2009.
Wang Z., et al., *Nat Rev Genet.* 10(1):57-63, 2009.
Watts T. H. *Annu Rev Immunol.* 23:23-68, 2005.
Woo S. R., et al., *Cancer Res.* 72:917-27, 2012.
Yeh J. H., et al., *Cell.* 132(5):846-59, 2008.
Zha Y., et al., *Nat Immunol.* 7(11):1166-73, 2006.
Zha Y., et al., *J Immunol Methods.* 311(1-2):94-102, 2008.
Zheng Y., et al., *J Exp Med.* 209(12):2157-63, 2012.
Zheng Y., et al., *EMBO Rep.* 9(1):50-5, 2008.

The invention claimed is:

1. A method for treating a patient with immunotherapy comprising administering said immunotherapy to the patient after the patient is identified as having non-anergic T-cells, wherein
A) the patient is identified as having non-anergic T-cells by measuring decreased expression levels of T-cell anergic genes comprising Semaphorin 7A (Sema7A), Class-I-MHC-restricted T cell associated molecule (CRTAM), lymphocyte-activation gene 3 (Lag3), 4-1BB and neuritin (Nrn1) compared to reference or control expression levels in anergic T-cells,
or wherein
B) the patient is identified as having non-anergic T-cells by measuring expression levels of T-cell anergic genes comprising Semaphorin 7A (Sema7A), Class-I-MHC-restricted T cell associated molecule (CRTAM), lymphocyte-activation gene 3 (Lag3), 4-1BB and Nrn1 and comparing the expression levels to reference or control expression levels in anergic T-cells.

2. The method of claim 1, wherein the patient is a cancer patient.

3. The method of claim 1, wherein the immunotherapy comprises a cell-based immunotherapy.

4. The method of claim 1, wherein the immunotherapy comprises antibody therapy.

5. The method of claim 1, wherein the immunotherapy comprises a cancer vaccine.

6. The method of claim 1, wherein the patient is identified as having non-anergic T-cells by further comparing the expression levels to control or reference expression levels in non-anergic T-cells.

7. The method of claim 1, wherein the levels of expression are measured using probes or primers specific for Sema7A, CRTAM, Lag3, 4-1BB, and Nrn1.

8. The method of claim 1, further comprising measuring the expression levels of at least two more genes selected from the group consisting of Ccl1, Egr2, Rasgef1a, Car12, Fhl2, Pscd3, Pacsin1, Bcl2l11, Gnb5, Sdr39u1, Arc, Tnfsf11, 1190002H23Rik, Nrgn, Gucy1a3, Crabp2, Bach2, Nm1, Pdk2, Dgkz, Mtss1, Cd74, Ptgfm, Klf9, Rai14, Slc17a6, Trpm4, E130308A19Rik, Ryr1, A2bp1, Pros1, Ece1, Olr1, Stk32c, Exph5, Jazf1, Nelf, Ddx11, Repin1, Cib2, Tspan5, Cish, Ttc3, Arl3, Fam195a, and Slc13a3.

9. The method of claim 1, wherein the immunotherapy comprises a cell-based immunotherapy, antibody therapy, or a cancer vaccine.

\* \* \* \* \*

UNITED STATES PATENT AND TRADEMARK OFFICE
CERTIFICATE OF CORRECTION

PATENT NO. : 11,802,316 B2
APPLICATION NO. : 16/948455
DATED : October 31, 2023
INVENTOR(S) : Yan Zheng et al.

Page 1 of 1

It is certified that error appears in the above-identified patent and that said Letters Patent is hereby corrected as shown below:

In the Specification

In Column 1, Line 20, please delete "The invention was made with government support under Grant Nos. R01 CA161005, R01 AI080745, and R21 AI79373 awarded by the National Institutes of Health. The government has certain rights in the invention." and insert --This invention was made with government support under R01 CA161005, R21 AI079373, and R01 AI080745 awarded by the National Institutes of Health. The government has certain rights in the invention.-- therefor.

Signed and Sealed this
Sixteenth Day of April, 2024

Katherine Kelly Vidal
*Director of the United States Patent and Trademark Office*

SEQUENCE LISTING

<160> NUMBER OF SEQ ID NOS: 114

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1
aatggccaca tggaaaactc                                               20

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
ccaaacatac ctcgaatacg c                                             21

<210> SEQ ID NO 3
<211> LENGTH: 19
<212> TYPE: DNA
<213> ORGANISM: Artificial Sequence

```
<220> FEATURE:
<223> OTHER INFORMATION: Synthetic Primer

<400> SEQUENCE: 3
tctggacagg aggggatgt                                                19

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
aggaaacacc cacagcaaag                                               20

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
gcttctgctg gtgttctgg                                                19

<210> SEQ ID NO 6
<211> LENGTH: 18
<212> TYPE: DNA
<213> ORGANISM: Artificial Sequence
<220> FEATURE:
<223> OTHER INFORMATION: Synthetic Primer

<400> SEQUENCE: 6
cgcctacctt tccagacg                                                 18

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ctccagaccc agtccttctg                                               20

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
acactttcca ctgcgaagc                                                19

<210> SEQ ID NO 9
<211> LENGTH: 25
<212> TYPE: DNA
<213> ORGANISM: Artificial Sequence
<220> FEATURE:
<223> OTHER INFORMATION: Synthetic Primer

<400> SEQUENCE: 9
aatctcttaa ctcaggagag acgtg                                         25
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
ttcccaccac agtgacattc                                                 20

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer

<400> SEQUENCE: 11
ggcttggctc agatcagg                                                   18

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gggaaagaat ggtgctgaaa                                                 20

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
gtgactgatt ttcatcccag tg                                              22

<210> SEQ ID NO 14
<211> LENGTH: 18
<212> TYPE: DNA
<213> ORGANISM: Artificial Sequence
<220> FEATURE:
<223> OTHER INFORMATION: Synthetic Primer

<400> SEQUENCE: 14
accaggactc cccgtctc                                                   18

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
tccacttgga ttcacaccac                                                 20

<210> SEQ ID NO 16
<211> LENGTH: 19
<212> TYPE: DNA
<213> ORGANISM: Artificial Sequence
<220> FEATURE:
<223> OTHER INFORMATION: Synthetic Primer
```

```
<400> SEQUENCE: 16
cagacattgg gtggacgag                                             19

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
cttgccttct gacgcttctc                                            20

<210> SEQ ID NO 18
<211> LENGTH: 19
<212> TYPE: DNA
<213> ORGANISM: Artificial Sequence
<220> FEATURE:
<223> OTHER INFORMATION: Synthetic Primer

<400> SEQUENCE: 18
gggttctcca agagccaag                                             19

<210> SEQ ID NO 19
<211> LENGTH: 19
<212> TYPE: DNA
<213> ORGANISM: Artificial Sequence
<220> FEATURE:
<223> OTHER INFORMATION: Synthetic Primer

<400> SEQUENCE: 19
accatggagg tggccttca                                             19

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
catgcagggt atccaggaag a                                          21

<210> SEQ ID NO 21
<211> LENGTH: 19
<212> TYPE: DNA
<213> ORGANISM: Artificial Sequence
<220> FEATURE:
<223> OTHER INFORMATION: Synthetic Primer

<400> SEQUENCE: 21
tcaccatgaa acccactgc                                             19

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
agcagcagct attggagacc                                            20

<210> SEQ ID NO 23
```

```
<211> LENGTH: 8
<212> TYPE: DNA
<213> ORGANISM: Artificial Sequence
<220> FEATURE:
<223> OTHER INFORMATION: Synthetic Primer

<400> SEQUENCE: 23 ctggctgc                                                              8

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
agatccaaca acgaggagac a                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
tcatgcaacg cttagactgg                                                20

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
tcaatcggct gcaagatgt                                                 19

<210> SEQ ID NO 27
<211> LENGTH: 21
<212> TYPE: DNA
<213> ORGANISM: Artificial Sequence
<220> FEATURE:
<223> OTHER INFORMATION: Synthetic Primer

<400> SEQUENCE: 27
cgcagacagc tgagtagttc c                                              21

<210> SEQ ID NO 28
<211> LENGTH: 8
<212> TYPE: DNA
<213> ORGANISM: Artificial Sequence
<220> FEATURE:
<223> OTHER INFORMATION: Synthetic Primer

<400> SEQUENCE: 28 gagcagga                                                              8

<210> SEQ ID NO 29
<211> LENGTH: 19
<212> TYPE: DNA
<213> ORGANISM: Artificial Sequence
<220> FEATURE:
<223> OTHER INFORMATION: Synthetic Primer

<400> SEQUENCE: 29
```
tgctttggga agctccagt                                                    19

<210> SEQ ID NO 30
<211> LENGTH: 18
<212> TYPE: DNA
<213> ORGANISM: Artificial Sequence
<220> FEATURE:
<223> OTHER INFORMATION: Synthetic Primer

<400> SEQUENCE: 30
gctgcaggga agatggac                                                     18

<210> SEQ ID NO 31
<211> LENGTH: 8
<212> TYPE: DNA
<213> ORGANISM: Artificial Sequence
<220> FEATURE:
<223> OTHER INFORMATION: Synthetic Primer

<400> SEQUENCE: 31 ccaggagg                                                                8

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
gaacggtact ggcgtctgtc                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
ccggtcttaa gcacagacct                                                   20

<210> SEQ ID NO 34
<211> LENGTH: 8
<212> TYPE: DNA
<213> ORGANISM: Artificial Sequence
<220> FEATURE:
<223> OTHER INFORMATION: Synthetic Primer

<400> SEQUENCE: 34 ctgctctc                                                                8

<210> SEQ ID NO 35
<211> LENGTH: 18
<212> TYPE: DNA
<213> ORGANISM: Artificial Sequence
<220> FEATURE:
<223> OTHER INFORMATION: Synthetic Primer

<400> SEQUENCE: 35
aacaccggca atggactg                                                     18

<210> SEQ ID NO 36
<211> LENGTH: 19
<212> TYPE: DNA

```
<213> ORGANISM: Artificial Sequence
<220> FEATURE:
<223> OTHER INFORMATION: Synthetic Primer

<400> SEQUENCE: 36
aaactcgcct ggattttgg                                           19

<210> SEQ ID NO 37
<211> LENGTH: 8
<212> TYPE: DNA
<213> ORGANISM: Artificial Sequence
<220> FEATURE:
<223> OTHER INFORMATION: Synthetic Primer

<400> SEQUENCE: 37 gctggatg                                                       8

<210> SEQ ID NO 38
<211> LENGTH: 18
<212> TYPE: DNA
<213> ORGANISM: Artificial Sequence
<220> FEATURE:
<223> OTHER INFORMATION: Synthetic Primer

<400> SEQUENCE: 38
tcctcgcggt gcaaatag                                            18

<210> SEQ ID NO 39
<211> LENGTH: 21
<212> TYPE: DNA
<213> ORGANISM: Artificial Sequence
<220> FEATURE:
<223> OTHER INFORMATION: Synthetic Primer

<400> SEQUENCE: 39
gcccttaaag actgcatcac a                                        21

<210> SEQ ID NO 40
<211> LENGTH: 22
<212> TYPE: DNA
<213> ORGANISM: Artificial Sequence
<220> FEATURE:
<223> OTHER INFORMATION: Synthetic Primer

<400> SEQUENCE: 40
ggagacgagt tcaacgaaac tt                                       22

<210> SEQ ID NO 41
<211> LENGTH: 26
<212> TYPE: DNA
<213> ORGANISM: Artificial Sequence
<220> FEATURE:
<223> OTHER INFORMATION: Synthetic Primer

<400> SEQUENCE: 41
aacagttgta agataaccat ttgagg                                   26

<210> SEQ ID NO 42
<211> LENGTH: 8
<212> TYPE: DNA
<213> ORGANISM: Artificial Sequence
<220> FEATURE:
<223> OTHER INFORMATION: Synthetic Primer

<400> SEQUENCE: 42 ggctgaag                                                       8
```

<210> SEQ ID NO 43
<211> LENGTH: 19
<212> TYPE: DNA
<213> ORGANISM: Artificial Sequence
<220> FEATURE:
<223> OTHER INFORMATION: Synthetic Primer

<400> SEQUENCE: 43
aaatggtgtg cgagcagag                                                  19

<210> SEQ ID NO 44
<211> LENGTH: 22
<212> TYPE: DNA
<213> ORGANISM: Artificial Sequence
<220> FEATURE:
<223> OTHER INFORMATION: Synthetic Primer

<400> SEQUENCE: 44
aacgtcatct gctgtcattg tc                                              22

<210> SEQ ID NO 45
<211> LENGTH: 5
<212> TYPE: PRT
<213> ORGANISM: Artificial sequence
<220> FEATURE:
<223> OTHER INFORMATION: Synthetic sequence

<400> SEQUENCE: 45

Asp Tyr Tyr Trp Asn
1               5

<210> SEQ ID NO 46
<211> LENGTH: 5
<212> TYPE: PRT
<213> ORGANISM: Artificial sequence
<220> FEATURE:
<223> OTHER INFORMATION: Synthetic sequence

<400> SEQUENCE: 46

Ser Tyr Gly Met His
1               5

<210> SEQ ID NO 47
<211> LENGTH: 5
<212> TYPE: PRT
<213> ORGANISM: Artificial sequence
<220> FEATURE:
<223> OTHER INFORMATION: Synthetic sequence

<400> SEQUENCE: 47

Asp Tyr Gly Met Ser
1               5

<210> SEQ ID NO 48
<211> LENGTH: 5
<212> TYPE: PRT
<213> ORGANISM: Artificial sequence
<220> FEATURE:
<223> OTHER INFORMATION: Synthetic sequence

<400> SEQUENCE: 48

Gly Tyr Tyr Trp Ser
1               5

<210> SEQ ID NO 49

```
<211> LENGTH: 5
<212> TYPE: PRT
<213> ORGANISM: Artificial sequence
<220> FEATURE:
<223> OTHER INFORMATION: Synthetic sequence

<400> SEQUENCE: 49

Glu Val Ser Met His
1               5

<210> SEQ ID NO 50
<211> LENGTH: 5
<212> TYPE: PRT
<213> ORGANISM: Artificial sequence
<220> FEATURE:
<223> OTHER INFORMATION: Synthetic sequence

<400> SEQUENCE: 50

Ser Tyr Gly Met His
1               5

<210> SEQ ID NO 51
<211> LENGTH: 16
<212> TYPE: PRT
<213> ORGANISM: Artificial sequence
<220> FEATURE:
<223> OTHER INFORMATION: Synthetic sequence

<400> SEQUENCE: 51

Glu Ile Asn His Asn Gly Asn Thr Asn Ser Asn Pro Ser Leu Lys Ser
1               5                   10                  15

<210> SEQ ID NO 52
<211> LENGTH: 17
<212> TYPE: PRT
<213> ORGANISM: Artificial sequence
<220> FEATURE:
<223> OTHER INFORMATION: Synthetic sequence

<400> SEQUENCE: 52

Val Ile Trp Tyr Asp Gly Ser Asn Lys Tyr Tyr Ala Asp Ser Val Lys
1               5                   10                  15

Gly

<210> SEQ ID NO 53
<211> LENGTH: 17
<212> TYPE: PRT
<213> ORGANISM: Artificial sequence
<220> FEATURE:
<223> OTHER INFORMATION: Synthetic sequence

<400> SEQUENCE: 53

Gly Ile Asn Trp Asn Gly Gly Ser Thr Tyr Tyr Ala Asp Ser Val Lys
1               5                   10                  15

Gly

<210> SEQ ID NO 54
<211> LENGTH: 16
<212> TYPE: PRT
<213> ORGANISM: Artificial sequence
<220> FEATURE:
<223> OTHER INFORMATION: Synthetic sequence

<400> SEQUENCE: 54

Glu Ile Asn His Arg Gly Asn Thr Asn Cys Asn Pro Ser Leu Lys Ser
1               5                   10                  15
```

<210> SEQ ID NO 55
<211> LENGTH: 17
<212> TYPE: PRT
<213> ORGANISM: Artificial sequence
<220> FEATURE:
<223> OTHER INFORMATION: Synthetic sequence

<400> SEQUENCE: 55

Gly Phe Asp Pro Glu Asp Gly Glu Thr Ile Tyr Ala Gln Lys Phe Gln
1               5                   10                  15

Gly

<210> SEQ ID NO 56
<211> LENGTH: 17
<212> TYPE: PRT
<213> ORGANISM: Artificial sequence
<220> FEATURE:
<223> OTHER INFORMATION: Synthetic sequence

<400> SEQUENCE: 56

Val Ile Trp Tyr Asp Gly Ser Asn Lys Tyr Tyr Ala Asp Ser Val Lys
1               5                   10                  15

Gly

<210> SEQ ID NO 57
<211> LENGTH: 12
<212> TYPE: PRT
<213> ORGANISM: Artificial sequence
<220> FEATURE:
<223> OTHER INFORMATION: Synthetic sequence

<400> SEQUENCE: 57

Gly Tyr Ser Asp Tyr Glu Tyr Asn Trp Phe Asp Pro
1               5                   10

<210> SEQ ID NO 58
<211> LENGTH: 13
<212> TYPE: PRT
<213> ORGANISM: Artificial sequence
<220> FEATURE:
<223> OTHER INFORMATION: Synthetic sequence

<400> SEQUENCE: 58

Glu Trp Ala Val Ala Ser Trp Asp Tyr Gly Met Asp Val
1               5                   10

<210> SEQ ID NO 59
<211> LENGTH: 5
<212> TYPE: PRT
<213> ORGANISM: Artificial sequence
<220> FEATURE:
<223> OTHER INFORMATION: Synthetic sequence

<400> SEQUENCE: 59

Pro Val Gly Val Val
1               5

<210> SEQ ID NO 60
<211> LENGTH: 12
<212> TYPE: PRT
<213> ORGANISM: Artificial sequence
<220> FEATURE:
<223> OTHER INFORMATION: Synthetic sequence

<400> SEQUENCE: 60

```
Gly Tyr Asp Ile Leu Thr Gly Tyr Tyr Glu Asp Ser
1               5                   10
```

<210> SEQ ID NO 61
<211> LENGTH: 11
<212> TYPE: PRT
<213> ORGANISM: Artificial sequence
<220> FEATURE:
<223> OTHER INFORMATION: Synthetic sequence

<400> SEQUENCE: 61

```
Ala Phe Val Val Val Ala Ala Ser Asp Tyr
1               5                   10
```

<210> SEQ ID NO 62
<211> LENGTH: 14
<212> TYPE: PRT
<213> ORGANISM: Artificial sequence
<220> FEATURE:
<223> OTHER INFORMATION: Synthetic sequence

<400> SEQUENCE: 62

```
Asp Pro His Cys Ser Ser Thr Asn Cys Tyr Leu Phe Asp Tyr
1               5                   10
```

<210> SEQ ID NO 63
<211> LENGTH: 11
<212> TYPE: PRT
<213> ORGANISM: Artificial sequence
<220> FEATURE:
<223> OTHER INFORMATION: Synthetic sequence

<400> SEQUENCE: 63

```
Arg Ala Ser Gln Ser Ile Ser Ser Tyr Leu Ala
1               5                   10
```

<210> SEQ ID NO 64
<211> LENGTH: 12
<212> TYPE: PRT
<213> ORGANISM: Artificial sequence
<220> FEATURE:
<223> OTHER INFORMATION: Synthetic sequence

<400> SEQUENCE: 64

```
Arg Ala Ser Gln Ser Val Ser Ser Ser Tyr Leu Ala
1               5                   10
```

<210> SEQ ID NO 65
<211> LENGTH: 11
<212> TYPE: PRT
<213> ORGANISM: Artificial sequence
<220> FEATURE:
<223> OTHER INFORMATION: Synthetic sequence

<400> SEQUENCE: 65

```
Arg Ala Ser Gln Gly Ile Arg Ser Ala Leu Ala
1               5                   10
```

<210> SEQ ID NO 66
<211> LENGTH: 11
<212> TYPE: PRT
<213> ORGANISM: Artificial sequence
<220> FEATURE:
<223> OTHER INFORMATION: Synthetic sequence

<400> SEQUENCE: 66

Arg Ala Ser Gln Ser Val Ser Ser Tyr Leu Ala
1               5                   10

<210> SEQ ID NO 67
<211> LENGTH: 11
<212> TYPE: PRT
<213> ORGANISM: Artificial sequence
<220> FEATURE:
<223> OTHER INFORMATION: Synthetic sequence

<400> SEQUENCE: 67

Arg Ala Ser Gln Ser Val Ser Ser Tyr Leu Ala
1               5                   10

<210> SEQ ID NO 68
<211> LENGTH: 11
<212> TYPE: PRT
<213> ORGANISM: Artificial sequence
<220> FEATURE:
<223> OTHER INFORMATION: Synthetic sequence

<400> SEQUENCE: 68

Arg Ala Ser Gln Ser Val Ser Ser Tyr Leu Ala
1               5                   10

<210> SEQ ID NO 69
<211> LENGTH: 7
<212> TYPE: PRT
<213> ORGANISM: Artificial sequence
<220> FEATURE:
<223> OTHER INFORMATION: Synthetic sequence

<400> SEQUENCE: 69

Asp Ala Ser Asn Arg Ala Thr
1               5

<210> SEQ ID NO 70
<211> LENGTH: 7
<212> TYPE: PRT
<213> ORGANISM: Artificial sequence
<220> FEATURE:
<223> OTHER INFORMATION: Synthetic sequence

<400> SEQUENCE: 70

Gly Ala Ser Ser Arg Ala Thr
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic sequence

<400> SEQUENCE: 71

Asp Ala Ser Ser Leu Glu Ser
1               5

<210> SEQ ID NO 72
<211> LENGTH: 7
<212> TYPE: PRT
<213> ORGANISM: Artificial sequence
<220> FEATURE:
<223> OTHER INFORMATION: Synthetic sequence

<400> SEQUENCE: 72

Asn Ala Ser Asn Arg Ala Thr

```
1               5

<210> SEQ ID NO 73
<211> LENGTH: 7
<212> TYPE: PRT
<213> ORGANISM: Artificial sequence
<220> FEATURE:
<223> OTHER INFORMATION: Synthetic sequence

<400> SEQUENCE: 73

Asp Ala Ser Asn Arg Ala Thr
1               5

<210> SEQ ID NO 74
<211> LENGTH: 7
<212> TYPE: PRT
<213> ORGANISM: Artificial sequence
<220> FEATURE:
<223> OTHER INFORMATION: Synthetic sequence

<400> SEQUENCE: 74

Asp Ala Ser Asn Arg Ala Thr
1               5

<210> SEQ ID NO 75
<211> LENGTH: 9
<212> TYPE: PRT
<213> ORGANISM: Artificial sequence
<220> FEATURE:
<223> OTHER INFORMATION: Synthetic sequence

<400> SEQUENCE: 75

Gln Gln Arg Ser Asn Trp Pro Leu Thr
1               5

<210> SEQ ID NO 76
<211> LENGTH: 9
<212> TYPE: PRT
<213> ORGANISM: Artificial sequence
<220> FEATURE:
<223> OTHER INFORMATION: Synthetic sequence

<400> SEQUENCE: 76

Gln Gln Tyr Gly Ser Ser Pro Phe Thr
1               5

<210> SEQ ID NO 77
<211> LENGTH: 9
<212> TYPE: PRT
<213> ORGANISM: Artificial sequence
<220> FEATURE:
<223> OTHER INFORMATION: Synthetic sequence

<400> SEQUENCE: 77

Gln Gln Phe Asn Ser Tyr Pro Tyr Thr
1               5

<210> SEQ ID NO 78
<211> LENGTH: 9
<212> TYPE: PRT
<213> ORGANISM: Artificial sequence
<220> FEATURE:
<223> OTHER INFORMATION: Synthetic sequence

<400> SEQUENCE: 78

Gln Gln Arg Ser Asn Trp Pro Leu Thr
1               5
```

```
<210> SEQ ID NO 79
<211> LENGTH: 9
<212> TYPE: PRT
<213> ORGANISM: Artificial sequence
<220> FEATURE:
<223> OTHER INFORMATION: Synthetic sequence

<400> SEQUENCE: 79

Gln Gln Arg Ser Asn Trp Pro Trp Thr
1               5

<210> SEQ ID NO 80
<211> LENGTH: 9
<212> TYPE: PRT
<213> ORGANISM: Artificial sequence
<220> FEATURE:
<223> OTHER INFORMATION: Synthetic sequence

<400> SEQUENCE: 80

Gln Gln Arg Ser Asn Trp Pro Ile Thr
1               5

<210> SEQ ID NO 81
<211> LENGTH: 120
<212> TYPE: PRT
<213> ORGANISM: Artificial sequence
<220> FEATURE:
<223> OTHER INFORMATION: Synthetic sequence

<400> SEQUENCE: 81

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 82
<211> LENGTH: 122
<212> TYPE: PRT
<213> ORGANISM: Artificial sequence
<220> FEATURE:
<223> OTHER INFORMATION: Synthetic sequence

<400> SEQUENCE: 82

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Ala Val Ala Ser Trp Asp Tyr Gly Met Asp Val Trp
            100                 105                 110

Gly Gln Gly Thr Thr Val Thr Val Ser Ser
            115                 120

<210> SEQ ID NO 83
<211> LENGTH: 112
<212> TYPE: PRT
<213> ORGANISM: Artificial sequence
<220> FEATURE:
<223> OTHER INFORMATION: Synthetic sequence

<400> SEQUENCE: 83

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
         35                  40                  45

Ser Gly Ile Asn Trp Asn Gly Gly Ser Thr Tyr Tyr Ala Asp Ser Val
     50                  55                  60

Lys Gly Arg Phe Thr Ile Ser Gly Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Thr Thr Gly Gly Tyr Trp Gly Gln Gly Thr Leu Val Thr Val Ser Ser
            100                 105                 110

<210> SEQ ID NO 84
<211> LENGTH: 120
<212> TYPE: PRT
<213> ORGANISM: Artificial sequence
<220> FEATURE:
<223> OTHER INFORMATION: Synthetic sequence

<400> SEQUENCE: 84

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Arg Gly Asn Thr Asn Cys Asn Pro Ser Leu Lys
     50                  55                  60

Ser Arg Val Thr Ile Ser Gly Asp Thr Ser Lys Lys Gln Phe Ala Leu
 65                  70                  75                  80

Lys Leu Asn Ser Val Thr Ala Ala Asp Thr Ala Val Tyr Tyr Cys Ala
                 85                  90                  95

Arg Gly Tyr Asp Ile Leu Thr Gly Tyr Tyr Glu Asp Ser Trp Gly Pro
            100                 105                 110

Gly Thr Leu Val Thr Val Ser Ser
```

115                 120

<210> SEQ ID NO 85
<211> LENGTH: 123
<212> TYPE: PRT
<213> ORGANISM: Artificial sequence
<220> FEATURE:
<223> OTHER INFORMATION: Synthetic sequence

<400> SEQUENCE: 85

Thr His Asp Gln Val Gln Leu Val Gln Ser Gly Ala Glu Val Lys Lys
1               5                   10                  15

Pro Gly Ala Ser Val Lys Val Ser Cys Lys Val Ser Gly Tyr Thr Leu
            20                  25                  30

Thr Glu Val Ser Met His Trp Val Arg Gln Ala Pro Gly Lys Gly Leu
        35                  40                  45

Glu Trp Met Gly Gly Phe Asp Pro Glu Asp Gly Glu Thr Ile Tyr Ala
    50                  55                  60

Gln Lys Phe Gln Gly Arg Val Thr Met Thr Glu Asp Thr Ser Thr Asp
65                  70                  75                  80

Thr Ala Tyr Met Glu Leu Ser Ser Leu Arg Ser Glu Asp Thr Ala Val
                85                  90                  95

Tyr Tyr Cys Ala Thr Ala Phe Val Val Val Ala Ala Ser Asp Tyr
            100                 105                 110

Trp Gly Gln Gly Thr Leu Val Thr Val Ser Ser
            115                 120

<210> SEQ ID NO 86
<211> LENGTH: 123
<212> TYPE: PRT
<213> ORGANISM: Artificial sequence
<220> FEATURE:
<223> OTHER INFORMATION: Synthetic sequence

<400> SEQUENCE: 86

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro His Cys Ser Ser Thr Asn Cys Tyr Leu Phe Asp Tyr
            100                 105                 110

Trp Gly Gln Gly Thr Leu Val Thr Val Ser Ser
            115                 120

<210> SEQ ID NO 87
<211> LENGTH: 107
<212> TYPE: PRT
<213> ORGANISM: Artificial sequence
<220> FEATURE:
<223> OTHER INFORMATION: Synthetic sequence

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 88
<211> LENGTH: 108
<212> TYPE: PRT
<213> ORGANISM: Artificial sequence
<220> FEATURE:
<223> OTHER INFORMATION: Synthetic sequence

<400> SEQUENCE: 88

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 89
<211> LENGTH: 107
<212> TYPE: PRT
<213> ORGANISM: Artificial sequence
<220> FEATURE:
<223> OTHER INFORMATION: Synthetic sequence

<400> SEQUENCE: 89

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr 85                  90                  95

Thr Phe Gly Gln Gly Thr Lys Leu Glu Ile Lys
                100                 105

<210> SEQ ID NO 90
<211> LENGTH: 107
<212> TYPE: PRT
<213> ORGANISM: Artificial sequence
<220> FEATURE:
<223> OTHER INFORMATION: Synthetic sequence

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
                100                 105

<210> SEQ ID NO 91
<211> LENGTH: 107
<212> TYPE: PRT
<213> ORGANISM: Artificial sequence
<220> FEATURE:
<223> OTHER INFORMATION: Synthetic sequence

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
                100                 105

<210> SEQ ID NO 92
<211> LENGTH: 107
<212> TYPE: PRT
<213> ORGANISM: Artificial sequence
<220> FEATURE:
<223> OTHER INFORMATION: Synthetic sequence

<400> SEQUENCE: 92

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                   70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105
```

<210> SEQ ID NO 93
<211> LENGTH: 467
<212> TYPE: PRT
<213> ORGANISM: Artificial sequence
<220> FEATURE:
<223> OTHER INFORMATION: Synthetic sequence

<400> SEQUENCE: 93

```
Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
         35                  40                  45

Ser Gly Tyr Tyr Trp Ser Trp Ile Arg Gln Ser Pro Glu Lys Gly Leu
 50                  55                  60

Glu Trp Ile Gly Glu Ile Asn His Gly Gly Tyr Val Thr Tyr Asn Pro
65                   70                  75                  80

Ser Leu Glu Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
        450                 455                 460

Leu Gly Lys
465

<210> SEQ ID NO 94
<211> LENGTH: 236
<212> TYPE: PRT
<213> ORGANISM: Artificial sequence
<220> FEATURE:
<223> OTHER INFORMATION: Synthetic sequence

<400> SEQUENCE: 94

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Ala Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 95
<211> LENGTH: 6
<212> TYPE: PRT
<213> ORGANISM: Artificial sequence
<220> FEATURE:
<223> OTHER INFORMATION: Synthetic sequence

<400> SEQUENCE: 95

Asn Ser Tyr Ala Ile Ser
1               5

<210> SEQ ID NO 96
<211> LENGTH: 17
<212> TYPE: PRT
<213> ORGANISM: Artificial sequence
<220> FEATURE:
<223> OTHER INFORMATION: Synthetic sequence

<400> SEQUENCE: 96

Gly Ile Ile Pro Gly Phe Gly Thr Ala Asn Tyr Ala Gln Lys Phe Gln
1               5                   10                  15

Gly

<210> SEQ ID NO 97
<211> LENGTH: 11
<212> TYPE: PRT
<213> ORGANISM: Artificial sequence
<220> FEATURE:
<223> OTHER INFORMATION: Synthetic sequence

<400> SEQUENCE: 97

Arg Lys Asn Glu Glu Asp Gly Gly Phe Asp His
1               5                   10

<210> SEQ ID NO 98
<211> LENGTH: 119
<212> TYPE: PRT
<213> ORGANISM: Artificial sequence
<220> FEATURE:
<223> OTHER INFORMATION: Synthetic sequence

<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Asn Glu Glu Asp Gly Gly Phe Asp His Trp Gly Gln Gly
            100                 105                 110

Thr Leu Val Thr Val Ser Ser
            115

<210> SEQ ID NO 99
<211> LENGTH: 445
<212> TYPE: PRT
<213> ORGANISM: Artificial sequence
<220> FEATURE:
<223> OTHER INFORMATION: Synthetic sequence

<400> SEQUENCE: 99

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
         35                  40                  45

Gly Gly Ile Pro Gly Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Asn Glu Glu Asp Gly Gly Phe Asp His Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
        210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300
```

```
Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
        435                 440                 445

<210> SEQ ID NO 100
<211> LENGTH: 11
<212> TYPE: PRT
<213> ORGANISM: Artificial sequence
<220> FEATURE:
<223> OTHER INFORMATION: Synthetic sequence

<400> SEQUENCE: 100

Ser Gly Asp Asn Leu Gly Asp Tyr Tyr Ala Ser
1               5                   10

<210> SEQ ID NO 101
<211> LENGTH: 7
<212> TYPE: PRT
<213> ORGANISM: Artificial sequence
<220> FEATURE:
<223> OTHER INFORMATION: Synthetic sequence

<400> SEQUENCE: 101

Asp Asp Ser Asn Arg Pro Ser
1               5

<210> SEQ ID NO 102
<211> LENGTH: 10
<212> TYPE: PRT
<213> ORGANISM: Artificial sequence
<220> FEATURE:
<223> OTHER INFORMATION: Synthetic sequence

<400> SEQUENCE: 102

Gln Thr Trp Asp Gly Thr Leu His Phe Val
1               5                   10

<210> SEQ ID NO 103
<211> LENGTH: 107
<212> TYPE: PRT
<213> ORGANISM: Artificial sequence
<220> FEATURE:
<223> OTHER INFORMATION: Synthetic sequence

<400> SEQUENCE: 103

Asp Ile Glu Leu Thr Gln Pro Pro Ser Val Ser Val Ala Pro Gly Gln
1               5                   10                  15
```

```
Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu
                100                 105
```

<210> SEQ ID NO 104
<211> LENGTH: 213
<212> TYPE: PRT
<213> ORGANISM: Artificial sequence
<220> FEATURE:
<223> OTHER INFORMATION: Synthetic sequence

<400> SEQUENCE: 104

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 105
<211> LENGTH: 6
<212> TYPE: PRT
<213> ORGANISM: Artificial sequence
<220> FEATURE:
<223> OTHER INFORMATION: Synthetic sequence

<400> SEQUENCE: 105

Ser Asp Tyr Tyr Met His
1               5

<210> SEQ ID NO 106
<211> LENGTH: 17
<212> TYPE: PRT
<213> ORGANISM: Artificial sequence
<220> FEATURE:
<223> OTHER INFORMATION: Synthetic sequence

<400> SEQUENCE: 106

Val Ile Ser Gly Ser Gly Ser Asn Thr Tyr Tyr Ala Asp Ser Val Lys
1               5                   10                  15

Gly

<210> SEQ ID NO 107
<211> LENGTH: 10
<212> TYPE: PRT
<213> ORGANISM: Artificial sequence
<220> FEATURE:
<223> OTHER INFORMATION: Synthetic sequence

<400> SEQUENCE: 107

Arg Leu Tyr Ala Gln Phe Glu Gly Asp Phe
1               5                   10

<210> SEQ ID NO 108
<211> LENGTH: 118
<212> TYPE: PRT
<213> ORGANISM: Artificial sequence
<220> FEATURE:
<223> OTHER INFORMATION: Synthetic sequence

<400> SEQUENCE: 108

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Val Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ala Gln Phe Glu Gly Asp Phe Trp Gly Gln Gly Thr
            100                 105                 110

Leu Val Thr Val Ser Ser
        115

<210> SEQ ID NO 109
<211> LENGTH: 444
<212> TYPE: PRT
<213> ORGANISM: Artificial sequence
<220> FEATURE:
<223> OTHER INFORMATION: Synthetic sequence

<400> SEQUENCE: 109

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
         20                  25                  30

Tyr Met His Trp Val Arg Gln Ala Pro Gly Lys Gly Leu Glu Trp Val
         35                  40                  45

Ser Val Ile Ser Gly Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Leu Tyr Ala Gln Phe Glu Gly Asp Phe Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Asn Phe Gly Thr Gln Thr Tyr Thr Cys Asn Val Asp His Lys Pro Ser
                    195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
```

435                 440

<210> SEQ ID NO 110
<211> LENGTH: 11
<212> TYPE: PRT
<213> ORGANISM: Artificial sequence
<220> FEATURE:
<223> OTHER INFORMATION: Synthetic sequence

<400> SEQUENCE: 110

Ser Gly Asp Asn Ile Gly Ser Lys Tyr Val Ser
1               5                   10

<210> SEQ ID NO 111
<211> LENGTH: 7
<212> TYPE: PRT
<213> ORGANISM: Artificial sequence
<220> FEATURE:
<223> OTHER INFORMATION: Synthetic sequence

<400> SEQUENCE: 111

Ser Asp Ser Glu Arg Pro Ser
1               5

<210> SEQ ID NO 112
<211> LENGTH: 10
<212> TYPE: PRT
<213> ORGANISM: Artificial sequence
<220> FEATURE:
<223> OTHER INFORMATION: Synthetic sequence

<400> SEQUENCE: 112

Gln Ser Trp Asp Gly Ser Ile Ser Arg Val
1               5                   10

<210> SEQ ID NO 113
<211> LENGTH: 107
<212> TYPE: PRT
<213> ORGANISM: Artificial sequence
<220> FEATURE:
<223> OTHER INFORMATION: Synthetic sequence

<400> SEQUENCE: 113

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Lys Tyr Val
            20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu
            100                 105

<210> SEQ ID NO 114
<211> LENGTH: 213
<212> TYPE: PRT
<213> ORGANISM: Artificial sequence
<220> FEATURE:
<223> OTHER INFORMATION: Synthetic sequence

<400> SEQUENCE: 114

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Lys Tyr Val
            20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210
```